US009163255B2

(12) United States Patent
Chakraborty et al.

(10) Patent No.: US 9,163,255 B2
(45) Date of Patent: Oct. 20, 2015

(54) POLYNUCLEOTIDES DERIVED FROM CHICKPEA AND USES THEREOF

(75) Inventors: Subhra Chakraborty, New Delhi (IN); Niranjan Chakraborty, New Delhi (IN); Asis Datta, New Delhi (IN); Nasheeman Asraf, New Delhi (IN); Swaraj Basu, New Delhi (IN); Papri Nag, New Delhi (IN); Manindra Singh, New Delhi (IN)

(73) Assignee: National Institute of Plant Genome Research, New Delhi (IN)

( * ) Notice: Subject to any disclaimer, the term of this patent is extended or adjusted under 35 U.S.C. 154(b) by 610 days.

(21) Appl. No.: 13/393,340

(22) PCT Filed: Aug. 30, 2010

(86) PCT No.: PCT/IN2010/000573
§ 371 (c)(1),
(2), (4) Date: Feb. 29, 2012

(87) PCT Pub. No.: WO2011/024207
PCT Pub. Date: Mar. 3, 2011

(65) Prior Publication Data
US 2012/0159668 A1 Jun. 21, 2012

(30) Foreign Application Priority Data
Aug. 29, 2009 (IN) .......................... 1565/DEL/2009

(51) Int. Cl.
*C12N 15/82* (2006.01)
*C07K 14/415* (2006.01)
(52) U.S. Cl.
CPC .......... *C12N 15/8282* (2013.01); *C07K 14/415* (2013.01)
(58) Field of Classification Search
None
See application file for complete search history.

(56) References Cited

PUBLICATIONS

GenBank. Medicago trunculat clone MTYF5_F6_F7_F81G-G-2 unknown mRNA. 2008. Accession BT051691.1.*
Ashraf, N., et al., "Comparative analyses of genotype dependent expressed sequence tags and stress-responsive transcriptome of chickpea wilt illustrate predicted and unexpected genes and novel regulators of plant immunity," *BMC Genomics* 10:415, BioMed Central Ltd., England (2009).
Coram, T.E. and Pang, E.C.K., "Isolation and analysis of candidate ascochyta blight defence genes in chickpea. Part I. Generation and analysis of an expressed sequence tag (EST) library," *Physiol. Mol. Plant Pathol.* 66:192-200, Elsevier Ltd., England (2005).
Coram, T.E. et al., "Functional genomics in chickpea: an emerging frontier for molecular-assisted breeding," *Funct. Plant Biol.* 34:861-873, CSIRO Pub., Australia (2007).

Datta, S., et al., "IPCM_34 Wilt resistant chickpea leave library (JG 315) *Cicer arietinum* cDNA clone IPCM_34, mRNA sequence," retrieved from EBI Database accession No. GE213134, accessed Jun. 7, 2012.
Ewing, R.M., et al., "Large-Scale Statistical Analyses of Rice ESTs Reveal Correlated Patterns of Gene Expression," *Genome Res.* 9:950-959, Cold Spring Harbor Laboratory Press, United States (1999).
Gray, W.M., "Plant Defence: A New Weapon in the Arsenal," *Curr. Biol.* 12:R352-R354, Elsevier Science Ltd., England (2002).
Jantasuriyarat, C., et al., "Large-Scale Idnetification of Expressed Sequence Tags Involved in Rice and Rice Blast Fungus Interaction," *Plant Physiol.* 138:105-115. American Society of Plant Biologists, United States (2005).
Katagiri, F., "A global view of defense gene expression regulation—a highly interconnected signaling network," *Curr. Opin. Plant Biol.* 7:506-511, Current Biology Ltd., England (2004).
Koornneef, A. and Pieterse, M.J., "Cross Talk in Defense Signaling," *Plant Physiol.* 146:839-844, American Society of Plant Biologists, United States (2008).
LeBlanc, J.C., et al., "Global Response to Desiccation Stress in the Soil Actinomycete *Rhodococcus jostii* RHA1," *Appl. Environ. Microbiol.* 74:2627-2636, American Society for Microbiology, United States (2008).
Li, X., et al., "Genome-Wide Analysis of Basic/Helix-Loop-Helix Transcription Factor Family in Rice *Arabidopsis*," *Plant Physiol.* 141:1167-1184, American Society of Plant Biologists, United States (2006).
Melamed, D., et al., "Yeast translational response to high salinity: Global analysis reveals regulation at multiple levels," *RNA* 14:1337-1351, Cold Spring Harbor Laboratory Press, United States (2008).
Moskal, W., et al., "*Medicago truncatula* full length cdna cloning project," retrieved from EBI Database accession No. B7FHX6, accessed Jun. 7, 2012.
Murre, C., et al., "A New DNA Binding and Dimerization Motif in Immunoglobulin Enhancer Binding, *daughterless*, *MyoD*, and *myc* Proteins," *Cell* 56:777-783, United States (1989).
Nagata, T., et al., "Comparative molecular biological analysis of membrane transport genes in organisms," *Plant Mol. Biol.* 66:565-585, Kluwer Academic, Netherlands (2008).

(Continued)

*Primary Examiner* — Anne Kubelik
(74) *Attorney, Agent, or Firm* — Sterne, Kesssler, Goldstein, Fox P.L.L.C.

(57) ABSTRACT

Polynucleotides isolated from chickpea are disclosed herein. The disclosed polynucleotides of the present invention provide genotype-dependent spatial information on the presence and relative abundance of each gene. The transcriptomic analysis of the polynucleotides revealed (649) non-cannonical genes besides many unexpected candidates with known biochemical functions, which have never been associated with pathostress-responsive transcriptome. The polynucleotides disclosed in the present invention can be used as a molecular tool for isolation of novel genes from plants that can be used for plant improvement. Further, the polynucleotide responsible for improving immunity against fungal pathogen in plants is disclosed herein. The present invention also provides a method of improving immunity against fungal pathogen in plants. Transgenic plants exhibiting improved immunity against fungal pathogen are also provided in the present invention.

10 Claims, 9 Drawing Sheets

(56) References Cited

PUBLICATIONS

Nimbalkar, S.B., et al., "Differentially expressed gene transcripts in roots of resistant and susceptible chickpea plant (*Cicer arietinum* L.) upon *Fusarium oxysporum* infection," *Physiol.Mol. Plant Pathol.* 68:176-188, Elsevier Ltd., England (2006).

Ramírez, M., et al., "Sequencing and Analysis of Common Bean ESTs. Building a Foundation for Functional Genomics," *Plant Physiol.* 137:1211-1227, American Society of Plant Biolgists, United States (2005).

Satoh, K., et al., "Gene Organization in Rice Revealed by Full-Length cDNA Mapping and Gene Expression Analysis through Microarray," *PLoS One* 2:e1235, Public Library of Science, United States (2007).

Takabatake, T., et al., "Microarray-based global mapping of integration sites for the retrotransposon, intracisternal A-particle, in the mouse genome," *Nucleic Acids Res.* 36:e59, Oxford University Press, England (2008).

Toledo-Ortiz, G., et al., "The *Arabidopsis* Basic/Helix-Loop-Helix Transcription Factor Family," *The Plant Cell* 15:1749-1770, American Society of Plant Biologists, United States (2003).

Udall, J.A., et al., "A global assembly of cotton ESTs," *Genome Res.* 16:441-450, Cold Spring Harbor Laboratory Press, United States (2006).

Wellmer, F., "Genome-Wide Analysis of Gene Expression during Early *Arabidopsis* Flower Development," *PLoS Genetics* 2:e117, Public Library of Science, United States (2006).

White, J.A., et al., "A New Set of *Arabidopsis* Expressed Sequence Tags from Developing Seeds. The Metabolic Pathway from Carbohydrates to Seed Oil," *Plant Physiol.* 124:1582-1594, American Society of Plant Physiologists, United States (2000).

International Search Report for International Patent Application No. PCT/IN2010/000573, European Patent Office, Rijswijk, Netherlands, mailed Mar. 16, 2011.

Written Opinion of the International Searching Authority for International Patent Application No. PCT/IN2010/000573, European Patent Office, Rijswijk, Netherlands, mailed Mar. 16, 2011.

\* cited by examiner

POLYNUCLEOTIDES DERIVED FROM CHICKPEA AND USES THEREOF

REFERENCE TO SEQUENCE LISTING SUBMITTED ELECTRONICALLY

The content of the electronically submitted sequence listing, file name sequence_listing.ascii.txt, size 3,528,120 bytes; and date of creation May 21, 2013, filed herewith, is incorporated herein by reference in its entirety.

FIELD OF INVENTION

The present invention relates to polynucleotides derived from chickpea associated with growth and development and hormone and stress response including immunity in plants.

BACKGROUND OF THE INVENTION

The ultimate phenome of any organism is modulated by regulated transcription of many genes. Characterization of genetic makeup is thus crucial for understanding the molecular basis of phenotypic diversity, evolution and response to intra- and extra-cellular stimuli. Living cells have evolved to perceive and integrate different signals from their surroundings and to respond by modulating the appropriate gene expression. Expressed sequence tags (ESTs) provide an invaluable resource for analysis of gene expression associated with specific organs, growth conditions, developmental processes and responses to various environmental stresses (White et al., 2000; Ewing et al., 1999; Jantasuriyarat et al., 2005). It bridges the gap between the genome sequences and gene function. ESTs have been useful for intra- and intergenomic comparisons, gene discovery, generation of single nucleotide polymorphisms (SNPs), cloning of genes from MStag peptide sequences, transcript pattern characterization, identifying splice variants, erroneous annotations in the genome database and incomplete prediction of gene structure (Ramirez et al., 2005; Udall et al., 2006). Further, the transcriptome of cells and organs comprise a focused set of transcripts that fulfills discrete but varied cellular functions. The analyses of organ specific transcriptome provide additional information about localization of gene function and pathway compartmentalization. Whereas the transcriptome research is quite advanced in animals, yeast, bacteria and reference plants like *Arabidopsis* and rice (Takabatake et al., 2008; Melamed et al., 2008; LeBlanc et al., 2008; Wellmer et al., 2006; Satoh et al., 2007) there is relatively less information in crop plants.

Legumes are valuable agricultural and commercial crops that serve as important nutrient sources for human diet and animal feed. About one third of human nutrition comes from legumes and in many developing countries, legumes serve as the only source of protein. Many secondary metabolites in legumes have been implicated in defense and are of particular interest as novel pharmaceuticals. Five tribes constitute the family fabaceae, of which one representative genus each from four tribes have been used to generate ESTs. However, the tribe ciceri having a single genus *Cicer*, remained as the understudied legume. Chickpea is the world's third most important food legume grown in over 40 countries representing all the continents. Despite its importance in plant evolution, role in human nutrition and stress adaptation, very little ESTs and differential transcriptome data is available, let alone genotype-specific gene signatures. It is grown on about 10 mha area worldwide and the global production exceeds 8 million tons. In many water-deficient regions of the world, it serves as an important protein-rich food and an increasingly valuable traded commodity. Chickpea has one of the highest nutritional compositions of edible legume and does not contain any specific major anti-nutritional factor, rather it is used in herbal medicine. Despite the importance of chickpea in the study of plant evolution, its role in nutritional requirement in humans, and stress adaptation nothing is known about the genes responsible for these traits—primarily because it is recalcitrant to genetic analysis. Unlike genetically tractable plants such as tomato, maize and *Arabidopsis*, chickpea produces a limited number of seeds. Furthermore, its genome is large (732 Mbp) as compared to *Arabidopsis* (125 Mbp). Consequently, chickpea has remained outside the realm of both modern genome-sequencing initiatives and large scale functional genomics studies. Currently available completely annotated plant genome sequences make it possible to study the genomes of agriculturally important genetically complex crop plants such as chickpea by comparing the ESTs derived from them. Only very recently, attention has been given from both genomics and proteomics perspect to this important food legume. Because of its evolutionary position as a key node within legumes as well as its nutritional and medicinal significance to humans, chickpea is ideally suited for genomic prospecting.

Transcriptional programs that regulate development and stress response are exquisitely controlled in space and time. Elucidating these programs that underlie development is essential to understand the acquisition of cell and tissue identity. Root in higher plants is a highly organized structure that plays a key role in nutrient acquisition and water uptake besides its primary function of mechanical support to the plant. Nevertheless, it is essentially the entry point for the soil borne pathogens into the plant body. Of the soil borne root pathogen, vascular wilt is the most important disease. Vascular wilt caused by *Fusarium* is ubiquitous evolutionarily and effects crop plants across families. In particular, chickpea wilt, is widespread in occurrence and on an average causes substantial loss of 10 to 15% in production every year worldwide. During the infection process the fungus invades roots and spreads systemically through the host's vascular system, breaking down the cell walls to form gels that block the plant's transport system thereby causing yellowing and wilting symptoms. In general, the wilt symptoms appear as chlorotic spots on the lower leaves followed by discoloration and necrosis. Vascular discoloration occurs from the roots to the young stems, followed by a yellowing and wilting of the leaves before final necrosis. When uprooted the stem is split vertically and internal discoloration is visible in pith and xylem. The susceptible genotypes take less than 25 days for wilting whereas the resistant ones do not show any symptoms of wilting up to 60 days. *Fusarium*, an ubiquitous pathogen that causes disease not only in plants but also is a threat to other living organisms, including human (Nucci & Anaissie, 2007; Sander et al., 1998).

Microarray technology is a powerful tool that can be used to identify the presence and level of expression of a large number of polynucleotides in a single assay. Strength of microarray technology is that it allows the identification of differential gene expression simply by comparing patterns of hybridization.

Immune responses are controlled by dynamic and variable gene expression changes which lead to reprogramming of many cellular functions. It has been postulated that the outcome of the defense response seems to be finely tuned by cross-talk between various signaling pathways (Koornneef and Pieterse, 2008) resulting in quantitative and/or kinetic effects on the resistance response (Katagiri, 2004). Basic helix-loop-helix (bHLH) transcription factors represent a family of proteins that contains a bHLH domain, a motif involved in DNA binding and dimerization (Murre et al., 1989). Members of the bHLH TF superfamily proteins are known to perform diverse regulatory functions. In animals they act as regulatory factors in different processes such as neurogenesis, cardiogenesis, myogenesis, and hematopoiesis (Jones, 2004). Although, the members of bHLH TF superfamily have been studied in mammals, but investigation of plant bHLH is still in its infancy.

The genetic improvements in plants beyond current capabilities are urgently needed for production of more food worldwide, implying thereby enhanced growth and development of plants with increased tolerance to stress. Environmental stresses including disease have major effects on agricultural production and food security. During the past, there have been attempts to develop high yielding plant varieties by engineering stress tolerance. Although there have been isolated instances of reports on developing plants with increased stress tolerance but not much has been achieved towards genetic enhancement of plants in terms of immunity. Thus, there is a critical need to discover molecules such as polynucleotides, genes, ESTs of agricultural importance, their functional analyses and exploitation for sustainable crop production.

SUMMARY OF THE INVENTION

One aspect of the present invention relates to ESTs isolated form chickpea having nucleotide sequence as set forth in SEQ ID NO: 1 to 6272, wherein the ESTs are related to various functions selected from a group consisting of cell signaling, transcription, RNA processing and modification, translation, post translational modification, protein turnover, nucleotide binding, metabolism, cellular transport, homeostasis, hormone response, cell cycle, DNA metabolism, development, cytoskeletal organization, cellular redox, energy metabolism, secondary metabolism, defense and stress response.

Another aspect of the present invention relates to an isolated nucleotide sequence as set forth in SEQ ID NO: 6273 encoding the protein having amino acid sequence as set forth in SEQ ID NO: 6274.

Another aspect of the present invention relates to a recombinant vector comprising the nucleotide sequence as set forth in SEQ ID NO: 6273 encoding the protein having amino acid sequence as set forth in SEQ ID NO: 6274, wherein the nucleotide sequence is operably linked to a promoter.

Another aspect of the present invention relates to a recombinant host cell comprising the nucleotide sequence as set forth in SEQ ID NO: 6273 encoding the protein having amino acid sequence as set forth in SEQ ID NO: 6274, wherein the nucleotide sequence is operably linked to a promoter, wherein the host cell is E. coli, Agrobacterium or yeast.

Yet another aspect of the present invention relates to a method of improving immunity against fungal pathogen in plants, said method comprises transforming a plant cell with a polynucleotide having the nucleotide sequence as set forth in SEQ ID NO: 6273 encoding protein having amino acid sequence as set forth in SEQ ID NO: 6274, selecting the transformed plant cell and regenerating the transformed plant cell into transgenic plant showing improved immunity to the fungal pathogen.

Further aspect of the present invention relates to a transgenic plant having improved immunity against a fungal pathogen, wherein the transgenic plant over-expresses a polynucleotide having the nucleotide sequence as set forth in SEQ ID NO: 6273.

BRIEF DESCRIPTION OF ACCOMPANYING DRAWING

Figure 4:
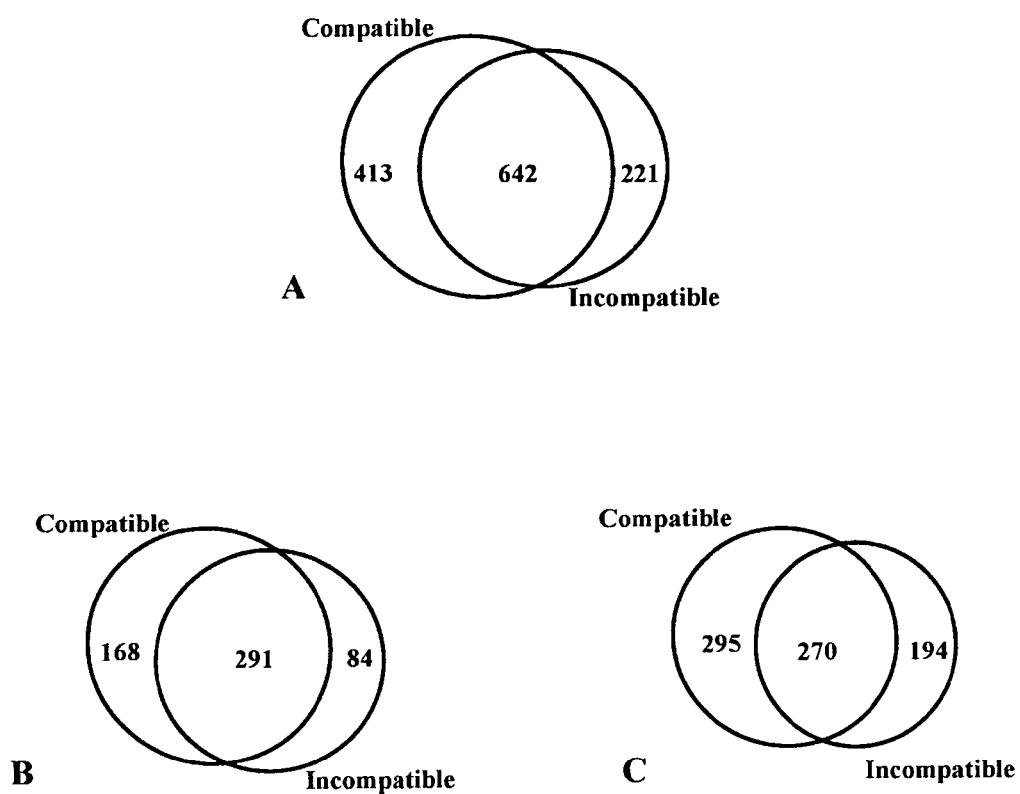

FIG. 4 shows comparative analyses of differentially expressed CaESTs. Venn represents (A) total differential exclusive and common expression pattern during compatible and incompatible interactions, (B) up-regulated differential exclusive and common expression pattern during compatible and incompatible interactions and (C) down-regulated differential exclusive and common expression pattern during compatible and incompatible interactions.

Figure 5:
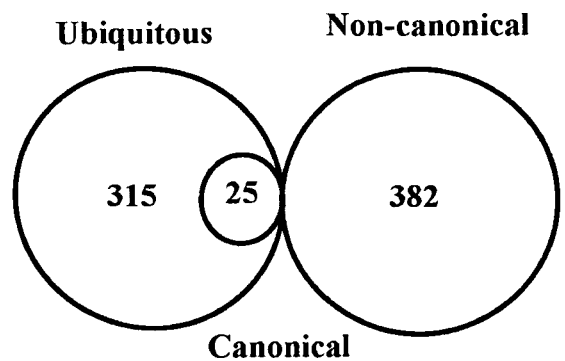

FIG. 5 shows comparative analysis of chickpea stress responsive genes having a differential microarray expression with earlier known stress related genes. Venn represents the overlap between ubiquitous, canonical and non canonical genes and the numbers signify unique and common stress responsive differentially expressed genes.

Figure 6:
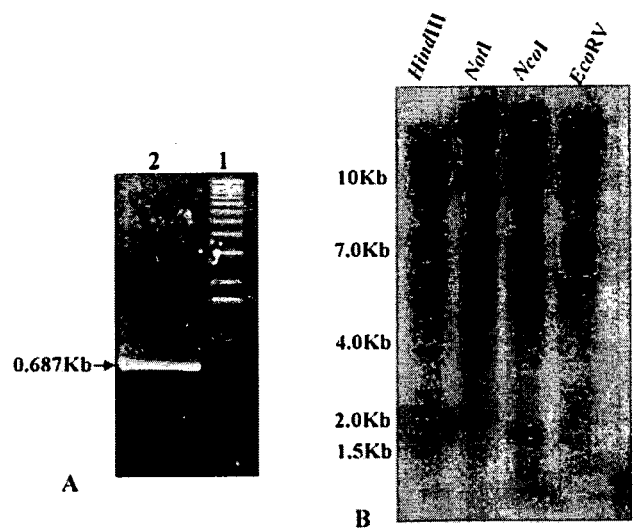

FIG. 6 shows IRF817 is an intronless and low copy number gene. (A) PCR amplified product of IRF817 using genomic DNA as template and ORF end primers. Lane 1 and 2 indicate 1 Kb ladder and PCR product, respectively and (B) Southern blot indicating the copy number of IRF817. Each lane was loaded with 10 µg of chickpea genomic DNA digested with indicated restriction endonucleases and the blot was hybridized with $^{32}$P-labeled full length cDNA of IRF817 as probe. Molecular weight marker in kb is indicated on the left.

Figure 7:
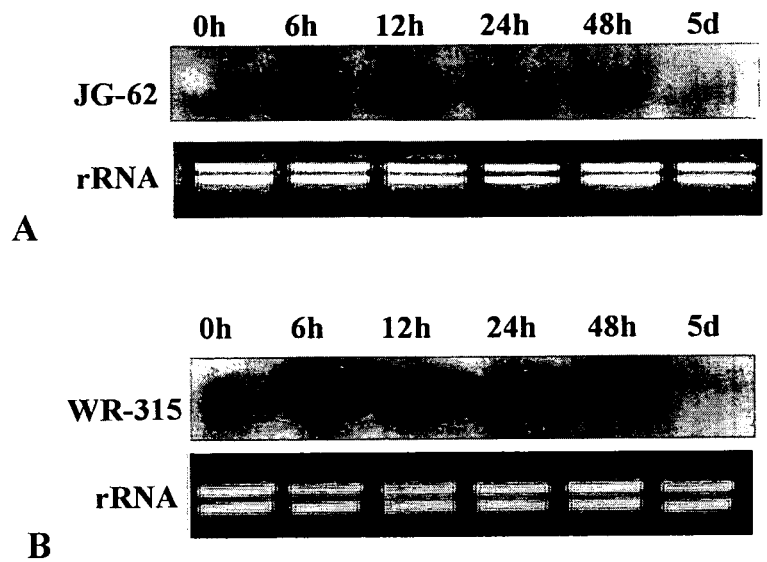

FIG. 7 shows genotype-specific expression pattern of IRF817 in response to patho-stress as determined by northern blot analysis, (A) Susceptible (JG-62) and (B) resistant (WR-315) genotypes of chickpea. The lanes represent various post-infection time points. 20 µg of total root RNA isolated from 25-day old chickpea seedlings harvested at various time points after pathogen infection were separated by 1.5% agarose gel. The RNA blot was hybridized with a $^{32}$P-labeled cDNA fragment of IRF817. The image of ethidium bromide stained rRNA in the lower panel shows equivalent loading and RNA quality.

Figure 8:
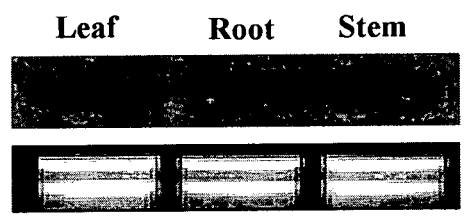

FIG. 8 shows organ specific expression pattern of IRF817 as determined by northern blot analysis. The RNA blot was hybridized with a $^{32}$P-labeled cDNA fragment of IRF817. The image of ethidium bromide stained rRNA in the lower panel shows equivalent loading and RNA quality; L, leaf; R, root; S, stem.

Figure 9:
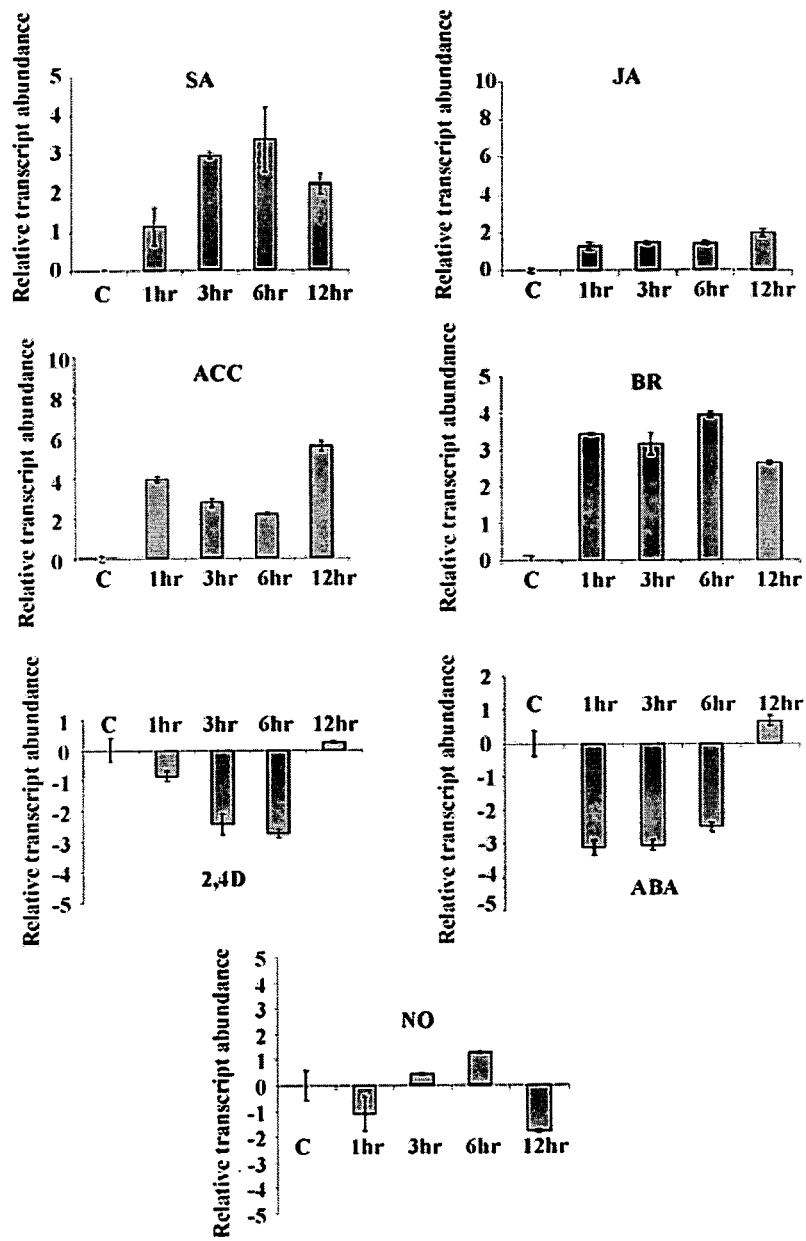

FIG. 9 shows relative transcript level of IRF817 in response to various hormones as determined by real time PCR. Transcript levels were normalized by 18S transcript level. Error bars indicate SD of three real time PCR experiments. C denotes the control.

Figure 10:
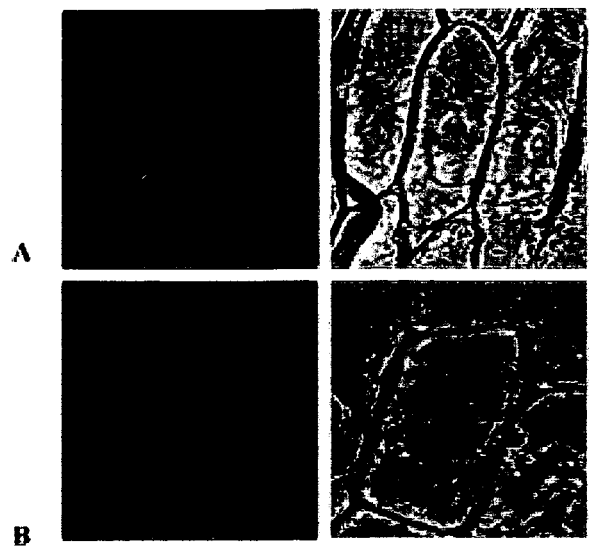

FIG. 10 shows sub-cellular localization of CaIRF817. Onion epidermal cells bombarded with (A) empty vector (GFP) and (B) fusion gene construct (IRF817-GFP). The GFP fluorescence was detected using confocal laser-scanning microscope. The right panel shows the corresponding phase contrast image.

Figure 11:
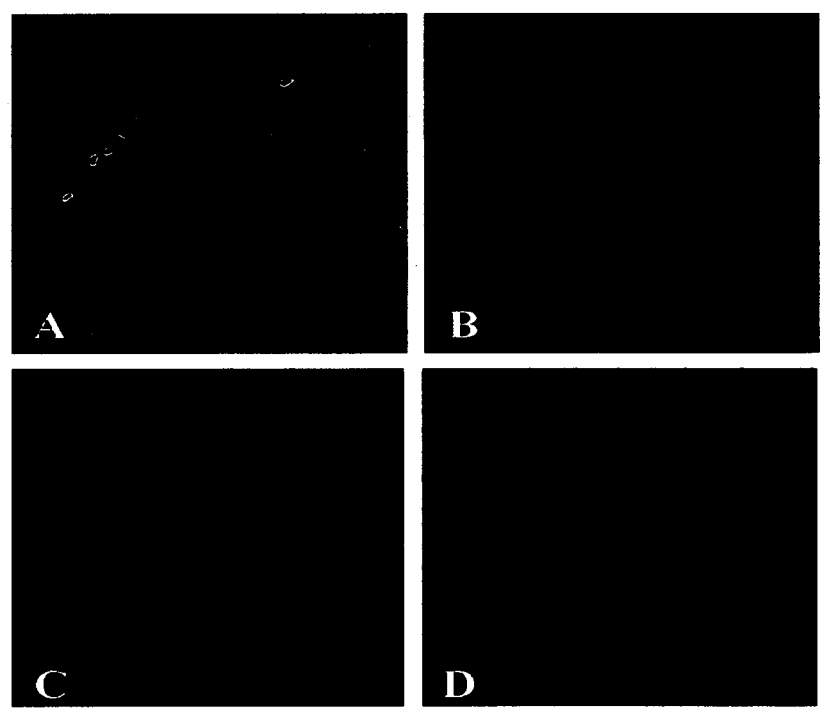

FIG. 11 shows transgenic root expressing IRF817 is immune to patho-stress. (A-D) Root colonization of the pathogen is spatially associated with the absence of intact plant nuclei. Root segment double-stained for intact plant nuclei (DAPI; B and D) and fungal hyphae (WGA-Texas Red; A and C). Control root heavily colonized by fungal hyphae (A) contains only a few DAPI-stained nuclei (B) while transgenic root with minor fungal colonization (C) contains a high number of DAPI-stained nuclei (D).

Figure 12:
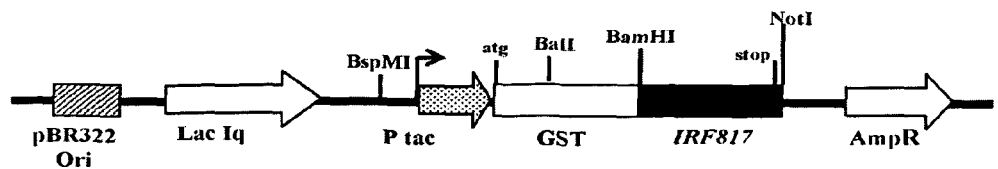

FIG. 12 shows schematic diagram of recombinant bacterial expression vector GST-IRF817

Figure 13:
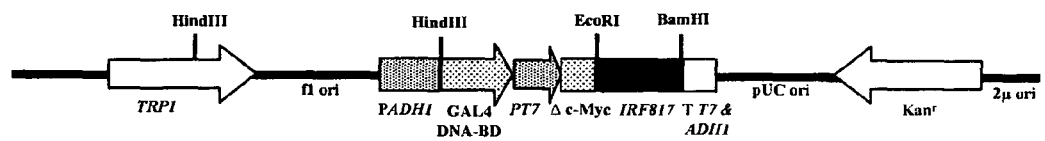

FIG. 13 shows schematic diagram of recombinant yeast expression vector Gal4-IRF817

Figure 14:
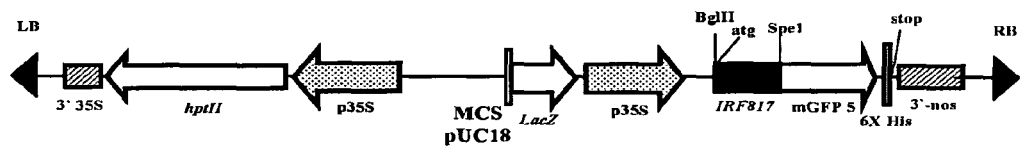
Figure 15:
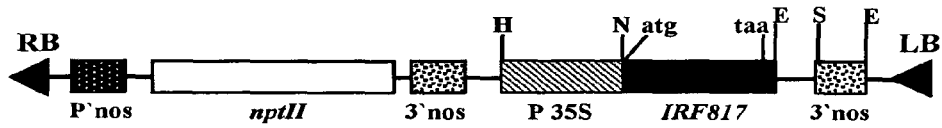

FIG. 14 shows schematic diagram of recombinant plant expression vector IRF817-GFP FIG. 15 shows schematic diagram of recombinant plant expression vector Cam V35S::IRF817

SEQUENCE LISTING: The patent application contains a lengthy sequence listing section. A copy of the sequence listing is provided herein in electronic format.

DETAILED DESCRIPTION OF THE INVENTION

Expressed sequence tags, or ESTs, are short sequences of randomly selected clones from a cDNA (or complementary DNA) library which are representative of the cDNA inserts of these randomly selected clones.

Expressed sequence tags, or ESTs or polynucleotides can be used interchangeably here.

The present invention provides polynucleotides associated with vascular wilt response transcriptome in chickpea. Further, the present invention provides clusters of genes that are regulated in response to a stress condition in chickpea. Such clusters include, for example, plant polynucleotides whose expression is altered in response to a stress condition. The identification of such clusters, using microarray technology, has allowed the identification of various plant genes such as stress-regulated genes and genes associated with hormone response and plant growth and development. Thus, the invention provides isolated polynucleotide portions of chickpea plant stress regulated genes. Such sequences include but not limited to sequences encoding transcription factors; enzymes, including kinases; and structural proteins, chromatin modifiers, signaling molecules, hormone responsive proteins, translational proteins and proteins involved in post-translational modifications and protein fate.

The present invention provides Expressed Sequence Tags (ESTs) isolated from chickpea. The present invention particularly provides 6272 gene sequences of immune-response pathway that would provide genotype-dependent spatial information on the presence and relative abundance of each gene. The sequence assembly led to the identification of a CaUnigene set of 2013 transcripts comprising of 973 contigs and 1040 singletons, two-third of which represent new chickpea genes hitherto undiscovered.

The present invention further provides 209 gene families and 262 genotype-specific SNPs. Further, several novel transcription regulators were identified indicating their possible role in immune response. The transcriptomic analysis revealed 649 non-cannonical genes besides many unexpected candidates with known biochemical functions, which have never been associated with pathostress-responsive transcriptome.

In the present study, two genotypes JG-62 and WR-315 were used which are known to be susceptible and resistant to *Fusarium* wilt, respectively. The localization of the fungus was limited in the resistant cultivar while extensive colonization occurs in susceptible one by fourth to fifth day post infection. Externally the extent of mycelial colonization is manifested in the form of browning of the roots after 72 hours in the susceptible genotype while no such discoloration is evident in the resistant one.

To understand the regulatory networks and metabolic pathways governing genotype-specific cellular responses towards different signals, we have initiated ESTablishing CaUnigene dataset and a genome-wide analysis of gene expression in this food legume. As a first step towards this, we have developed ESTs and stress responsive transcriptome of chickpea, as a basis for future transcriptome and proteome comparisons of genetic mutants, pathogen-infected and/or environmentally challenged plants.

The present invention provides a total of 6272 high quality ESTs were identified, functionally annotated, computationally analysed and classified into different functional categories. Of the 2013 genes, 807 were identified as previously uncharacterized. In addition, we have developed a cDNA based microarray chip and examined the global state of gene expression in the chickpea root during vascular wilt to identify the potential innate immune responsive candidates involved in the complex regulatory network that may function in this organ. These transcriptional signatures often predict previously unknown cellular functions. ESTablished set of pathostress-responsive organ-specific unigenes and the putative differentially expressed genes identified from the present study will provide a foundation for future investigation of the expression and function of the genes and proteins to build the interactome map at system level of chickpea and other legumes. In addition, gene mining of these databases, aided by microarray chip, can be used to select candidate genes involved in plant immunity. In the future, it will also be interesting to compare the spatial and temporal transcriptional complexity that underlies organ-specific innate immune response in other multicellular organisms.

The gene expression profiling led to the identification of 1276 differential genes out of which 413 were specific to susceptible and 221 specific to resistant genotype while 643 were common in both. Using this approach we found that out of 6072 probe sets representing 1749 unigenes present on the microarray, a total of 1276 genes were significantly regulated in at least one of the time points in one of the genotypes. Out of this 1055 were differentially expressed in susceptible and 863 in resistant genotype. Furthermore, among the significantly expressed genes, 413 were unique to susceptible; 221 unique to resistant and 642 common in both the genotypes.

We have identified expression patterns of hallmark defense genes and identification of several novel previously unidentified immune responsive genes.

In order to gain a detailed understanding of how various genes known to perform varied functions have an overall impact on the molecular functioning of the cell in response to different stresses, we developed a multinetwork based on our microarray gene expression data together with known protein-protein interactions. Visual inspection of the resulting interactome revealed highly connected metabolic and regulatory networks. In this study, we have focused our attention on immune responsive regulatory network. 572 genes involved in the regulatory network were found to be differential in the temporal microarray gene expression data. Of the total 572 genes 391 of them came out in the form of a statistically significant protein interaction network. The resulting network was densely organized and consisted of many coherent subnetworks to which biological significance was assigned. These subnetwork modules seemed to have organized roles in stress response and included cellular transport and assembly, transcription, translation and post translational modifications.

The interactome data disclosed in the present invention also suggest the presence of a multi-connected regulatory network and sub-networks comprising of 391 statistically significant candidates for immune-response pathway. Of these, a major transcriptional sub-network revealed presence of many transcription factors as essential regulatory components.

Plant immunity and susceptibility depend on a complex exchange of signals and responses occurring under given environmental conditions. In order to highlight which of the processes hold common ground and which defined immunity and susceptibility through their expression, we evaluated our data by constructing a process map. The results showed for the first time that while translation initiation and elongation seemed to be predominant in susceptible genotype, protein modification particularly phosphorylation was predominant in the resistant one. This suggests that apart from transcriptional control, translational and post translational modifications play a key role in mediating plant immune responses.

Our study establishes a comprehensive catalogue of the immune-responsive root transcriptome with insight into their identity and function. The development, detailed analysis of CaEST datasets and global gene expression by microarray provide new insight into the commonality and diversity of organ-specific immune-responsive transcript signatures and their regulated expression shaping the species specificity at genotype level. This is the first report on differential transcriptome of an unsequenced genome during vascular wilt.

Transcriptome profiling of the *Cicer arietinum L.* under patho-stress identified an array of differentially regulated components. Among the differentially regulated components, an EST was identified as gene encoding for bHLH protein, designated IRF817 (Immune responsive factor 817). We have investigated the gene structure and organization, and demonstrated, for the first time, that IRF817 is involved in immune-response pathway in plants. Expression of IRF817 was found to be regulated not only by patho-stress but also by different hormones and no treatments, suggesting its possible role in cellular development and environmental tolerance besides its role in plant immune response. IRF817 was found to be localized in the nucleus and acts as a regulatory molecule for stress-responsive signaling, including plant immunity. Overexpression of IRF817 in transgenic chickpea roots led to increased immunity compared to wild-type plants.

Chickpea EST Database

In an attempt to construct a functional EST dataset for discovering subset of genotype dependent, organ specific and extra and intra cellular stimuli responsive genes expressed in chickpea, in this study we have constructed two suppression-subtracted cDNA libraries, one from vascular wilt susceptible genotype (JG-62) and the other from resistant genotype (WR-315). The source of RNA for each library was root and collar tissue from the 25-d-old chickpea seedlings challenged with wilt pathogen, *Fusarium oxysporum ciceri* race 1, vs control tissue. In total, 6955 ESTs were generated and sequenced from the two libraries out of which 2908 were from susceptible and 4047 from resistant genotypes. Although no chimeric sequence was found, however about 9.8% of the sequences were discarded due to low quality of the sequence, short sequence length, sequence from other organellar origin or the absence of the insert and the remaining 6272 ESTs were considered for sequence assembly (Table 1). The high quality ESTs that passed the base calling, appropriate length, vector masking and mitochondrial filters were assembled into contigs using CAP3 program. The 6272 high quality sequences had an average read of 366 bp and a cumulative length of 2.29 Mbp. Of the total 6272 ESTs, 1040 were found to be classified as singletons whereas 5232 assembled into 973 contigs (Table 2). The redundancy of clones in the contigs ranged from 2 to 230. The total contigs and singletons comprised a non redundant chickpea unigene (CaUnigene) set of 2013 different transcripts 3.9% of the unigenes (79) contained more than 10 sequences per contig. Of the total high quality ESTs, 1202 were specific to susceptible genotype whereas 2168 were specific to resistant genotype and 2902 were common to both. The abundance of transcripts, shapes or results in a genotype specific function in response to stimuli in a given space and time. Absence of chimeras, high percentage of good quality sequences and good average insert size suggested that the libraries were of high quality (Table 1).

Functional Annotation and Classification of Chickpea ESTs

In order to understand the function of immune-responsive ESTs, the entire set of 2013 CaUnigenes were annotated on the basis of similarities to the known or putative ESTs in the NCBI database. Using the best hits found by BLAST, an inferred putative function was assigned to the sequences and were sorted into various functional categories. We were able to assign function to 60% of the genes while our data analysis revealed that 18.28% of the CaUnigenes belong to no significant homology (NSH) class. In addition, 18.33% and 3.47% of the unigenes matched with hypothetical and unknown proteins respectively. Genes were assigned to the functional classes according to their biochemical function using gene function databases like GO (www.geneontology.org), metacyc (www.metacyc.org) and COG (www.ncbi.nlm.nih.gov/COG). However, the classification of transcripts is only tentative, since the biological function of many genes identified has not yet been established experimentally. The distribution of ESTs into diverse functional classes as shown in additional is described below.

Genes Involved in Regulatory Pathways (Cell Signaling and Transcription and RNA Processing and Modification)

Genes involved in cell signaling, transcription and RNA processing are known to regulate many cellular responses in an organism. Our data showed the presence of different types of protein kinases in both susceptible and tolerant chickpea genotypes. While serine/threonine protein kinase (contig86), Serine/threonine protein kinase active site (CaF1_JIE_03_A_05) and somatic embryogenesis receptor-like kinase were present only in the susceptible genotype; flag-tagged protein kinase domain of putative MAPKKK and protein kinase (CaF1_WIE_51_C_11) were found in the resistant one. Protein kinases are involved in disease response via a signaling cascade presumably conserved in plants, insects and mammals while somatic embryogenesis related kinases are associated with brassinosteroid signaling pathway that plays a key role in plant defense. The EST data revealed many components of calcium signaling such as calmodulin, calcium dependent calmodulin independent kinase, CIP kinase and calcium/calmodulin-regulated receptor-like kinase in both the genotypes indicating an elaborate role of calcium signaling in immune response. The subsets of 14-3-3 proteins were also identified in both susceptible and resistant genotypes. For example, contigs 527, 568, 947 and singletons CaF1_WIE_13_A_05, CaF1_WIE_55_G_01 representing 14-3-3 gene family were present in the resistant genotype while the other member of this gene family, contig 133, was present only in the susceptible one. 14-3-3 has earlier been shown to interact with fusicoccin, the fungal toxin that causes membrane hyperpolarization through activation of plasma membrane $H^+$ ATPase. Other pathostress-responsive signaling components identified are WD40-like protein, response regulator receiver, and leucine-rich repeat (LRR) proteins. While WD40 and LRR proteins were found in both the genotypes, response regulator receiver was exclusive to the susceptible genotype. The LRR proteins are known to play role in defense signaling. While WD40-like proteins are reported to be involved in varied functions including organogenesis; vacuolar trafficking and light signaling their role in immune response is not known.

The potentially increased activity of various signaling pathways is associated with differential expression of many families of transcription factors during plant pathogenesis. The functional class of transcription associated genes, in this study, constituted about 3.58% of the total ESTs that comprised families of transcription factors including zinc finger, MYB, BEL 1-like homeodomain transcription factor, homeodomain leucine zipper HDZ3, G-box binding PG2, Zinc finger GATA-type, putative AP2-binding protein, bHLH and WRKY. While exploring the source of the ESTs coding for these transcription factors, an important and noteworthy observation was that a particular class of transcription regulators showed predominance or was specific to either susceptible or resistant genotype. For example, Myb and HDZ classes were predominant, whereas, PR related transcription factor and WRKY were exclusive to the resistant genotype. On the other hand BEL 1-like homeodomain transcription factor, NOT2/NOT3/NOT5 and G-box binding protein PG2 were found only in the susceptible genotype. This data suggests that interplay of a broad spectrum of transcription factors possibly regulates multiple signaling cascades during immune-stress.

Various RNA binding proteins have potential to modulate gene expression and might be involved in processes like RNA metabolism, mRNA splicing, ribosome biogenesis, transport and translation. We observed the presence of dead box RNA helicase, pre-mRNA processing ribonucleoprotein region, splicing factor 3B subunit 10 and RNA-binding region RNP-1 during vascular wilt of chickpea. All these genes were more abundant in resistant genotype. While dead box RNA helicase was reported to be involved in development and stress responses the role of splicing factor and RNA-binding region RNP-1 in pathostress is yet to be established.

In one embodiment the present invention provides ESTs derived from chickpea, wherein the ESTs are related to signaling. These ESTs are CaF1_JIE_01_D_01 SEQ ID NO:32, CaF1_JIE_02_C_11 SEQ ID NO:97, CaF1_JIE_02_D_11 SEQ ID NO:107, CaF1_JIE_02_H_04 SEQ ID NO:136, CaF1_JIE_03_A_05 SEQ ID NO:147, CaF1_JIE_03_B_10 SEQ ID NO:155, CaF1_JIE_03_C_02 SEQ ID NO:158, CaF1_JIE_03_E_06 SEQ ID NO:178, CaF1_JIE_06_D_11 SEQ ID NO:404, CaF1_JIE_06_F_09 SEQ ID NO:419, CaF1_JIE_07_H_04 SEQ ID NO:508, CaF1_JIE_08_B_09 SEQ ID NO:533, CaF1_JIE_08_B_11 SEQ ID NO:535, CaF1_JIE_08_D_03 SEQ ID NO:548, CaF1_JIE_08_F_01 SEQ ID NO:567, CaF1_JIE_08_H_09 SEQ ID NO:595, CaF1_JIE_08_H_10 SEQ ID NO:596, CaF1_JIE_09_C_10 SEQ ID NO:625, CaF1_JIE_09_E_09 SEQ ID NO:1289, CaF1_JIE_09_F_04 SEQ ID NO:1295, CaF1_JIE_10_E_04 SEQ ID NO:1340, CaF1_JIE_12_B_05 SEQ ID NO:1434, CaF1_JIE_12_B_06 SEQ ID NO:1435, CaF1_JIE_12_E_05 SEQ ID NO:1460, CaF1_JIE_12_E_08 SEQ ID NO:1461, CaF1_JIE_14_A_04 SEQ ID NO:1522, CaF1_JIE_15_B_08 SEQ ID NO:1597, CaF1_JIE_15_B_11 SEQ ID NO:1600, CaF1_JIE_15_D_10 SEQ ID NO:1616, CaF1_JIE_18_G_02 SEQ ID NO:1821, CaF1_JIE_19_A_08 SEQ ID NO:1842, CaF1_JIE_19_F_10 SEQ ID NO:1885, CaF1_JIE_20_A_11 SEQ ID NO:1913, CaF1_JIE_20_G_02 SEQ ID NO:1966, CaF1_JIE_20_H_08 SEQ ID NO:1983, CaF1_JIE_22_G_11 SEQ ID NO:2130, CaF1_JIE_23_B_02 SEQ ID NO:2153, CaF1_JIE_23_B_03 SEQ ID NO:2154, CaF1_JIE_23_G_02 SEQ ID NO:2201, CaF1_JIE_24_F_09 SEQ ID NO:2272, CaF1_JIE_24_G_10 SEQ ID NO:2280, CaF1_JIE_25_B_04 SEQ ID NO:2300, CaF1_JIE_25_G_02 SEQ ID NO:2332, CaF1_JIE_26_D_08 SEQ ID NO:2377, CaF1_JIE_26_G_06 SEQ ID NO:2398, CaF1_JIE_26_H_11 SEQ ID NO:2409, CaF1_JIE_29_F_07 SEQ ID NO:2553, CaF1_JIE_29_G_07 SEQ ID NO:2558, CaF1_JIE_31_D_07 SEQ ID NO:2639, CaF1_JIE_31_D_09 SEQ ID NO:2640, CaF1_JIE_32_E_11 SEQ ID NO:2703, CaF1_JIE_32_F_11 SEQ ID NO:2708, CaF1_JIE_33_A_07 SEQ ID NO:2725, CaF1_JIE_33_B_01 SEQ ID NO:2729, CaF1_JIE_33_B_02 SEQ ID NO:2730, CaF1_JIE_33_B_03 SEQ ID NO:2731, CaF1_JIE_33_C_03 SEQ ID NO:2742, CaF1_JIE_33_D_01 SEQ ID NO:2749, CaF1_JIE_33_E_03 SEQ ID NO:2756, CaF1_JIE_33_H_04 SEQ ID NO:2775, CaF1_JIE_34_H_05 SEQ ID NO:2831, CaF1_JIE_34_H_06 SEQ ID NO:2832, CaF1_JIE_34_H_11 SEQ ID NO:2837, CaF1_JIE_35_C_02 SEQ ID NO:2854, CaF1_JIE_35_E_02 SEQ ID NO:2870, CaF1_JIE_35_G_11 SEQ ID NO:2885, CaF1_JIE_36_F_01 SEQ ID NO:2929, CaF1_JIE_36_G_11 SEQ ID NO:2939, CaF1_JIE_36H_02 SEQ ID NO:2940, CaF1_JIE_37_A_06 SEQ ID NO:2951, CaF1_JIE_37_C_09 SEQ ID NO:2963, CaF1_JIE_38_B_08 SEQ ID NO:3012, CaF1_JIE_39_F_05 SEQ ID NO:3093, CaF1_JIE_39_G_11 SEQ ID NO:3104, CaF1_JIE_40_E_11 SEQ ID NO:3153, CaF1_JIE_41_D_02 SEQ ID NO:3202, CaF1_JIE_41_E_09 SEQ ID NO:3217, CaF1_JIE_41_F_02 SEQ ID NO:3221, CaF1_JIE_41_G_06 SEQ ID NO:3232, CaF1_JIE_41_G_09 SEQ ID NO:3234, CaF1_JIE_42_A_07 SEQ ID NO:3247, CaF1_JIE_42_E_02 SEQ ID NO:3260, CaF1_JIE_42_E_04 SEQ ID NO:3261, CaF1_JIE_42_E_05 SEQ ID NO:3262, CaF1_JIE_42_F_04 SEQ ID NO:3264, CaF1_WIE_01_C_02 SEQ ID NO:646, CaF1_WIE_01_E_07 SEQ ID NO:669, CaF1_WIE_01_G_01 SEQ ID NO:681, CaF1_WIE_02_D_09 SEQ ID NO:726, CaF1_WIE_02_E_09 SEQ ID NO:736, CaF1_WIE_04_A_06 SEQ ID NO:822, CaF1_WIE_04_C_06 SEQ ID NO:840, CaF1_WIE_05_A_09 SEQ ID NO:893, CaF1_WIE_05_E_05 SEQ ID NO:925, CaF1_WIE_06_A_05 SEQ ID NO:960, CaF1_WIE_06_A_06 SEQ ID NO:961, CaF1_WIE_06_C_01 SEQ ID NO:972, CaF1_WIE_08_C_05 SEQ ID NO:1123, CaF1_WIE_08_C_06 SEQ ID NO:1124, CaF1_WIE_08_D_10 SEQ ID NO:1138, CaF1_WIE_08_E_06 SEQ ID NO:1142, CaF1_WIE_08_F_06 SEQ ID NO:1150, CaF1_WIE_08_H_03 SEQ ID NO:1166, CaF1_WIE_09_A_07 SEQ ID NO:1178, CaF1_WIE_09_A_08 SEQ ID NO:1179, CaF1_WIE_09_E_11 SEQ ID NO:1208, CaF1_WIE_09_G_07 SEQ ID NO:1223, CaF1_WIE_12_C_08 SEQ ID NO:3401, CaF1_WIE_12_E_06 SEQ ID NO:3415, CaF1_WIE_13_A_05 SEQ ID NO:3456, CaF1_WIE_13_G_07 SEQ ID NO:3511, CaF1_WIE_18_D_10 SEQ ID NO:3758, CaF1_WIE_19_E_07 SEQ ID NO:3833, CaF1_WIE_19_F_02 SEQ ID NO:3837, CaF1_WIE_21_C_03 SEQ ID NO:3933, CaF1_WIE_21_C_06 SEQ ID NO:3935, CaF1_WIE_21_D_03 SEQ ID NO:3940, CaF1_WIE_21_H_03 SEQ ID NO:3972, CaF1_WIE_21_H_09 SEQ ID NO:3975, CaF1_WIE_22_A_06 SEQ ID NO:3980, CaF1_WIE_23_B_07 SEQ ID NO:4039, CaF1_WIE_24_C_11 SEQ ID NO:4112, CaF1_WIE_24_F_03 SEQ ID NO:4130, CaF1_WIE_24_F_05 SEQ ID NO:4132, CaF1_WIE_24_F_06 SEQ ID NO:4133, CaF1_WIE_24_F_08 SEQ ID NO:4135, CaF1_WIE_24_G_06 SEQ ID NO:4144, CaF1_WIE_24_G_10 SEQ ID NO:4147, CaF1_WIE_25_B_07 SEQ ID NO:4173, CaF1_WIE_25_E_06 SEQ ID NO:4200, CaF1_WIE_25_G_02 SEQ ID NO:4211, CaF1_WIE_26_C_04 SEQ ID NO:4245, CaF1_WIE_26_E_06 SEQ ID NO:4267, CaF1_WIE_27_D_01 SEQ ID NO:4329, CaF1_WIE_29_D_07 SEQ ID NO:4484, CaF1_WIE_29_G_09 SEQ ID NO:4518, CaF1_WIE_29_G_10 SEQ ID NO:4519, CaF1_WIE_31_C_09 SEQ ID NO:4625, CaF1_WIE_31_F_09 SEQ ID NO:4652, CaF1_WIE_32_C_04 SEQ ID NO:4695, CaF1_WIE_32_H_01 SEQ ID NO:4735, CaF1_WIE_33_E_05 SEQ ID NO:4779, CaF1_WIE_33_G_10 SEQ ID NO:4803, CaF1_WIE_33_G_11 SEQ ID NO:4804, CaF1_WIE_33_H_01 SEQ ID NO:4805, CaF1_WIE_33_H_02 SEQ ID NO:4806, CaF1_WIE_33_H_05 SEQ ID NO: 4807, CaF1_WIE_35_G_04 SEQ ID NO:4939, CaF1_WIE_36_C_05 SEQ ID NO:4973, CaF1_WIE_36_C_09 SEQ ID NO:4976, CaF1_WIE_36_C_11 SEQ ID NO:4978, CaF1_WIE_36_H_09 SEQ ID NO:5019, CaF1_WIE_37_B_03 SEQ ID NO:5031, CaF1_WIE_37_E_09 SEQ ID NO:5056, CaF1_WIE_37_H_05 SEQ ID NO:5078, CaF1_WIE_37_H_10 SEQ ID NO:5082, CaF1_WIE_37_H_11 SEQ ID NO:5083, CaF1_WIE_39_G_07 SEQ ID NO:5187, CaF1_WIE_40_B_01 SEQ ID NO:5209, CaF1_WIE_41_C_01 SEQ ID NO:5290, CaF1_WIE_41_C_08 SEQ ID NO:5295, CaF1_WIE_41_F_07 SEQ ID NO:5319, CaF1_WIE_41_G_03 SEQ ID NO:5324, CaF1_WIE_41_H_01 SEQ ID NO:5330, CaF1_WIE_42_H_07 SEQ ID NO:5387, CaF1_WIE_44_E_02 SEQ ID NO:5474, CaF1_WIE_44_E_03 SEQ ID NO:5475, CaF1_WIE_44_E_04 SEQ ID NO:5476, CaF1_WIE_44_F_06 SEQ ID NO:5484, CaF1_WIE_46_G_06 SEQ ID NO:5619, CaF1_WIE_46_H_04 SEQ ID NO:5627, CaF1_WIE_47_C_03 SEQ ID NO:5653, CaF1_WIE_47_E_05 SEQ ID NO:5674, CaF1_WIE_47_G_02 SEQ ID NO:5691, CaF1_WIE_48_C_11 SEQ ID NO:5731, CaF1_WIE_48_F_07 SEQ ID NO:5755, CaF1_WIE_49_B_05 SEQ ID NO:5786, CaF1_WIE_49_G_10 SEQ ID NO:5825, CaF1_WIE_49_H_10 SEQ ID NO:5833, CaF1_WIE_50_B_03 SEQ ID NO:5840, CaF1_WIE_50_G_06 SEQ ID NO:5884, CaF1_WIE_50_G_10 SEQ ID NO:5888, CaF1_WIE_51_A_11 SEQ ID NO:5905, CaF1_WIE_51_C_02 SEQ ID NO:5915, CaF1_WIE_51_C_11 SEQ ID NO:5924, CaF1_WIE_52_F_04 SEQ ID NO:6002, CaF1_WIE_52_H_03 SEQ ID NO:6019, CaF1_WIE_53_A_02 SEQ ID NO:6028, CaF1_WIE_53_B_01 SEQ ID NO:6035, CaF1_WIE_53_H_05 SEQ ID NO:6078, CaF1_WIE_54_C_02 SEQ ID NO:6100, CaF1_WIE_54_C_09 SEQ ID NO:6106, CaF1_WIE_55_B_11 SEQ ID NO:6165 and CaF1_WIE_55_G_01 SEQ ID NO:6199.

In another embodiment the present invention provides ESTs derived from chickpea, wherein the ESTs are related to transcription. These ESTs are CaF1_JIE_01_B_10 SEQ ID NO:19, CaF1_JIE_01_C_05 SEQ ID NO:25, CaF1_JIE_01_E_04 SEQ ID NO:44, CaF1_JIE_01_F_11 SEQ ID NO:58, CaF1_JIE_02_D_03 SEQ ID NO:100, CaF1_JIE_02_D_07 SEQ ID NO:103, CaF1_JIE_02_H_06 SEQ ID NO:138, CaF1_JIE_03_A_02 SEQ ID NO:144, CaF1_JIE_04_B_11 SEQ ID NO:230, CaF1_JIE_04_F_01 SEQ ID NO:259, CaF1_JIE_04_G_10 SEQ ID NO:278, CaF1_JIE_05_E_06 SEQ ID NO:335, CaF1_JIE_06_C_06 SEQ ID NO:392, CaF1_JIE_07_C_04 SEQ ID NO:457, CaF1_JIE_08_A_11 SEQ ID NO:525, CaF1_JIE_11_A_04 SEQ ID NO:1363, CaF1_JIE_11_B_09 SEQ ID NO:1373, CaF1_JIE_12_B_02 SEQ ID NO:1431, CaF1_JIE_12_B_03 SEQ ID NO:1432, CaF1_JIE_12_B_04 SEQ ID NO:1433, CaF1_JIE_12_E_02 SEQ ID NO:1457, CaF1_JIE_12_E_03 SEQ ID NO:1458, CaF1_JIE_12_E_04 SEQ ID NO:1459, CaF1_JIE_14_E_06 SEQ ID NO:1555, CaF1_JIE_15_D_11 SEQ ID NO:1617, CaF1_JIE_15_E_04 SEQ ID NO:1620, CaF1_JIE_15_F_05 SEQ ID NO:1627, CaF1_JIE_16_G_01 SEQ ID NO:1700, CaF1_JIE_17_C_09 SEQ ID NO:1733, CaF1_JIE_17_C_10 SEQ ID NO:1734, CaF1_JIE_17_G_01 SEQ ID NO:1759, CaF1_JIE_17_G_11 SEQ ID NO:1762, CaF1_JIE_17_H_02 SEQ ID NO:1764, CaF1_JIE_18_B_07 SEQ ID NO:1779, CaF1_JIE_19_B_03 SEQ ID NO:1845, CaF1_JIE_19_B_04 SEQ ID NO:1846, CaF1_JIE_19_F_02 SEQ ID NO:1878, CaF1_JIE_20_C_04 SEQ ID NO:1927, CaF1_JIE_20_E_01 SEQ ID NO:1945, CaF1_JIE_21_B_08 SEQ ID NO:2004, CaF1_JIE_21_C_01 SEQ ID NO:2007, CaF1_JIE_21_C_02 SEQ ID NO:2008, CaF1_JIE_21_D_01 SEQ ID NO:2017, CaF1_JIE_21_E_05 SEQ ID NO:2030, CaF1_JIE_21_G_02 SEQ ID NO:2043, CaF1_JIE_22_G_08 SEQ ID NO:2127, CaF1_JIE_24_C_01 SEQ ID NO:2240, CaF1_JIE_24_D_01 SEQ ID NO:2248, CaF1_ME 26_A_111 SEQ ID NO:2354, CaF1_JIE_26_C_10 SEQ ID NO:2370, CaF1_JIE_26_E_10 SEQ ID NO:2387, CaF1_JIE_27_F_10 SEQ ID NO:2456, CaF1_JIE_28_C_10 SEQ ID NO:2487, CaF1_JIE_29_C_11 SEQ ID NO:2539, CaF1_JIE_29_D_11 SEQ ID NO:2545, CaF1_JIE_29_F_06 SEQ ID NO:2552, CaF1_JIE_30_F_06 SEQ ID NO:2598, CaF1_JIE_30_F_07 SEQ ID NO:2599, CaF1_JIE_31_D_03 SEQ ID NO:2637, CaF1_JIE_31_F_02 SEQ ID NO:2650, CaF1_JIE_32_G_05 SEQ ID NO:2712, CaF1_JIE_32_G_06 SEQ ID NO:2713, CaF1_JIE_33_B_09 SEQ ID NO:2737, CaF1_JIE_34_A_11 SEQ ID NO:2787, CaF1_JIE_34_E_02 SEQ ID NO:2811, CaF1_JIE_34_E_03 SEQ ID NO:2812, CaF1_JIE_34_H_03 SEQ ID NO:2830, CaF1_JIE_35_F_07 SEQ ID NO:2877, CaF1_JIE_35_G_01 SEQ ID NO:2879, CaF1_JIE_36_A_09 SEQ ID NO:2897, CaF1_JIE_36_C_03 SEQ ID NO:2908, CaF1_JIE_36_C_09 SEQ ID NO:2910, CaF1_JIE_36_F_05 SEQ ID NO:2931, CaF1_JIE_36_G_01 SEQ ID NO:2936, CaF1_JIE_38_C_09 SEQ ID NO:3018, CaF1_JIE_38_D_02 SEQ ID NO:3020, CaF1_JIE_38_F_04 SEQ ID NO:3037, CaF1_JIE_39_F_01 SEQ ID NO:3090, CaF1_JIE_39_F_03 SEQ ID NO:3092, CaF1_JIE_40_H_07 SEQ ID NO:3177, CaF1_JIE_41_D_04 SEQ ID NO:3204, CaF1_WIE_02_C_04 SEQ ID NO:716, CaF1_WIE_03_A_06 SEQ ID NO:767, CaF1_WIE_03_E_11 SEQ ID NO:798, CaF1_WIE_04_B_03 SEQ ID NO:827, CaF1_WIE_04_B_06 SEQ ID NO:830, CaF1_WIE_04_B_07 SEQ ID NO:831, CaF1_WIE_04_G_07 SEQ ID NO:875, CaF1_WIE_04_G_08 SEQ ID NO:876, CaF1_WIE_05_A_03 SEQ ID NO:889, CaF1_WIE_05_F_04 SEQ ID NO:934, CaF1_WIE_

07_D_10 SEQ ID NO:1062, CaF1_WIE_07_E_11 SEQ ID NO:1072, CaF1_WIE_07_F_05 SEQ ID NO:1077, CaF1_WIE_07_H_04 SEQ ID NO:1096, CaF1_WIE_08_A_11 SEQ ID NO:1108, CaF1_WIE_08_B_11 SEQ ID NO:1118, CaF1_WIE_08_C_11 SEQ ID NO:1128, CaF1_WIE_08_F_09 SEQ ID NO:1153, CaF1_WIE_08_F_11 SEQ ID NO:1155, CaF1_WIE_08_H_04 SEQ ID NO:1167, CaF1_WIE_08_H_05 SEQ ID NO:1168, CaF1_WIE_09_C_11 SEQ ID NO:1191, CaF1_WIE_09_F_08 SEQ ID NO:1216, CaF1_WIE_12_B_03 SEQ ID NO:3386, CaF1_WIE_12_E_10 SEQ ID NO:3419, CaF1_WIE_12_H_05 SEQ ID NO:3446, CaF1_WIE_13_C_11 SEQ ID NO:3478, CaF1_WIE_13_D_02 SEQ ID NO:3480, CaF1_WIE_13_D_03 SEQ ID NO:3481, CaF1_WIE_13_E_01 SEQ ID NO:3487, CaF1_WIE_16_B_05 SEQ ID NO:3606, CaF1_WIE_17_A_01 SEQ ID NO:3644, CaF1_WIE_17_B_02 SEQ ID NO:3656, CaF1_WIE_17_B_09 SEQ ID NO:3662, CaF1_WIE_17_D_10 SEQ ID NO:3682, CaF1_WIE_18_C_07 SEQ ID NO:3747, CaF1_WIE_18_E_08 SEQ ID NO:3766, CaF1_WIE_18_H_03 SEQ ID NO:3791, CaF1_WIE_19_C_08 SEQ ID NO:3820, CaF1_WIE_19_F_04 SEQ ID NO:3839, CaF1_WIE_19_H_01 SEQ ID NO:3853, CaF1_WIE_19_H_04 SEQ ID NO:3855, CaF1_WIE_19_H_07 SEQ ID NO:3858, CaF1_WIE_21_G_01 SEQ ID NO:3960, CaF1_WIE_21_H_08 SEQ ID NO:3974, CaF1_WIE_23_H_10 SEQ ID NO:4086, CaF1_WIE_24_C_08 SEQ ID NO:4109, CaF1_WIE_24_G_03 SEQ ID NO:4141, CaF1_WIE_25_C_10 SEQ ID NO:4184, CaF1_WIE_26_A_11 SEQ ID NO:4232, CaF1_WIE_26_C_02 SEQ ID NO:4243, CaF1_WIE_27_A_03 SEQ ID NO:4301, CaF1_WIE_27_E_08 SEQ ID NO:4344, CaF1_WIE_27_F_05 SEQ ID NO:4352, CaF1_WIE_27_G_04 SEQ ID NO:4362, CaF1_WIE_27_G_05 SEQ ID NO:4363, CaF1_WIE_28_C_08 SEQ ID NO:4400, CaF1_WIE_29_C_10 SEQ ID NO:4476, CaF1_WIE_29_G_06 SEQ ID NO:4515, CaF1_WIE_30_B_08 SEQ ID NO:4544, CaF1_WIE_30_E_03 SEQ ID NO:4567, CaF1_WIE_30_E_09 SEQ ID NO:4572, CaF1_WIE_30_F_09 SEQ ID NO:4581, CaF1_WIE_30_G_08 SEQ ID NO:4591, CaF1_WIE_30_H_09 SEQ ID NO:4599, CaF1_WIE_31_F_11 SEQ ID NO:4654, CaF1_WIE_32_E_05 SEQ ID NO:4710, CaF1_WIE_33_A_03 SEQ ID NO:4748, CaF1_WIE_33_C_09 SEQ ID NO:4768, CaF1_WIE_33_F_08 SEQ ID NO:4791, CaF1_WIE_34_A_11 SEQ ID NO:4819, CaF1_WIE_34_D_01 SEQ ID NO:4836, CaF1_WIE_34_F_11 SEQ ID NO:4861, CaF1_WIE_37_A_10 SEQ ID NO:5028, CaF1_WIE_38_H_03 SEQ ID NO:5139, CaF1_WIE_39_B_01 SEQ ID NO:5153, CaF1_WIE_39_C_01 SEQ ID NO:5161, CaF1_WIE_39_G_02 SEQ ID NO:5183, CaF1_WIE_39_H_04 SEQ ID NO:5192, CaF1_WIE_39_H_07 SEQ ID NO:5195, CaF1_WIE_40_C_09 SEQ ID NO:5224, CaF1_WIE_40_D_05 SEQ ID NO:5229, CaF1_WIE_41_H_07 SEQ ID NO:5336, CaF1_WIE_41_H_11 SEQ ID NO:5340, CaF1_WIE_44_H_07 SEQ ID NO:5498, CaF1_WIE_45_A_02 SEQ ID NO:5502, CaF1_WIE_45_A_03 SEQ ID NO:5503, CaF1_WIE_45_E_07 SEQ ID NO:5534, CaF1_WIE_45_F_04 SEQ ID NO:5540, CaF1_WIE_46_E_02 SEQ ID NO:5600, CaF1_WIE_46_F_07 SEQ ID NO:5613, CaF1_WIE_47_G_08 SEQ ID NO:5697, CaF1_WIE_49_B_01 SEQ ID NO:5783, CaF1_WIE_49_C_09 SEQ ID NO:5798, CaF1_WIE_50_D_04 SEQ ID NO:5858, CaF1_WIE_51_F_10 SEQ ID NO:5946, CaF1_WIE_52_E_04 SEQ ID NO:5994, CaF1_WIE_52_E_05 SEQ ID NO:5995, CaF1_WIE_52_G_02 SEQ ID NO:6009, CaF1_WIE_52_G_11 SEQ ID NO:6017, CaF1_WIE_52_H_09 SEQ ID NO:6025, CaF1_WIE_53_F_03 SEQ ID NO:6067, CaF1_WIE_54_A_01 SEQ ID NO:6081, SEQ ID NO:6211 and CaF1_WIE_56_C_04 SEQ ID NO:6234.

In another embodiment the present invention provides ESTs derived from chickpea, wherein the ESTs are related to RNA processing and modification. These ESTs are CaF1_JIE_02_A_10 SEQ ID NO:78, CaF1_JIE_02_B_07 SEQ ID NO:85, CaF1_JIE_02_C_02 SEQ ID NO:89, CaF1_JIE_03_C_03 SEQ ID NO:159, CaF1_JIE_03_H_02 SEQ ID NO:203, CaF1_JIE_04_B_01 SEQ ID NO:220, CaF1_JIE_06_G_09 SEQ ID NO:428, CaF1_JIE_09_C_11 SEQ ID NO:626, CaF1_JIE_12_D_06 SEQ ID NO:1452, CaF1_JIE_14_B_10 SEQ ID NO:1534, CaF1_JIE_14_C_10 SEQ ID NO:1543, CaF1_JIE_16_B_02 SEQ ID NO:1658, CaF1_JIE_16_B_03 SEQ ID NO:1659, CaF1_JIE_16_D_04 SEQ ID NO:1678, CaF1_JIE_16_F_02 SEQ ID NO:1693, CaF1_JIE_17_C_07 SEQ ID NO:1731, CaF1_JIE_18_D_11 SEQ ID NO:1801, CaF1_JIE_19_B_01 SEQ ID NO:1844, CaF1_JIE_21_C_03 SEQ ID NO:2009, CaF1_JIE_21_C_11 SEQ ID NO:2016, CaF1_JIE_22_A_02 SEQ ID NO:2062, CaF1_JIE_22_B_03 SEQ ID NO:2074, CaF1_JIE_26_E_05 SEQ ID NO:2384, CaF1_JIE_26_E_07 SEQ ID NO:2386, CaF1_JIE_28_F_10 SEQ ID NO:2507, CaF1_JIE_28_F_11 SEQ ID NO:2508, CaF1_JIE_30_A_10 SEQ ID NO:2575, CaF1_JIE_31_F_01 SEQ ID NO:2649, CaF1_JIE_32_B_03 SEQ ID NO:2680, CaF1_JIE_36_C_01 SEQ ID NO:2906, CaF1_JIE_37_D_05 SEQ ID NO:2967, CaF1_JIE_38_D_05 SEQ ID NO:3023, CaF1_JIE_38_E_07 SEQ ID NO:3032, CaF1_JIE_38_F_07 SEQ ID NO:3039, CaF1_JIE_38_G_07 SEQ ID NO:3046, CaF1_JIE_40_E_03 SEQ ID NO:3148, CaF1_JIE_40_H_08 SEQ ID NO:3178, CaF1_JIE_41_F_01 SEQ ID NO:3220, CaF1_WIE_01_C_06 SEQ ID NO:650, CaF1_WIE_01_D_06 SEQ ID NO:659, CaF1_WIE_02_E_11 SEQ ID NO:738, CaF1_WIE_05_A_05 SEQ ID NO:891, CaF1_WIE_06_F_08 SEQ ID NO:1002, CaF1_WIE_07_E_01 SEQ ID NO:1064, CaF1_WIE_07_G_03 SEQ ID NO:1086, CaF1_WIE_08_B_04 SEQ ID NO:1111, CaF1_WIE_10_C_04 SEQ ID NO:1254, CaF1_WIE_10_H_11 SEQ ID NO:3307, CaF1_WIE_11_G_10 SEQ ID NO:3367, CaF1_WIE_12_C_03 SEQ ID NO:3396, CaF1_WIE_13_B_08 SEQ ID NO:3465, CaF1_WIE_14_A_01 SEQ ID NO:3524, CaF1_WIE_15_G_03 SEQ ID NO:3591, CaF1_WIE_15_H_11 SEQ ID NO:3599, CaF1_WIE_17_C_01 SEQ ID NO:3665, CaF1_WIE_18_F_02 SEQ ID NO:3771, CaF1_WIE_19_C_11 SEQ ID NO:3822, CaF1_WIE_20_A_04 SEQ ID NO:3864, CaF1_WIE_20_C_10 SEQ ID NO:3876, CaF1_WIE_21_A_06 SEQ ID NO:3919, CaF1_WIE_21_F_04 SEQ ID NO:3955, CaF1_WIE_21_H_04 SEQ ID NO:3973, CaF1_WIE_22_D_09 SEQ ID NO:4000, CaF1_WIE_23_D_09 SEQ ID NO:4051, CaF1_WIE_26_A_08 SEQ ID NO:4230, CaF1_WIE_26_D_11 SEQ ID NO:4261, CaF1_WIE_26_E_104 SEQ ID NO:4265, CaF1_WIE_26_E_05 SEQ ID NO:4266, CaF1_WIE_26_E_07 SEQ ID NO:4268, CaF1_WIE_27_F_09 SEQ ID NO:4356, CaF1_WIE_27_F_10 SEQ ID NO:4357, CaF1_WIE_27_G_10 SEQ ID NO:4368, CaF1_WIE_27_H_10 SEQ ID NO:4377, CaF1_WIE_28_D_09 SEQ ID NO:4410, CaF1_WIE_28_H_02 SEQ ID NO:4437, CaF1_WIE_28_H_08 SEQ ID NO:4442, CaF1_WIE_29_A_11 SEQ ID NO:4455, CaF1_WIE_29_B_06 SEQ ID NO:4461, CaF1_WIE_29_B_11 SEQ ID NO:4466, CaF1_WIE_29_C_08 SEQ ID NO:4474, CaF1_WIE_29_F_03 SEQ ID NO:4501, CaF1_WIE_29_F_10 SEQ ID NO:4508, CaF1_WIE_29_G_11 SEQ ID NO:4520, CaF1_WIE_31_B_11 SEQ ID NO:4619, CaF1_WIE_31_E_02 SEQ ID NO:4637, CaF1_WIE_32_H_11 SEQ ID NO:4745, CaF1_WIE_34_E_05 SEQ ID NO:4848, CaF1_WIE_34_G_06 SEQ ID NO:4866, CaF1_WIE_35_D_11 SEQ ID NO:4916, CaF1_WIE_35_E_07 SEQ ID NO:4922, CaF1_WIE_35_G_05 SEQ ID NO:4940, CaF1_WIE_37_B_06 SEQ ID NO:5033, CaF1_WIE_37_B_09 SEQ ID NO:5036, CaF1_WIE_37_F_03 SEQ ID NO:5059, CaF1_WIE_40_H_03 SEQ ID NO:5265, CaF1_WIE_41_E_03 SEQ ID NO:5308, CaF1_WIE_41_G_01 SEQ ID NO:5322, CaF1_WIE_41_G_02 SEQ ID NO:5323, CaF1_WIE_42_E_03 SEQ ID NO:5368, CaF1_WIE_42_F_05 SEQ ID NO:5374, CaF1_WIE_42_F_10 SEQ ID NO:5378, CaF1_WIE_42_G_03 SEQ ID NO:5381, CaF1_WIE_42_H_05 SEQ ID NO:5386, CaF1_WIE_43_A_02 SEQ ID NO:5389, CaF1_WIE_43_A_03 SEQ ID NO:5390, CaF1_WIE_43_F_03 SEQ ID NO:5427, CaF1_WIE_43_F_05 SEQ ID NO:5429, CaF1_WIE_43_F_10 SEQ ID NO:5431, CaF1_WIE_45_G_04 SEQ ID NO:5546, CaF1_WIE_45_H_02 SEQ ID NO:5554, CaF1_WIE_45_H_07 SEQ ID NO:5559, CaF1_WIE_46_G_08 SEQ ID NO:5621, CaF1_WIE_48_H_11 SEQ ID NO:5774, CaF1_WIE_50_C_02 SEQ ID NO:5850, CaF1_WIE_50_E_06 SEQ ID NO:5870, CaF1_WIE_50_H_01 SEQ ID NO:5890, CaF1_WIE_51_A_03 SEQ ID NO:5897, CaF1_WIE_51_A_09 SEQ ID NO:5903, CaF1_WIE_52_B_03 SEQ ID NO:5967, CaF1_WIE_52_F_06 SEQ ID NO:6004, CaF1_WIE_52_G_07 SEQ ID NO:6013, CaF1_WIE_53_D_04 SEQ ID NO:6052, CaF1_WIE_55_C_11 SEQ ID NO:6174 and CaF1_WIE_55_E_11 SEQ ID NO:6190.

Genes Involved in Translation, Post Translational Modifications and Protein Turnover Cellular processes like translation, post translational event and protein turnover are crucial for cell survival under different developmental stages and varied environmental conditions.

In the present study, this class constituted about 8.84% of ESTs and comprised predominantly the ribosomal proteins apart from some translation initiation factors. Genes encoding major ribosomal proteins such as S6, S8, S9, and L24/L26 were found both in susceptible and resistant genotypes. Translation factor SUI1 homolog and eukaryotic elongation factors (EF-1α and EF-2) play a pivotal role in protein biosynthesis. Their presence in CaUnigene set is indicative of their role in immune response.

A particularly sensitive, rapid and reversible response to environmental stimuli or to a programmatic change in cell state is the post-translational modification of specific proteins. In our study, 4.27% of the CaUnigenes correspond to proteins involved in protein modifications and turnover. The presence of cysteine proteinases and cyclophilin-type peptidyl-prolyl cis-trans isomerases more predominantly in resistant genotype indicate their role in pathostress responses. The presence of heat shock protein, DnaJ is interesting as it has been shown to be involved in different environmental stresses including high temperature and salinity treatment. Our results revealed the presence of a wide range of proteins involved in protein turnover that include ubiquitin conjugating enzyme E2, ubiquitin-protein ligase, 20S proteasome alpha 6 subunit, F-box protein and protein disulphide in both the genotypes. In plants, ubiquitin/proteasome pathway of protein degradation has been implicated in defense. These results suggest that regulated protein synthesis, modification and protein turnover may play central role in enabling plants to alter their proteome to maximize their chances of survival under adverse conditions.

In yet another embodiment the present invention provides ESTs derived from chickpea, wherein the ESTs are related to translation, ribosomal structure and biogenesis. These ESTs are CaF1_JIE_01_A_04 SEQ ID NO:3, CaF1_JIE_01_B_09 SEQ ID NO:18, CaF1_JIE_01_C_01 SEQ ID NO:21, CaF1_JIE_01_C_03 SEQ ID NO:23, CaF1_JIE_01_D_04 SEQ ID NO:35, CaF1_JIE_01_F_7 SEQ ID NO:55, CaF1_JIE_01_G_03 SEQ ID NO:60, CaF1_JIE_01_H_07 SEQ ID NO:69, CaF1_JIE_02_B_01 SEQ ID NO:80, CaF1_JIE_02_B_02 SEQ ID NO:81, CaF1_JIE_02_G_01 SEQ ID NO:124, CaF1_JIE_02_G_02 SEQ ID NO:125, CaF1_JIE_02_H_10 SEQ ID NO:141, CaF1_JIE_03_C_04 SEQ ID NO:160, CaF1_JIE_03_F_05 SEQ ID NO:187, CaF1_JIE_03_F_09 SEQ ID NO:191, CaF1_JIE_03_G_07 SEQ ID NO:198, CaF1_JIE_03_H_03 SEQ ID NO:204, CaF1_JIE_03_H_04 SEQ ID NO:205, CaF1_JIE_04_A_06 SEQ ID NO:214, CaF1_JIE_04_B_03 SEQ ID NO:222, CaF1_JIE_04_B_04 SEQ ID NO:223, CaF1_JIE_04_C_04 SEQ ID NO:234, CaF1_JIE_05_B_09 SEQ ID NO:307, CaF1_JIE_05_B_11 SEQ ID NO:309, CaF1_JIE_05_F_03 SEQ ID NO:343, CaF1_JIE_05_H_05 SEQ ID NO:364, CaF1_JIE_05_H_06 SEQ ID NO:365, CaF1_JIE_05_H_11 SEQ ID NO:370, CaF1_JIE_06_A_05 SEQ ID NO:374, CaF1_JIE_06_A_07 SEQ ID NO:376, CaF1_JIE_06_E_07 SEQ ID NO:407, CaF1_JIE_06_G_01 SEQ ID NO:421, CaF1_JIE_06_G_03 SEQ ID NO:423, CaF1_JIE_06_G_06 SEQ ID NO:426, CaF1_JIE_06_G_07 SEQ ID NO:427, CaF1_JIE_07_A_03 SEQ ID NO:438, CaF1_JIE_07_B_07 SEQ ID NO:450, CaF1_JIE_07_C_09 SEQ ID NO:462, CaF1_JIE_07_D_09 SEQ ID NO:473, CaF1_JIE_07_E_09 SEQ ID NO:482, CaF1_JIE_07_E_10 SEQ ID NO:483, CaF1_JIE_07_H_03 SEQ ID NO:507, CaF1_JIE_09_B_06 SEQ ID NO:613, CaF1_JIE_09_D_03 SEQ ID NO:629, CaF1_JIE_09_D_07 SEQ ID NO:1276, CaF1_JIE_09_H_07 SEQ ID NO:1314, CaF1_JIE_10_B_07 SEQ ID NO:1329, CaF1_JIE_10_B_08 SEQ ID NO:1330, CaF1_JIE_11_E_07 SEQ ID NO:1397, CaF1_JIE_12_B_09 SEQ ID NO:1438, CaF1_JIE_14_F_03 SEQ ID NO:1561, CaF1_JIE_14_F_04 SEQ ID NO:1562, CaF1_JIE_14_G_11 SEQ ID NO:1574, CaF1_JIE_16_C_11 SEQ ID NO:1675, CaF1_JIE_16_G_09 SEQ ID NO:1706, CaF1_JIE_17_D_04 SEQ ID NO:1739, CaF1_JIE_17_E_09 SEQ ID NO:1749, CaF1_JIE_17_E_10 SEQ ID NO:1750, CaF1_JIE_17_F_09 SEQ ID NO:1756, CaF1_JIE_17_F_10 SEQ ID NO:1757, CaF1_JIE_17_F_11 SEQ ID NO:1758, CaF1_JIE_18_B_02 SEQ ID NO:1777, CaF1_JIE_18_C_11 SEQ ID NO:1793, CaF1_JIE_18_D_01 SEQ ID NO:1794, CaF1_JIE_18_D_02 SEQ ID NO:1795, CaF1_JIE_18_E_01 SEQ ID NO:1802, CaF1_JIE_18_E_02 SEQ ID NO:1803, CaF1_JIE_18_F_09 SEQ ID NO:1818, CaF1_JIE_18_F_10 SEQ ID NO:1819, CaF1_JIE_18_H_02 SEQ ID NO:1830, CaF1_JIE_20_B_10 SEQ ID NO:1922, CaF1_JIE_20_C_06 SEQ ID NO:1929, CaF1_JIE_20_D_04 SEQ ID NO:1937, CaF1_JIE_20_E_04 SEQ ID NO:1948, CaF1_JIE_20_F_09 SEQ ID NO:1963, CaF1_JIE_20_G_07 SEQ ID NO:1971, CaF1_JIE_20_H_04 SEQ ID NO:1979, CaF1_JIE_21_B_05 SEQ ID NO:2001, CaF1_JIE_21_B_06 SEQ ID NO:2002, CaF1_JIE_21_E_07 SEQ ID NO:2031, CaF1_JIE_21_F_04 SEQ ID NO:2036, CaF1_JIE_21_G_06 SEQ ID NO:2047, CaF1_JIE_23_A_02 SEQ ID NO:2142, CaF1_JIE_23_E_04 SEQ ID NO:2182, CaF1_JIE_23_F_04 SEQ ID NO:2192, CaF1_JIE_24_A_

02 SEQ ID NO:2221, CaF1_JIE_24_F_08 SEQ ID NO:2271, CaF1_JIE_24_H_09 SEQ ID NO:2289, CaF1_JIE_25_A_04 SEQ ID NO:2293, CaF1_JIE_25_B_03 SEQ ID NO:2299, CaF1_JIE_25_C_01 SEQ ID NO:2304, CaF1_JIE_25_D_09 SEQ ID NO:2316, CaF1_JIE_25_F_01 SEQ ID NO:2325, CaF1_JIE_25_F_08 SEQ ID NO:2330, CaF1_JIE_25_H_10 SEQ ID NO:2345, CaF1_JIE_27_F_01 SEQ ID NO:2448, CaF1_JIE_29_E_11 SEQ ID NO:2551, CaF1_JIE_30_A_07 SEQ ID NO:2573, CaF1_JIE_30_E_07 SEQ ID NO:2593, CaF1_JIE_31_C_03 SEQ ID NO:2632, CaF1_JIE_31_G_03 SEQ ID NO:2660, CaF1_JIE_33_H_02 SEQ ID NO:2773, CaF1_JIE_33_H_05 SEQ ID NO:2776, CaF1_JIE_34_D_05 SEQ ID NO:2806, CaF1_JIE_34_D_07 SEQ ID NO:2807, CaF1_JIE_34_D_10 SEQ ID NO:2809, CaF1_JIE_36_H_11 SEQ ID NO:2947, CaF1_JIE_37_C_05 SEQ ID NO:2961, CaF1_JIE_37_H_07 SEQ ID NO:2994, CaF1_JIE_38_D_06 SEQ ID NO:3024, CaF1_JIE_38_E_08 SEQ ID NO:3033, CaF1_JIE_38_G_11 SEQ ID NO:3050, CaF1_JIE_39_D_04 SEQ ID NO:3079, CaF1_JIE_40_D_02 SEQ ID NO:3140, CaF1_JIE_40_F_09 SEQ ID NO:3160, CaF1_JIE_41_D_11 SEQ ID NO:3210, CaF1_JIE_42_G_03 SEQ ID NO:3267, CaF1_WIE_01_F_10 SEQ ID NO:679, CaF1_WIE_01_G_03 SEQ ID NO:683, CaF1_WIE_02_F_05 SEQ ID NO:742, CaF1_WIE_02_H_10 SEQ ID NO:761, CaF1_WIE_03_B_09 SEQ ID NO:773, CaF1_WIE_03_C_02 SEQ ID NO:776, CaF1_WIE_03_G_09 SEQ ID NO:808, CaF1_WIE_03_G_10 SEQ ID NO:809, CaF1_WIE_04_C_08 SEQ ID NO:842, CaF1_WIE_04_E_10 3 SEQ ID NO:854, CaF1_WIE_04_F_11 SEQ ID NO:871, CaF1_WIE_04_H_10 SEQ ID NO:886, CaF1_WIE_04_H_11 SEQ ID NO:887, CaF1_WIE_05_H_08 SEQ ID NO:954, CaF1_WIE_06_D_02 SEQ ID NO:980, CaF1_WIE_06_E_07 SEQ ID NO:992, CaF1_WIE_06_H_05 SEQ ID NO:1018, CaF1_WIE_06_H_06 SEQ ID NO:1019, CaF1_WIE_06_H_11 SEQ ID NO:1024, CaF1_WIE_07_B_05 SEQ ID NO:1038, CaF1_WIE_07_B_09 SEQ ID NO:1042, CaF1_WIE_07_C_01 SEQ ID NO:1045, CaF1_WIE_07_C_09 SEQ ID NO:1051, CaF1_WIE_07_E_06 SEQ ID NO:1068, CaF1_WIE_07_F_08 SEQ ID NO:1080, CaF1_WIE_07_G_02 SEQ ID NO:1085, CaF1_WIE_07_G_06 SEQ ID NO:1089, CaF1_WIE_07_H_01 SEQ ID NO:1094, CaF1_WIE_07_H_10 SEQ ID NO:1101, CaF1_WIE_08_C_08 SEQ ID NO:1126, CaF1_WIE_08_F_08 SEQ ID NO:1152, CaF1_WIE_09_C_10 SEQ ID NO:1190, CaF1_WIE_09_E_03 SEQ ID NO:1200, CaF1_WIE_09_E_08 SEQ ID NO:1205, CaF1_WIE_09_E_09 SEQ ID NO:1206, CaF1_WIE_09_F_06 SEQ ID NO:1214, CaF1_WIE_09_G_02 SEQ ID NO:1218, CaF1_WIE_09_G_04 SEQ ID NO:1220, CaF1_WIE_09_H_04 SEQ ID NO:1227, CaF1_WIE_10_A_01 SEQ ID NO:1234, CaF1_WIE_10_C_05 SEQ ID NO:1255, CaF1_WIE_10_H_09 SEQ ID NO:3305, CaF1_WIE_11_A_06 SEQ ID NO:3312, CaF1_WIE_11_C_04 SEQ ID NO:3328, CaF1_WIE_11_F_07 SEQ ID NO:3355, CaF1_WIE_11_G_01 SEQ ID NO:3360, CaF1_WIE_11_H_10 SEQ ID NO:3375, CaF1_WIE_12_A_04 SEQ ID NO:3379, CaF1_WIE_12_B_07 SEQ ID NO:3390, CaF1_WIE_12_B_10 SEQ ID NO:3393, CaF1_WIE_12_D_05 SEQ ID NO:3407, CaF1_WIE_12_E_11 SEQ ID NO:3420, CaF1_WIE_12_G_04 SEQ ID NO:3434, CaF1_WIE_12_H_08 SEQ ID NO:3448, CaF1_WIE_13_D_05 SEQ ID NO:3482, CaF1_WIE_13_E_02 SEQ ID NO:3488, CaF1_WIE_13_E_05 SEQ ID NO:3491, CaF1_WIE_13_E_10 SEQ ID NO:3495, CaF1_WIE_13_F_02 SEQ ID NO:3498, CaF1_WIE_13_F_10 SEQ ID NO:3504, CaF1_WIE_13_G_03 SEQ ID NO:3507, CaF1_WIE_13_G_08 SEQ ID NO:3512, CaF1_WIE_14_C_02 SEQ ID NO:3531, CaF1_WIE_14_G_01 SEQ ID NO:3551, CaF1_WIE_14_G_08 SEQ ID NO:3555, CaF1_WIE_14_H_11 SEQ ID NO:3561, CaF1_WIE_16_C_10 SEQ ID NO:3615, CaF1_WIE_16_D_09 SEQ ID NO:3618, CaF1_WIE_16_G_03 SEQ ID NO:3631, CaF1_WIE_16_G_11 SEQ ID NO:3636, CaF1_WIE_17_A_02 SEQ ID NO:3645, CaF1_WIE_17_A_08 SEQ ID NO:3651, CaF1_WIE_17_B_08 SEQ ID NO:3661, CaF1_WIE_17_E_04 SEQ ID NO:3687, CaF1_WIE_18_C_05 SEQ ID NO:3745, CaF1_WIE_18_D_08 SEQ ID NO:3756, CaF1_WIE_18_D_09 SEQ ID NO:3757, CaF1_WIE_18_E_02 SEQ ID NO:3761, CaF1_WIE_18_E_05 SEQ ID NO:3763, CaF1_WIE_18_F_01 SEQ ID NO:3770, CaF1_WIE_18_G_02 SEQ ID NO:3781, CaF1_WIE_19_A_08 SEQ ID NO:3802, CaF1_WIE_19_F_10 SEQ ID NO:3845, CaF1_WIE_19_F_11 SEQ ID NO:3846, CaF1_WIE_20_B_06 SEQ ID NO:3868, CaF1_WIE_20_E_06 SEQ ID NO:3888, CaF1_WIE_21_C_01 SEQ ID NO:3931, CaF1_WIE_21_C_02 SEQ ID NO:3932, CaF1_WIE_21_F_09 SEQ ID NO:3957, CaF1_WIE_22_F_06 SEQ ID NO:4011, CaF1_WIE_23_A_10 SEQ ID NO:4035, CaF1_WIE_23_C_09 SEQ ID NO:4045, CaF1_WIE_24_C_09 SEQ ID NO:4110, CaF1_WIE_24_D_08 SEQ ID NO:4119, CaF1_WIE_24_E_09 SEQ ID NO:4126, CaF1_WIE_24_G_05 SEQ ID NO:4143, CaF1_WIE_24_H_02 SEQ ID NO:4150, CaF1_WIE_24_H_05 SEQ ID NO:4153, CaF1_WIE_25_A_03 SEQ ID NO:4160, CaF1_WIE_25_C_11 SEQ ID NO:4185, CaF1_WIE_25_D_03 SEQ ID NO:4187, CaF1_WIE_25_D_09 SEQ ID NO:4193, CaF1_WIE_25_H_10 SEQ ID NO:4222, CaF1_WIE_26_B_09 SEQ ID NO:4239, CaF1_WIE_26_B_10 SEQ ID NO:4240, CaF1_WIE_26_C_01 SEQ ID NO:4242, CaF1_WIE_26_C_11 SEQ ID NO:4251, CaF1_WIE_26_D_09 SEQ ID NO:4259, CaF1_WIE_26_G_03 SEQ ID NO:4279, CaF1_WIE_26_G_06 SEQ ID NO:4282, CaF1_WIE_26_H_10 SEQ ID NO:4297, CaF1_WIE_27_C_01 SEQ ID NO:4320, CaF1_WIE_27_E_10 SEQ ID NO:4346, CaF1_WIE_27_F_04 SEQ ID NO:4351, CaF1_WIE_27_G_07 SEQ ID NO:4365, CaF1_WIE_27_H_02 SEQ ID NO:4371, CaF1_WIE_28_A_05 SEQ ID NO:4381, CaF1_WIE_28_B_01 SEQ ID NO:4387, CaF1_WIE_28_D_02 SEQ ID NO:4404, CaF1_WIE_28_E_02 SEQ ID NO:4413, CaF1_WIE_29_A_10 SEQ ID NO:4454, CaF1_WIE_29_B_03 SEQ ID NO:4458, CaF1_WIE_29_B_04 SEQ ID NO:4459, CaF1_WIE_29_F_01 SEQ ID NO:4499, CaF1_WIE_29_G_07 SEQ ID NO:4516, CaF1_WIE_30_C_04 SEQ ID NO:4550, CaF1_WIE_30_E_08 SEQ ID NO:4571, CaF1_WIE_30_F_10 SEQ ID NO:4582, CaF1_WIE_30_H_08 SEQ ID NO:4598, CaF1_WIE_31_B_01 SEQ ID NO:4611, CaF1_WIE_31_E_01 SEQ ID NO:4636, CaF1_WIE_31_F_01 SEQ ID NO:4645, CaF1_WIE_31_G_02 SEQ ID NO:4655, CaF1_WIE_32_B_11 SEQ ID NO:4691, CaF1_WIE_32_E_04 SEQ ID NO:4709, CaF1_WIE_33_D_07 SEQ ID NO:4773, CaF1_WIE_34_A_04 SEQ ID NO:4813, CaF1_WIE_34_F_09 SEQ ID NO:4859, CaF1_WIE_34_H_04 SEQ ID NO:4872, CaF1_WIE_35_A_03 SEQ ID NO:4879, CaF1_WIE_35_B_04 SEQ ID NO:4890, CaF1_WIE_35_B_06 SEQ ID NO:4892, CaF1_WIE_35_D_08 SEQ ID NO:4913, CaF1_WIE_35_D_09 SEQ ID NO:4914, CaF1_WIE_36_C_08 SEQ ID NO:4975, CaF1_WIE_36_G_01 SEQ ID NO:5002, CaF1_WIE_36_H_02 SEQ ID NO:5012,

CaF1_WIE_38_A_08 SEQ ID NO:5090, CaF1_WIE_38_B_09 SEQ ID NO:5098, CaF1_WIE_38_C_08 SEQ ID NO:5106, CaF1_WIE_38_C_10 SEQ ID NO:5108, CaF1_WIE_38_D_08 SEQ ID NO:5113, CaF1_WIE_38_F_09 SEQ ID NO:5128, CaF1_WIE_38_G_01 SEQ ID NO:5130, CaF1_WIE_38_G_10 SEQ ID NO:5135, CaF1_WIE_39_D_05 SEQ ID NO:5172, CaF1_WIE_39_G_03 SEQ ID NO:5184, CaF1_WIE_39_H_06 SEQ ID NO:5194, CaF1_WIE_40_A_01 SEQ ID NO:5198, CaF1_WIE_40_A_02 SEQ ID NO:5199, CaF1_WIE_40_B_03 SEQ ID NO:5211, CaF1_WIE_40_E_03 SEQ ID NO:5236, CaF1_WIE_40_F_03 SEQ ID NO:5246, CaF1_WIE_40_F_08 SEQ ID NO:5250, CaF1_WIE_40_F_10 SEQ ID NO:5252, CaF1_WIE_40_H_09 SEQ ID NO:5270, CaF1_WIE_40_H_10 SEQ ID NO:5271, CaF1_WIE_41_B_07 SEQ ID NO:5285, CaF1_WIE_41_B_08 SEQ ID NO:5286, CaF1_WIE_41_D_06 SEQ ID NO:5301, CaF1_WIE_41_D_10 SEQ ID NO:5304, CaF1_WIE_41_F_09 SEQ ID NO:5320, CaF1_WIE_41_H_09 SEQ ID NO:5338, CaF1_WIE_42_A_05 SEQ ID NO:5344, CaF1_WIE_42_A_10 SEQ ID NO:5347, CaF1_WIE_42_C_05 SEQ ID NO:5355, CaF1_WIE_42_C_06 SEQ ID NO:5356, CaF1_WIE_42_C_09. SEQ ID NO:5358, CaF1_WIE_42_F_04 SEQ ID NO:5373, CaF1_WIE_43_B_04 SEQ ID NO:5400, CaF1_WIE_43_C_04 SEQ ID NO:5407, CaF1_WIE_43_G_02 SEQ ID NO:5433, CaF1_WIE_43_G_06 SEQ ID NO:5435, CaF1_WIE_44_A_05 SEQ ID NO:5444, CaF1_WIE_44_C_06 SEQ ID NO:5459, CaF1_WIE_44_G_09 SEQ ID NO:5492, CaF1_WIE_45_B_09 SEQ ID NO:5516, CaF1_WIE_45_C_10 SEQ ID NO:5524, CaF1_WIE_45_D_05 SEQ ID NO:5526, CaF1_WIE_45_F_07 SEQ ID NO:5543, CaF1_WIE_45_G_07 SEQ ID NO:5549, CaF1_WIE_46_B_06 SEQ ID NO:5576, CaF1_WIE_46_C_09 SEQ ID NO:5588, CaF1_WIE_46_D_03 SEQ ID NO:5592, CaF1_WIE_47_D_09 SEQ ID NO:5667, CaF1_WIE_47_E_11 SEQ ID NO:5679, CaF1_WIE_47_F_05 SEQ ID NO:5684, CaF1_WIE_47_G_04 SEQ ID NO:5693, CaF1_WIE_47_H_02 SEQ ID NO:5702, CaF1_WIE_48_A_08 SEQ ID NO:5713, CaF1_WIE_48_A_09 SEQ ID NO:5714, CaF1_WIE_48_C_08 SEQ ID NO:5728, CaF1_WIE_48_C_09 SEQ ID NO:5729, CaF1_WIE_48_E_04 SEQ ID NO:5743, CaF1_WIE_48_G_07 SEQ ID NO:5762, CaF1_WIE_49_B_04 SEQ ID NO:5785, CaF1_WIE_49_H_06 SEQ ID NO:5829, CaF1_WIE_50_A_02 SEQ ID NO:5834, CaF1_WIE_50_B_04 SEQ ID NO:5841, CaF1_WIE_50_C_03 SEQ ID NO:5851, CaF1_WIE_50_C_06 SEQ ID NO:5853, CaF1_WIE_50_D_08 SEQ ID NO:5862, CaF1_WIE_50_E_03 SEQ ID NO:5867, CaF1_WIE_50_F_05 SEQ ID NO:5877, CaF1_WIE_51_C_09 SEQ ID NO:5922, CaF1_WIE_51_H_05 SEQ ID NO:5953, CaF1_WIE_51_H_06 SEQ ID NO:5954, CaF1_WIE_52_A_07 SEQ ID NO:5961, CaF1_WIE_52_B_05 SEQ ID NO:5969, CaF1_WIE_53_A_10 SEQ ID NO:6034, CaF1_WIE_53_F_02 SEQ ID NO:6066, CaF1_WIE_53_F_05 SEQ ID NO:6069, CaF1_WIE_53_F_07 SEQ ID NO:6071, CaF1_WIE_53_G_02 SEQ ID NO:6075, CaF1_WIE_54_B_09 SEQ ID NO:6097, CaF1_WIE_54_D_03 SEQ ID NO:6111, CaF1_WIE_55_D_04 SEQ ID NO:6178, CaF1_WIE_56_A_02 SEQ ID NO:6219, CaF1_WIE_56_A_06 SEQ ID NO:6222, CaF1_WIE_56_B_01 SEQ ID NO:6227, CaF1_WIE_56_E_07 SEQ ID NO:6247, CaF1_WIE_56_F_03 SEQ ID NO:6251, CaF1_WIE_56_H_10 SEQ ID NO:6271 and CaF1_WIE_56_H_11 SEQ ID NO:6272.

Another embodiment of the present invention provides ESTs derived from chickpea, wherein the ESTs are related to post translational modification, protein turn over and chaperons. These ESTs are CaF1_JIE_02_C_01 SEQ ID NO:88, CaF1_JIE_02_C_05 SEQ ID NO:92, CaF1_JIE_02_E_08 SEQ ID NO:113, CaF1_JIE_03_B_09 SEQ ID NO:154, CaF1_JIE_03_G_08 SEQ ID NO:199, CaF1_JIE_04_E_10 SEQ ID NO:257, CaF1_JIE_04_F_08 SEQ ID NO:266, CaF1_JIE_04_G_03 SEQ ID NO:272, CaF1_JIE_05_B_05 SEQ ID NO:303, CaF1_JIE_07_G_07 SEQ ID NO:500, CaF1_JIE_07_H_01 SEQ ID NO:505, CaF1_JIE_07_H_09 SEQ ID NO:513, CaF1_JIE_07_H_11 SEQ ID NO:515, CaF1_JIE_08_D_04 SEQ ID NO:549, CaF1_JIE_09_E_08 SEQ ID NO:1288, CaF1_JIE_11_B_08 SEQ ID NO:1372, CaF1_JIE_11_D_10 SEQ ID NO:1391, CaF1_JIE_12_A_01 SEQ ID NO:1422, CaF1_JIE_12_A_03 SEQ ID NO:1424, CaF1_JIE_13_D_04 SEQ ID NO:1496, CaF1_JIE_13_D_05 SEQ ID NO:1497, CaF1_JIE_13_E_02 SEQ ID NO:1498, CaF1_JIE_14_C_08 SEQ ID NO:1541, CaF1_JIE_14_D_03 SEQ ID NO:1546, CaF1_JIE_15_A_03 SEQ ID NO:1583, CaF1_JIE_15_H_02 SEQ ID NO:1642, CaF1_JIE_17_A_07 SEQ ID NO:1721, CaF1_JIE_17_C_02 SEQ ID NO:1727, CaF1_JIE_17_C_03 SEQ ID NO:1728, CaF1_JIE_17_D_05 SEQ ID NO:1740, CaF1_JIE_17_D_06 SEQ ID NO:1741, CaF1_JIE_17_E_04 SEQ ID NO:1746, CaF1_JIE_17_F_02 SEQ ID NO:1752, CaF1_JIE_18_E_11 SEQ ID NO:1810, CaF1_JIE_19_G_07 SEQ ID NO:1891, CaF1_JIE_19_G_08 SEQ ID NO:1892, CaF1_JIE_19_G_09 SEQ ID NO:1893, CaF1_JIE_20_A_10 SEQ ID NO:1912, CaF1_JIE_21_A_08 SEQ ID NO:1993, CaF1_JIE_21_E_11 SEQ ID NO:2034, CaF1_JIE_21_F_09 SEQ ID NO:2040, CaF1_JIE_23_C_08 SEQ ID NO:2168, CaF1_JIE_23_D_09 SEQ ID NO:2177, CaF1_JIE_23_E_10 SEQ ID NO:2188, CaF1_JIE_23_F_09 SEQ ID NO:2197, CaF1_JIE_26_G_10 SEQ ID NO:2401, CaF1_JIE_29_H_02 SEQ ID NO:2561, CaF1_JIE_30_G_01 SEQ ID NO:2601, CaF1_JIE_30_G_11 SEQ ID NO:2607, CaF1_JIE_31_H_06 SEQ ID NO:2671, CaF1_JIE_32_B_11 SEQ ID NO:2685, CaF1_JIE_32_G_01 SEQ ID NO:2709, CaF1_JIE_33_B_11 SEQ ID NO:2739, CaF1_JIE_33_C_02 SEQ ID NO:2741, CaF1_JIE_34_D_02 SEQ ID NO:2804, CaF1_JIE_34_D_03 SEQ ID NO:2805, CaF1_JIE_34_E_04 SEQ ID NO:2813, CaF1_JIE_34_E_05 SEQ ID NO:2814, CaF1_JIE_34_G_02 SEQ ID NO:2822, CaF1_JIE_35_A_01 SEQ ID NO:2838, CaF1_JIE_35_D_08 SEQ ID NO:2867, CaF1_JIE_37_A_03 SEQ ID NO:2948, CaF1_JIE_37_D_03 SEQ ID NO:2966, CaF1_JIE_37_F_02 SEQ ID NO:2976, CaF1_JIE_37_F_07 SEQ ID NO:2978, CaF1_JIE_38_A_07 SEQ ID NO:3001, CaF1_JIE_39_D_06 SEQ ID NO:3080, CaF1_JIE_39_E_01 SEQ ID NO:3083, CaF1_WIE_01_F_02 SEQ ID NO:673, CaF1_WIE_01_F_03 SEQ ID NO:674, CaF1_WIE_01_H_09 SEQ ID NO:697, CaF1_WIE_03_C_01 SEQ ID NO:775, CaF1_WIE_03_E_02 SEQ ID NO:792, CaF1_WIE_03_G_02 SEQ ID NO:806, CaF1_WIE_04_G_02 SEQ ID NO:872, CaF1_WIE_06_A_04 SEQ ID NO:959, CaF1_WIE_06_B_05 SEQ ID NO:967, CaF1_WIE_06_B_06 SEQ ID NO:968, CaF1_WIE_06_B_11 SEQ ID NO:971, CaF1_WIE_06_C_06 SEQ ID NO:977, CaF1_WIE_06_E_04 SEQ ID NO:990, CaF1_WIE_06_G_11 SEQ ID NO:1013, CaF1_WIE_06_H_04 SEQ ID NO:1017, CaF1_WIE_07_A_11 SEQ ID NO:1033, CaF1_WIE_07_B_07 SEQ ID NO:1040, CaF1_WIE_07_E_03 SEQ ID NO:1066, CaF1_WIE_

07_F_01 SEQ ID NO:1073, CaF1_WIE_07_F_02 SEQ ID NO:1074, CaF1_WIE_07_G_10 SEQ ID NO:1092, CaF1_WIE_07_H_05 SEQ ID NO:1097, CaF1_WIE_08_D_11 SEQ ID NO:1139, CaF1_WIE_08_H_10 SEQ ID NO:1172, CaF1_WIE_08_H_11 SEQ ID NO:1173, CaF1_WIE_09_A_10 SEQ ID NO:1181, CaF1_WIE_09_F_04 SEQ ID NO:1212, CaF1_WIE_09_H_06 SEQ ID NO:1229, CaF1_WIE_10_A_02 SEQ ID NO:1235, CaF1_WIE_10_A_03 SEQ ID NO:1236, CaF1_WIE_10_B_07 SEQ ID NO:1249, CaF1_WIE_10_C_11 SEQ ID NO:1260, CaF1_WIE_10_E_05" SEQ ID NO:3275, CaF1_WIE_10_E_10 SEQ ID NO:3279, CaF1_WIE_10_E_11 SEQ ID NO:3280, CaF1_WIE_11_A_07 SEQ ID NO:3313, CaF1_WIE_11_B_07 SEQ ID NO:3322, CaF1_WIE_11_C_05 SEQ ID NO:3329, CaF1_WIE_11_F_06 SEQ ID NO:3354, CaF1_WIE_11_F_11 SEQ ID NO:3359, CaF1_WIE_12_D_04 SEQ ID NO:3406, CaF1_WIE_12_F_09 SEQ ID NO:3428, CaF1_WIE_13_H_10 SEQ ID NO:3522, CaF1_WIE_14_C_09 SEQ ID NO:3534, CaF1_WIE_14_E_10 SEQ ID NO:3544, CaF1_WIE_14_F_08 SEQ ID NO:3549, CaF1_WIE_14_F_09 SEQ ID NO:3550, CaF1_WIE_14_G_09 SEQ ID NO:3556, CaF1_WIE_15_F_08 SEQ ID NO:3590, CaF1_WIE_16_E_10 SEQ ID NO:3625, CaF1_WIE_17_D_05 SEQ ID NO:3677, CaF1_WIE_17_D_07 SEQ ID NO:3679, CaF1_WIE_17_E_07 SEQ ID NO:3690, CaF1_WIE_17_E_09 SEQ ID NO:3692, CaF1_WIE_17_H_07 SEQ ID NO:3720, CaF1_WIE_18_B_06 SEQ ID NO:3737, CaF1_WIE_18_C_01 SEQ ID NO:3741, CaF1_WIE_18_C_06 SEQ ID NO:3746, CaF1_WIE_18_C_09 SEQ ID NO:3749, CaF1_WIE_18_D_11 SEQ ID NO:3759, CaF1_WIE_18_F_03 SEQ ID NO:3772, CaF1_WIE_18_G_03 SEQ ID NO:3782, CaF1_WIE_19_B_08 SEQ ID NO:3812, CaF1_WIE_19_D_09 SEQ ID NO:3828, CaF1_WIE_19_E_03 SEQ ID NO:3830, CaF1_WIE_20_E_08 SEQ ID NO:3890, CaF1_WIE_20_F_05 SEQ ID NO:3896, CaF1_WIE_20_F_07 SEQ ID NO:3897, CaF1_WIE_21_A_10 SEQ ID NO:3922, CaF1_WIE_21_C_09 SEQ ID NO:3936, CaF1_WIE_21_D_01 SEQ ID NO:3939, CaF1_WIE_21_E_09 SEQ ID NO:3951, CaF1_WIE_21_F_11 SEQ ID NO:3959, CaF1_WIE_22_08 SEQ ID NO:3988, CaF1_WIE_23_H_09 SEQ ID NO:4085, CaF1_WIE_24_D_11 SEQ ID NO:4120, CaF1_WIE_24_E_06 SEQ ID NO:4124, CaF1_WIE_25_A_02 SEQ ID NO:4159, CaF1_WIE_25_E_02 SEQ ID NO:4196, CaF1_WIE_25_E_05 SEQ ID NO:4199, CaF1_WIE_26_A_02 SEQ ID NO:4225, CaF1_WIE_26_G_04 SEQ ID NO:4280, CaF1_WIE_27_B_03 SEQ ID NO:4311, CaF1_WIE_27_B_09 SEQ ID NO:4317, CaF1_WIE_27_D_06 SEQ ID NO:4332, CaF1_WIE_27_E_07 SEQ ID NO:4343, CaF1_WIE_27_F_07 SEQ ID NO:4354, CaF1_WIE_27_G_01 SEQ ID NO:4359, CaF1_WIE_27_H_03 SEQ ID NO:4372, CaF1_WIE_28_C_06 SEQ ID NO:4398, CaF1_WIE_29_B_05 SEQ ID NO:4460, CaF1_WIE_29_D_11 SEQ ID NO:4487, CaF1_WIE_29_E_02 SEQ ID NO:4489, CaF1_WIE_29_E_05 SEQ ID NO:4492, CaF1_WIE_29_G_01 SEQ ID NO:4510, CaF1_WIE_30_B_10 SEQ ID NO:4546, CaF1_WIE_30_G_02 SEQ ID NO:4585, CaF1_WIE_31_C_03 SEQ ID NO:4622, CaF1_WIE_32_A_09 SEQ ID NO:4679, CaF1_WIE_32_B_01 SEQ ID NO:4682, CaF1_WIE_32_B_05 SEQ ID NO:4685, CaF1_WIE_32_C_06 SEQ ID NO:4697, CaF1_WIE_32_E_06 SEQ ID NO:4711, CaF1_WIE_33_F_07 SEQ ID NO:4790, CaF1_WIE_33_G_06 SEQ ID NO:4799, CaF1_WIE_34_A_02 SEQ ID NO:4811, CaF1_WIE_34_B_10 SEQ ID NO:4826, CaF1_WIE_34_C_02 SEQ ID NO:4828, CaF1_WIE_34_D_03 SEQ ID NO:4838, CaF1_WIE_34_F_10 SEQ ID NO:4860, CaF1_WIE_34_G_04 SEQ ID NO:4864, CaF1_WIE_35_A_04 SEQ ID NO:4880, CaF1_WIE_35_A_05 SEQ ID NO:4881, CaF1_WIE_35_A_11 SEQ ID NO:4886, CaF1_WIE_35_C_02 SEQ ID NO:4898, CaF1_WIE_35_C_03 SEQ ID NO:4899, CaF1_WIE_35_C_11 SEQ ID NO:4906, CaF1_WIE_35_D_01 SEQ ID NO:4907, CaF1_WIE_35_F_04 SEQ ID NO:4930, CaF1_WIE_35_F_06 SEQ ID NO:4931, CaF1_WIE_35_G_10 SEQ ID NO:4945, CaF1_WIE_35_H_02 SEQ ID NO:4947, CaF1_WIE_35_H_04 SEQ ID NO:4949, CaF1_WIE_36_D_01 SEQ ID NO:4979, CaF1_WIE_36_F_01 SEQ ID NO:4996, CaF1_WIE_36_F_09 SEQ ID NO:5000, CaF1_WIE_36_F_11 SEQ ID NO:5001, CaF1_WIE_36_H_04 SEQ ID NO:5014, CaF1_WIE_36_H_05 SEQ ID NO:5015, CaF1_WIE_37_B_08 SEQ ID NO:5035, CaF1_WIE_37_E_01 SEQ ID NO:5048, CaF1_WIE_38_B_05 SEQ ID NO:5096, CaF1_WIE_38_C_07 SEQ ID NO:5105, CaF1_WIE_39_C_05 SEQ ID NO:5164, CaF1_WIE_39_G_08 SEQ ID NO:5188, CaF1_WIE_40_G_05 SEQ ID NO:5257, CaF1_WIE_40_G_10 SEQ ID NO:5262, CaF1_WIE_41_A_05 SEQ ID NO:5276, CaF1_WIE_41_A_08 SEQ ID NO:5278, CaF1_WIE_42_F_01 SEQ ID NO:5372, CaF1_WIE_42_H_11 SEQ ID NO:5388, CaF1_WIE_43_A_05 SEQ ID NO:5392, CaF1_WIE_43_B_10 SEQ ID NO:5404, CaF1_WIE_43_F_11 SEQ ID NO:5432, CaF1_WIE_44_A_06 SEQ ID NO:5445, CaF1_WIE_44_D_03 SEQ ID NO:5466, CaF1_WIE_44_D_07 SEQ ID NO:5470, CaF1_WIE_44_F_01 SEQ ID NO:5481, CaF1_WIE_44_H_02 SEQ ID NO:5495, CaF1_WIE_46_B_03 SEQ ID NO:5574, CaF1_WIE_46_E_01 SEQ ID NO:5599, CaF1_WIE_46_E_09 SEQ ID NO:5605, CaF1_WIE_47_F_03 SEQ ID NO:5682, CaF1_WIE_47_H_03 SEQ ID NO:5703, CaF1_WIE_47_H_10 SEQ ID NO:5709, CaF1_WIE_49_F_03 SEQ ID NO:5815, CaF1_WIE_50_B_05 SEQ ID NO:5842, CaF1_WIE_50_D_05 SEQ ID NO:5859, CaF1_WIE_50_F_06 SEQ ID NO:5878, CaF1_WIE_50_H_07 SEQ ID NO:5893, CaF1_WIE_51_E_07 SEQ ID NO:5937, CaF1_WIE_51_F_01 SEQ ID NO:5941, CaF1_WIE_51_H_09 SEQ ID NO:5955, CaF1_WIE_52_A_04 SEQ ID NO:5959, CaF1_WIE_52_B_09 SEQ ID NO:5973, CaF1_WIE_52_B_10 SEQ ID NO:5974, CaF1_WIE_52_C_05 SEQ ID NO:5979, CaF1_WIE_52_G_04 SEQ ID NO:6011, CaF1_WIE_53_A_05 SEQ ID NO:6030, CaF1_WIE_53_D_07 SEQ ID NO:6054, CaF1_WIE_53_D_08 SEQ ID NO:6055, CaF1_WIE_53_G_09 SEQ ID NO:6077, CaF1_WIE_54_A_03 SEQ ID NO:6083, CaF1_WIE_54_B_04 SEQ ID NO:6092, CaF1_WIE_54_D_04 SEQ ID NO:6112, CaF1_WIE_55_D_03 SEQ ID NO:6177, CaF1_WIE_55_D_08 SEQ ID NO:6180, CaF1_WIE_55_F_02 SEQ ID NO:6192, CaF1_WIE_55_F_11 SEQ ID NO:6198, CaF1_WIE_55_G_07 SEQ ID NO:6205, CaF1_WIE_55_H_11 SEQ ID NO:6218, CaF1_WIE_56_C_07 SEQ ID NO:6237, CaF1_WIE_56_E_10 SEQ ID NO:6250 and CaF1_WIE_56_G_03 SEQ ID NO:6259.

Genes Encoding Nucleotide Binding Proteins

In our study, GTP binding proteins were found to be the major class of nucleotide binding proteins in susceptible as well as resistant genotypes. The stress-responsive predominant GTP binding proteins were of Ras, Rab and Ran type. ESTs encoding ras-like small monomeric GTP-binding protein and GMPase were present in the susceptible genotype while Rab, RABIC, GTP cyclohydrolase and RabGAP/TBC were found only in the resistant one. However, ESTs encoding Ras small GTPase and RAB1X were identified in both the genotypes. GTP binding proteins are reported to be associated with a wide range of growth and developmental processes besides their role in plant defense.

Accordingly the present invention provides ESTs derived from chickpea, wherein the ESTs are related to nucleotide binding proteins. These ESTs are CaF1_JIE_01 B_11 SEQ ID NO:20, CaF1_JIE_02_G_04 SEQ ID NO:126, CaF1_JIE_02_G_10_SEQ ID NO:132, CaF1_JIE_05_D_03 SEQ ID NO:321, CaF1_JIE_13_C_08 SEQ ID NO:1493, CaF1_JIE_24_B_11 SEQ ID NO:2239, CaF1_JIE_25_F_04 SEQ ID NO:2327, CaF1_JIE_25_F_09 SEQ ID NO:2331, CaF1_JIE_25_H_01 SEQ ID NO:2340, CaF1_JIE_27_C_04 SEQ ID NO:2427, CaF1_JIE_29_C_03 SEQ ID NO:2534, CaF1_JIE_29_H_06 SEQ ID NO:2564, CaF1_JIE_32_G_03 SEQ ID NO:2710, CaF1_WIE_01_H_06 SEQ ID NO:695, CaF1_WIE_05_F_09 SEQ ID NO:937, CaF1_WIE_07_C_06 SEQ ID NO:1049, CaF1_WIE_07_D_11 SEQ ID NO:1063, CaF1_WIE_10_B_02 SEQ ID NO:1244, CaF1_WIE_14_G_02 SEQ ID NO:3552, CaF1_WIE_23_G_08 SEQ ID NO:4076, CaF1_WIE_25_E_04 SEQ ID NO:4198, CaF1_WIE_25_H_03 SEQ ID NO:4217, CaF1_WIE_26_H_09 SEQ ID NO:4296, CaF1_WIE_29_B_02 SEQ ID NO:4457, CaF1_WIE_29_F_09 SEQ ID NO:4507, CaF1_WIE_34_C_03 SEQ ID NO:4829, CaF1_WIE_36_A_09 SEQ ID NO:4962, CaF1_WIE_39_F_08 SEQ ID NO:5181, CaF1_WIE_41_E_07 SEQ ID NO:5312, CaF1_WIE_44_E_07 SEQ ID NO:5478, CaF1_WIE_46_A_07 SEQ ID NO:5569, CaF1_WIE_46_A_08 SEQ ID NO:5570, CaF1_WIE_46_D_06. SEQ ID NO:5595, CaF1_WIE_49_F_06 SEQ ID NO:5817 and CaF1_WIE_52_C_06 SEQ ID NO:5980.

Genes Involved in Metabolism

Developmental changes and stress responses are often correlated with or result in adjustments in various metabolic pathways. The functional class of metabolism comprised of about 14.56% of the unigenes and represented the largest class apart from NSH and hypothetical proteins. The genes present in this class represented several biochemical pathways such as carbohydrate, fatty acid, energy and protein metabolism besides nitrogen and nucleotide metabolism. The genes involved in carbohydrate metabolism comprised alcohol dehydrogenase (ADH), glyceraldehyde3-phosphate dehydrogenase (GAPDH), enolase, fructose-bisphosphate aldolase, malate dehydrogenase, phosphoenol pyruvate (PEP) carboxylase and triosephosphate isomerase and were present in both the genotypes. Most of these enzymes are known to show altered expression in response to stress. Though very little is known about the direct role of these proteins in defense, many such enzymes are involved in maintaining metabolite pool that may drive the metabolic processes to overcome such stresses. Polygalactouronase inhibiting protein (PGIP) was present in both the susceptible and resistant genotypes. The PGIPs are cell wall proteins, which act against fungal polygalactouronases that are important pathogenecity factors. Besides their classical function, they also form long chain oligogalactouronides and facilitate the activation of plant defense responses. We observed the presence of β1,3-glucanase, a PR 2 family protein, which was earlier shown to be expressed in response to pathogen infection.

The genes involved in lipid biosynthesis, for example, acyl Co-A synthetase and acyl Co-A binding proteins were found to be present in both the genotypes. The enzyme acyl Co-A synthetase has been shown to be induced in response to compatible and incompatible interactions between *Xanthomonas* and *Capsicum* annum while Acyl Co-A binding proteins play an important role in intracellular transport and formation of acyl Co-A pools. ESTs encoding desaturases in the CaUnigene set showed varied substrate specificity between the two genotypes. For example, oleate and sterol desaturases were found in the susceptible genotype and putative desaturase-like protein was present in the resistant one. Desaturases catalyze the formation of double bonds in lipids thereby increasing the lipid fluidity, which might be required as an adjustment associated with membrane stability under progressive wilting. ESTs corresponding to other lipid metabolism genes such as serine C-palmitoyltransferase, was also found to be present in stressed tissues. Identification of sterol metabolism related enzymes such as sterol methyl transferases and oxysterol binding proteins suggest the occurrence of lipid modifications during pathostress. Presence of HMG Co-A reductase which catalyzes the synthesis of mevalonate, a specific precursor of plant defense metabolite sesquiterpene phytoelexins, is indicative of its role in cell defense.

Several amino acids act as precursors for the synthesis of specialized metabolites, during varied cellular adaptations. ESTs encoding enzymes involved in amino acid metabolism, for example, arginine decarboxylase, aspartate aminotransferase, and cysteine synthase were identified in both the genotypes. Recent evidence suggests that arginine decarboxylase, involved in putrescine biosynthesis, is induced in response to various environmental stresses. Proline dehydrogenase and many proline-rich proteins were identified in resistant genotype. Proline dehydrogenase is the rate-limiting enzyme in proline degradation and serves important functions in stress responses.

Nucleotide metabolism related genes such as nuleoside diphosphate kinase (NDK), adenine nucleotide translocator and polynucleotide phosphorylase were also identified in both, the genotypes. Previously, it has been shown that the overexpressing NDK provides higher ability to eliminate $H_2O_2$, indicating its potential role in the management of reactive oxygen species under stress.

Another embodiment of the present invention provides ESTs derived from chickpea, wherein the ESTs are related to metabolism. These ESTs are CaF1_JIE_01_A_05 SEQ ID NO:4, CaF1_JIE_01_B_02 SEQ ID NO:11, CaF1_JIE_01_B_03 SEQ ID NO:12, CaF1_JIE_01_B_04 SEQ ID NO:13, CaF1_JIE_01_B_07 SEQ ID NO:16, CaF1_JIE_01_C_07 SEQ ID NO:27, CaF1_JIE_01_C_08 SEQ ID NO:28, CaF1_JIE_01_C_09 SEQ ID NO:29, CaF1_JIE_01_D_02 SEQ ID NO:33, CaF1_JIE_01_D_07 SEQ ID NO:37, CaF1_JIE_01_E_03 SEQ ID NO:43, CaF1_JIE_01_E_06 SEQ ID NO:46, CaF1_JIE_01_E_10 SEQ ID NO:49, CaF1_JIE_01_F_04 SEQ ID NO:52, CaF1_JIE_01_F_06 SEQ ID NO:54, CaF1_JIE_01_G_04 SEQ ID NO:61, CaF1_JIE_01_G_06 SEQ ID NO:63, CaF1_JIE_01_G_08 SEQ ID NO:64, CaF1_JIE_02_A_11 SEQ ID NO:79, CaF1_JIE_02_D_02 SEQ ID NO:99, CaF1_JIE_02_E_01 SEQ ID NO:108, CaF1_JIE_02_E_06 SEQ ID NO:112, CaF1_JIE_02_E_09 SEQ ID NO:114, CaF1_JIE_02_F_03 SEQ ID NO:117, CaF1_JIE_02_F_09 SEQ ID NO:122, CaF1_JIE_02_G_07 SEQ ID NO:129, CaF1_JIE_02_H_02 SEQ ID NO:134, CaF1_JIE_03_A_04 SEQ ID NO:146, CaF1_JIE_03_C_01 SEQ ID NO:157, CaF1_JIE_03_D_01 SEQ ID NO:166, CaF1_JIE_03_E_01 SEQ ID NO:174, CaF1_JIE_03_E_02 SEQ ID NO:175, CaF1_JIE_03_E_08 SEQ ID NO:179, CaF1_JIE_03_F_01 SEQ ID NO:183, CaF1_JIE_03_F_03 SEQ ID NO:185, CaF1_JIE_03_F_04 SEQ ID NO:186, CaF1_JIE_03_F_06 SEQ ID NO:188, CaF1_JIE_03_F_07 SEQ ID NO:189, CaF1_JIE_03_G_02 SEQ ID NO:194, CaF1_JIE_03_H_

11 SEQ ID NO:209, CaF1_JIE_04_C_03 SEQ ID NO:233, CaF1_JIE_04_C_06 SEQ ID NO:236, CaF1_JIE_04_D_01 SEQ ID NO:240, CaF1_JIE_04_D_03 SEQ ID NO:242, CaF1_JIE_04_D_08 SEQ ID NO:246, CaF1_JIE_04_D_10 SEQ ID NO:248, CaF1_JIE_04_E_02 SEQ ID NO:251, CaF1_JIE_04_E_09 SEQ ID NO:256, CaF1_JIE_04_F_10 SEQ ID NO:268, CaF1_JIE_04_H_05 SEQ ID NO:284, CaF1_JIE_04_H_10 SEQ ID NO:288, CaF1_JIE_05_B_03 SEQ ID NO:301, CaF1_JIE_05_13104 SEQ ID NO:302, CaF1_JIE_05_D_09 SEQ ID NO:327, CaF1_JIE_05_E_03 SEQ ID NO:332, CaF1_JIE_05_F_04 SEQ ID NO:344, CaF1_JIE_05_F_07 SEQ ID NO:347, CaF1_JIE_05_F_11 SEQ ID NO:350, CaF1_JIE_05_G_03 SEQ ID NO:353, CaF1_JIE_06_A_01 SEQ ID NO:371, CaF1_JIE_06_B_05 SEQ ID NO:383, CaF1_JIE_06_D_01 SEQ ID NO:395, CaF1_JIE_06_D_03 SEQ ID NO:397, CaF1_JIE_06_D_05 SEQ ID NO:399, CaF1_JIE_06_D_07 SEQ ID NO:400, CaF1_JIE_06_D_09 SEQ ID NO:402, CaF1_JIE_06_E_01 SEQ ID NO:405, CaF1_JIE_06_F_11 SEQ ID NO:420, CaF1_JIE_06_G_05 SEQ ID NO:425, CaF1_JIE_06_H_01 SEQ ID NO:429, CaF1_JIE_06_H_04 SEQ ID NO:431, CaF1_JIE_06_H_09 SEQ ID NO:435, CaF1_JIE_07_A_02 SEQ ID NO:437, CaF1_JIE_07_A_09 SEQ ID NO:442, CaF1_JIE_07_B_06 SEQ ID NO:449, CaF1_JIE_07_C_02 SEQ ID NO:455, CaF1_JIE_07_C_08 SEQ ID NO:461, CaF1_JIE_07_F_01 SEQ ID NO:485, CaF1_JIE_07_F_02 SEQ ID NO:486, CaF1_JIE_07_G_09 SEQ ID NO:502, CaF1_JIE_07_G_11 SEQ ID NO:504, CaF1_JIE_07_H_07 SEQ ID NO:511, CaF1_JIE_08_A_02 SEQ ID NO:517, CaF1_JIE_08_B_05 SEQ ID NO:529, CaF1_JIE_08_C_11 SEQ ID NO:545, CaF1_JIE_08_F_02 SEQ ID NO:568, CaF1_JIE_08_G_04 SEQ ID NO:579, CaF1_JIE_08_H_04 SEQ ID NO:590, CaF1_JIE_08_H_08 SEQ ID NO:594, CaF1_JIE_09_C_04 SEQ ID NO:621, CaF1_JIE_09_D_04 SEQ ID NO:1273, CaF1_JIE_09_D_10 SEQ ID NO:1279, CaF1_JIE_09_E_01 SEQ ID NO:1281, CaF1_JIE_09_E_04 SEQ ID NO:1284, CaF1_JIE_09_F_06 SEQ ID NO:1296, CaF1_JIE_09_G_06 SEQ ID NO:1305, CaF1_JIE_09_G_09 SEQ ID NO:1307, CaF1_JIE_09_G_10 SEQ ID NO:1308, CaF1_JIE_09_H_08 SEQ ID NO:1315, CaF1_JIE_10_A_08 SEQ ID NO:1321, CaF1_JIE_10_B_09 SEQ ID NO:1331, CaF1_JIE_10_D_03 SEQ ID NO:1337, CaF1_JIE_10_F_01 SEQ ID NO:1342, CaF1_JIE_10_H_03 SEQ ID NO:1354, CaF1_JIE_11_A_07 SEQ ID NO:1364, CaF1_JIE_11_A_08 SEQ ID NO:1365, CaF1_JIE_11_A_09 SEQ ID NO:1366, CaF1_JIE_11_D_01 SEQ ID NO:1384, CaF1_JIE_11_D_02 SEQ ID NO:1385, CaF1_JIE_11_D_03 SEQ ID NO:1386, CaF1_JIE_11_D_09 SEQ ID NO:1390, CaF1_JIE_11_E_04 SEQ ID NO:1394, CaF1_JIE_11_E_05 SEQ ID NO:1395, CaF1_JIE_11_E_10 SEQ ID NO:1400, CaF1_JIE_11_F_02 SEQ ID NO:1401, CaF1_JIE_11_F_06 SEQ ID NO:1405, CaF1_JIE_11_G_03 SEQ ID NO:1410, CaF1_JIE_11_G_06 SEQ ID NO:1413, CaF1_JIE_11_G_10 SEQ ID NO:1417, CaF1_JIE_11_H_08 SEQ ID NO:1420, CaF1_JIE_11_H_10 SEQ ID NO:1421, CaF1_JIE_12_A_11 SEQ ID NO:1429, CaF1_JIE_12_B_01 SEQ ID NO:1430, CaF1_JIE_12_C_04 SEQ ID NO:1443, CaF1_JIE_12_C_05 SEQ ID NO:1444, CaF1_JIE_12_C_11 SEQ ID NO:1448, CaF1_JIE_12_D_01 SEQ ID NO:1449, CaF1_JIE_12_D_02 SEQ ID NO:1450, CaF1_JIE_12_F_09 SEQ ID NO:1465, CaF1_JIE_12_F_10 SEQ ID NO:1466, CaF1_JIE_12_G_09 SEQ ID NO:1470, CaF1_JIE_12_G_10 SEQ ID NO:1471, CaF1_JIE_12_H_08 SEQ ID NO:1475, CaF1_JIE_13_A_01 SEQ ID NO:1477, CaF1_JIE_13_E_03 SEQ ID NO:1499, CaF1_JIE_13_E_07 SEQ ID NO:1500, CaF1_JIE_13_G_02 SEQ ID NO:1508, CaF1_JIE_13_G_04 SEQ ID NO:1509, CaF1_JIE_13_H_03 SEQ ID NO:1517, CaF1_JIE_14_B_09 SEQ ID NO:1533, CaF1_JIE_14_B_11 SEQ ID NO:1535, CaF1_JIE_14_D_06 SEQ ID NO:1548, CaF1_JIE_14_D_09 SEQ ID NO:1550, CaF1_JIE_14_D_10 SEQ ID NO:1551, CaF1_JIE_14_F_02 SEQ ID NO:1560, CaF1_JIE_14_F_06 SEQ ID NO:1564, CaF1_JIE_14_F_11 SEQ ID NO:1566, CaF1_JIE_14_H_02 SEQ ID NO:1575, CaF1_JIE_14_H_05 SEQ ID NO:1577, CaF1_JIE_14_H_06 SEQ ID NO:1578, CaF1_JIE_14_H_09 SEQ ID NO:1580, CaF1_JIE_15_A_10 SEQ ID NO:1590, CaF1_JIE_15_B_02 SEQ ID NO:1592, CaF1_JIE_15_B_05 SEQ ID NO:1594, CaF1_JIE_15_B_09 SEQ ID NO:1598, CaF1_JIE_15_B_10 SEQ ID NO:1599, CaF1_JIE_15_D_09 SEQ ID NO:1615, CaF1_JIE_15_G_02 SEQ ID NO:1632, CaF1_JIE_15_G_03 SEQ ID NO:1633, CaF1_JIE_15_G_08 SEQ ID NO:1637, CaF1_JIE_15_G_10 SEQ ID NO:1639, CaF1_JIE_15_H_01 SEQ ID NO:1641, CaF1_JIE_15_H_08 SEQ ID NO:1646, CaF1_JIE_16_B_05 SEQ ID NO:1660, CaF1_JIE_16_C_03 SEQ ID NO:1667, CaF1_JIE_16_C_04 SEQ ID NO:1668, CaF1_JIE_16_D_01 SEQ ID NO:1676, CaF1_JIE_16_D_11 SEQ ID NO:1682, CaF1_JIE_16_E_01 SEQ ID NO:1683, CaF1_JIE_16_F_08 SEQ ID NO:1698, CaF1_JIE_16_G_05 SEQ ID NO:1702, CaF1_JIE_16_H_06 SEQ ID NO:1711, CaF1_JIE_16_H_08 SEQ ID NO:1713, CaF1_JIE_16_H_11 SEQ ID NO:1715, CaF1_JIE_17_A_03 SEQ ID NO:1718, CaF1_JIE_17_A_04 SEQ ID NO:1719, CaF1_JIE_17_B_01 SEQ ID NO:1723, CaF1_JIE_17_D_03 SEQ ID NO:1738, CaF1_JIE_17_F_04 SEQ ID NO:1753, CaF1_JIE_17_G_04 SEQ ID NO:1760, CaF1_JIE_17_H_07 SEQ ID NO:1766, CaF1_JIE_17_H_09 SEQ ID NO:1767, CaF1_JIE_18_A_07 SEQ ID NO:1772, CaF1_JIE_18_C_02 SEQ ID NO:1784, CaF1_JIE_18_C_03 SEQ ID NO:1785, CaF1_JIE_18_C_04 SEQ ID NO:1786, CaF1_JIE_18_C_10 SEQ ID NO:1792, CaF1_JIE_18_F_01 SEQ ID NO:1811, CaF1_JIE_18_F_02 SEQ ID NO:1812, CaF1_JIE_18_F_08 SEQ ID NO:1817, CaF1_JIE_19_A_05 SEQ ID NO:1840, CaF1_JIE_19_D_01 SEQ ID NO:1862, CaF1_JIE_19_E_04 SEQ ID NO:1871, CaF1_JIE_19_E_06 SEQ ID NO:1872, CaF1_JIE_19_E_10 SEQ ID NO:1875, CaF1_JIE_19_F_03 SEQ ID NO:1879, CaF1_JIE_19_F_08 SEQ ID NO:1883, CaF1_JIE_19_F_11 SEQ ID NO:1886, CaF1_JIE_19_G_06 SEQ ID NO:1890, CaF1_JIE_19_H_05 SEQ ID NO:1899, CaF1_JIE_19_H_08 SEQ ID NO:1901, CaF1_JIE_19_H_09 SEQ ID NO:1902, CaF1_JIE_20_B_08 SEQ ID NO:1920, CaF1_JIE_20_D_06 SEQ ID NO:1939, CaF1_JIE_20_D_07 SEQ ID NO:1940, CaF1_JIE_20_E_03 SEQ ID NO:1947, CaF1_JIE_20_E_08 SEQ ID NO:1952, CaF1_JIE_20_E_10 SEQ ID NO:1954, CaF1_JIE_20_F_07 SEQ ID NO:1962, CaF1_JIE_20_G_09 SEQ ID NO:1973, CaF1_JIE_20_H_01 SEQ ID NO:1976, CaF1_JIE_21_A_02 SEQ ID NO:1988, CaF1_JIE_21_A_04 SEQ ID NO:1989, CaF1_JIE_21_A_10 SEQ ID NO:1995, CaF1_JIE_21_C_10 SEQ ID NO:2015, CaF1_JIE_21_G_03 SEQ ID NO:2044, CaF1_JIE_21_G_09 SEQ ID NO:2048, CaF1_JIE_21_H_03 SEQ ID NO:2052, CaF1_JIE_21_H_05 SEQ ID NO:2054, CaF1_JIE_22_A_05 SEQ ID NO:2065, CaF1_JIE_22_A_06 SEQ ID NO:2066, CaF1_JIE_22_A_07 SEQ ID NO:2067, CaF1_JIE_22_A_09 SEQ ID NO:2069, CaF1_JIE_22_B_04 SEQ ID

NO:2075, CaF1_JIE_22_B_05 SEQ ID NO:2076, CaF1_JIE_22_B_10 SEQ ID NO:2081, CaF1_JIE_22_D_01 SEQ ID NO:2090, CaF1_JIE_22_E_04 SEQ ID NO:2102, CaF1_JIE_22_E_09 SEQ ID NO:2106, CaF1_JIE_22_E_10 SEQ ID NO:2107, CaF1_JIE_22_G_01 SEQ ID NO:2120, CaF1_JIE_23_A_04 SEQ ID NO:2144, CaF1_JIE_23_A_07 SEQ ID NO:2147, CaF1_JIE_23_A_08 SEQ ID NO:2148, CaF1_JIE_23_D_10 SEQ ID NO:2178, CaF1_JIE_23_E_08 SEQ ID NO:2186, CaF1_JIE_23_F_10 SEQ ID NO:2198, CaF1_JIE_23_F_11 SEQ ID NO:2199, CaF1_JIE_23_G_04 SEQ ID NO:2203, CaF1_JIE_24_B_01 SEQ ID NO:2231, CaF1_JIE_24_D_03 SEQ ID NO:2250, CaF1_JIE_24_D_07 SEQ ID NO:2254, CaF1_JIE_24_E_07 SEQ ID NO:2262, CaF1_JIE_25_B_01 SEQ ID NO:2297, CaF1_JIE_25_B_05 SEQ ID NO:2301, CaF1_JIE_25_C_06 SEQ ID NO:2306, CaF1_JIE_25_D_05 SEQ ID NO:2312, CaF1_JIE_25_D_08 SEQ ID NO:2315, CaF1_JIE_25_F_07 SEQ ID NO:2329, CaF1_JIE_25_G_11 SEQ ID NO:2339, CaF1_JIE_26_A_01 SEQ ID NO:2347, CaF1_JIE_26_B_01 SEQ ID NO:2355, CaF1_JIE_26_B_02 SEQ ID NO:2356, CaF1_JIE_26_C_07 SEQ ID NO:2368, CaF1_JIE_26_C_11 SEQ ID NO:2371, CaF1_JIE_26_D_05 SEQ ID NO:2375, CaF1_JIE_26_E_01 SEQ ID NO:2381, CaF1_JIE_26_E_11 SEQ ID NO:2388, CaF1_JIE_26_F_01 SEQ ID NO:2389, CaF1_JIE_26_F_11 SEQ ID NO:2396, CaF1_JIE_26_G_07 SEQ ID NO:2399, CaF1_JIE_27_A_02 SEQ ID NO:2411, CaF1_JIE_27_A_04 SEQ ID NO:2413, CaF1_JIE_27_A_09 SEQ ID NO:2416, CaF1_JIE_27_A_10 SEQ ID NO:2417, CaF1_JIE_27_B_09 SEQ ID NO:2423, CaF1_JIE_27_C_06 SEQ ID NO:2429, CaF1_JIE_27_C_11 SEQ ID NO:2432, CaF1_JIE_27_D_02 SEQ ID NO:2434, CaF1_JIE_27_D_10 SEQ ID NO:2441, CaF1_JIE_27_F_05 SEQ ID NO:2452, CaF1_JIE_27_F_08 SEQ ID NO:2454, CaF1_JIE_27_F_09 SEQ ID NO:2455, CaF1_JIE_27_G_01 SEQ ID NO:2457, CaF1_JIE_28_A_08 SEQ ID NO:2472, CaF1_JIE_28_A_09 SEQ ID NO:2473, CaF1_JIE_28_A_10 SEQ ID NO:2474, CaF1_JIE_28_B_05 SEQ ID NO:2477, CaF1_JIE_28_B_09 SEQ ID NO:2479, CaF1_JIE_28_B_10 SEQ ID NO:2480, CaF1_JIE_28_C_06 SEQ ID NO:2484, CaF1_JIE_28_C_11 SEQ ID NO:2488, CaF1_JIE_28_D_10 SEQ ID NO:2495, CaF1_JIE_28_F_08 SEQ ID NO:2505, CaF1_JIE_28_F_09 SEQ ID NO:2506, CaF1_JIE_28_G_10 SEQ ID NO:2512, CaF1_JIE_28_H_08 SEQ ID NO:2517, CaF1_JIE_29_D_08 SEQ ID NO:2542, CaF1_JIE_29_D_10 SEQ ID NO:2544, CaF1_JIE_30_A_06 SEQ ID NO:2572, CaF1_JIE_30_D_08 SEQ ID NO:2589, CaF1_JIE_30_G_08 SEQ ID NO:2605, CaF1_JIE_30_H_01 SEQ ID NO:2608, CaF1_JIE_30_H_03 SEQ ID NO:2609, CaF1_JIE_30_H_04 SEQ ID NO:2610, CaF1_JIE_30_H_10 SEQ ID NO:2614, CaF1_JIE_31_A_04 SEQ ID NO:2618, CaF1_JIE_31_A_09 SEQ ID NO:2622, CaF1_JIE_31_A_10 SEQ ID NO:2623, CaF1_JIE_31_B_03 SEQ ID NO:2624, CaF1_JIE_31_B_11 SEQ ID NO:2630, CaF1_JIE_31_E_09 SEQ ID NO:2646, CaF1_JIE_31_E_10 SEQ ID NO:2647, CaF1_JIE_31_E_11 SEQ ID NO:2648, CaF1_JIE_31_F_08 SEQ ID NO:2655, CaF1_JIE_31_G_10 SEQ ID NO:2665, CaF1_JIE_32_C_04 SEQ ID NO:2688, CaF1_JIE_32_D_02 SEQ ID NO:2691, CaF1_JIE_32_D_06 SEQ ID NO:2694, CaF1_JIE_32_E_08 SEQ ID NO:2700, CaF1_JIE_32_H_11 SEQ ID NO:2720, CaF1_JIE_33_B_06 SEQ ID NO:2734, CaF1_JIE_33_B_07 SEQ ID NO:2735, CaF1_JIE_33_B_08 SEQ ID NO:2736, CaF1_JIE_33_B_10 SEQ ID NO:2738, CaF1_JIE_33_C_06 SEQ ID NO:2744, CaF1_JIE_33_C_07 SEQ ID NO:2745, CaF1_JIE_33_C_08 SEQ ID NO:2746, CaF1_JIE_33_E_04 SEQ ID NO:2757, CaF1_JIE_33_F_05 SEQ ID NO:2762, CaF1_JIE_34_C_10 SEQ ID NO:2801, CaF1_JIE_34_D_01 SEQ ID NO:2803, CaF1_JIE_34_F_05 SEQ ID NO:2819, CaF1_JIE_34_F_06 SEQ ID NO:2820, CaF1_JIE_34_H_01 SEQ ID NO:2828, CaF1_JIE_35_B_04 SEQ ID NO:2847, CaF1_JIE_35_B_07 SEQ ID NO:2850, CaF1_JIE_35_B_09 SEQ ID NO:2851, CaF1_JIE_35_B_10 SEQ ID NO:2852, CaF1_JIE_35_C_03 SEQ ID NO:2855, CaF1_JIE_35_C_06 SEQ ID NO:2858, CaF1_JIE_35_D_01 SEQ ID NO:2861, CaF1_JIE_35_G_02 SEQ ID NO:2880, CaF1_JIE_35_G_03 SEQ ID NO:2881, CaF1_JIE_35_G_04 SEQ ID NO:2882, CaF1_JIE_35_H_01 SEQ ID NO:2886, CaF1_JIE_35_H_04 SEQ ID NO:2888, CaF1_JIE_36_B_03 SEQ ID NO:2900, CaF1_JIE_36_B_07 SEQ ID NO:2903, CaF1_JIE_36_D_05 SEQ ID NO:2916, CaF1_JIE_36_D_07 SEQ ID NO:2918, CaF1_JIE_36_D_09 SEQ ID NO:2920, CaF1_JIE_36_F_08 SEQ ID NO:2933, CaF1_JIE_36_F_11 SEQ ID NO:2935, CaF1_JIE_37_A_04 SEQ ID NO:2949, CaF1_JIE_37_A_05 SEQ ID NO:2950, CaF1_JIE_37_A_08 SEQ ID NO:2953, CaF1_JIE_37_B_02 SEQ ID NO:2954, CaF1_JIE_37_C_04 SEQ ID NO:2960, CaF1_JIE_37_D_06 SEQ ID NO:2968, CaF1_JIE_37_F_09 SEQ ID NO:2980, CaF1_JIE_37_G_02 SEQ ID NO:2981, CaF1_JIE_37_L_G_11 SEQ ID NO:2989, CaF1_JIE_37_H_11 SEQ ID NO:2997, CaF1_JIE_38_A_09 SEQ ID NO:3003, CaF1_JIE_38_B_02 SEQ ID NO:3006, CaF1_JIE_38_B_05 SEQ ID NO:3009, CaF1_JIE_38_B_10 SEQ ID NO:3014, CaF1_JIE_38_F_06 SEQ ID NO:3038, CaF1_JIE_38_F_08 SEQ ID NO:3040, CaF1_JIE_38_F_09 SEQ ID NO:3041, CaF1_JIE_39_B_04 SEQ ID NO:3063, CaF1_JIE_39_C_03 SEQ ID NO:3070, CaF1_JIE_39_C_04 SEQ ID NO:3071, CaF1_JIE_39_E_03 SEQ ID NO:3085, CaF1_JIE_39_E_08 SEQ ID NO:3088, CaF1_JIE_39_F_06 SEQ ID NO:3094, CaF1_JIE_39_F_08 SEQ ID NO:3095, CaF1_JIE_39_H_04 SEQ ID NO:3108, CaF1_JIE_39_H_07 SEQ ID NO:3110, CaF1_JIE_40_C_10 SEQ ID NO:3137, CaF1_JIE_40_F_01 SEQ ID NO:3154, CaF1_JIE_40_G_07 SEQ ID NO:3166, CaF1_JIE_40_G_10 SEQ ID NO:3169, CaF1_JIE_40_H_03 SEQ ID NO:3173, CaF1_JIE_40_H_04 SEQ ID NO:3174, CaF1_JIE_41_B_02 SEQ ID NO:3187, CaF1_JIE_41_B_07 SEQ ID NO:3191, CaF1_JIE_41_B_10 SEQ ID NO:3193, CaF1_JIE_41_B_11 SEQ ID NO:3194, CaF1_JIE_41_E_01 SEQ ID NO:3211, CaF1_JIE_41_G_04 SEQ ID NO:3231, CaF1_JIE_41_H_10 SEQ ID NO:3242, CaF1_JIE_42_A_01 SEQ ID NO:3243, CaF1_JIE_42_C_04 SEQ ID NO:3254, CaF1_JIE_42_C_05 SEQ ID NO:3255, CaF1_JIE_01_A_01 SEQ ID NO:630, CaF1_WIE_01_A_10 SEQ ID NO:638, CaF1_JIE_01_A_11 SEQ ID NO:639, CaF1_WIE_01_C_11 SEQ ID NO:654, CaF1_WIE_01_E_08 SEQ ID NO:670, CaF1_WIE_01_G_05 SEQ ID NO:684, CaF1_WIE_01_G_06 SEQ ID NO:685, CaF1_WIE_01_G_10 SEQ ID NO:689, CaF1_WIE_01_H_10 SEQ ID NO:698, CaF1_WIE_02_A_02 SEQ ID NO:700, CaF1_WIE_02_C_02 SEQ ID NO:714, CaF1_WIE_02_C_06 SEQ ID NO:718, CaF1_WIE_02_D_06 SEQ ID NO:725, CaF1_WIE_02_E_06 SEQ ID NO:733, CaF1_WIE_02_F_02 SEQ ID NO:740, CaF1_WIE_02_F_03 SEQ ID NO:741, CaF1_WIE_

02_H_06 SEQ ID NO:758, CaF1_WIE_03_A_05 SEQ ID NO:766, CaF1_WIE_03_B_08 SEQ ID NO:772, CaF1_WIE_03_C_03 SEQ ID NO:777, CaF1_WIE_03_D_04 SEQ ID NO:785, CaF1_WIE_03_E_06 SEQ ID NO:794, CaF1_WIE_03_H_03 SEQ ID NO:812, CaF1_WIE_03_H_10 SEQ ID NO:815, CaF1_WIE_04_A_02 SEQ ID NO:818, CaF1_WIE_04_A_03 SEQ ID NO:819, CaF1_WIE_04_A_09 SEQ ID NO:823, CaF1_WIE_04_A_10 SEQ ID NO:824, CaF1_WIE_04_C_04 SEQ ID NO:838, CaF1_WIE_04_C_05 SEQ ID NO:839, CaF1_WIE_04_D_03 SEQ ID NO:845, CaF1_WIE_04_D_04 SEQ ID NO:846, CaF1_WIE_04_D_05 SEQ ID NO:847, CaF1_WIE_04_D_06 SEQ ID NO:848, CaF1_WIE_04_E_10 SEQ ID NO:852, CaF1_WIE_04_E_05 SEQ ID NO:856, CaF1_WIE_04_E_10 SEQ ID NO:861, CaF1_WIE_04_F_07 SEQ ID NO:868, CaF1_WIE_04_F_10 SEQ ID NO:870, CaF1_WIE_04_G_04 SEQ ID NO:873, CaF1_WIE_04_H_05 SEQ ID NO:883, CaF1_WIE_04_H_07 SEQ ID NO:885, CaF1_WIE_05_C_05 SEQ ID NO:907, CaF1_WIE_05_D_07 SEQ ID NO:917, CaF1_WIE_05_E_10 SEQ ID NO:930, CaF1_WIE_06_A_01 SEQ ID NO:957, CaF1_WIE_06_A_07 SEQ ID NO:962, CaF1_WIE_06_B_02 SEQ ID NO:966, CaF1_WIE_06_C_02 SEQ ID NO:973, CaF1_WIE_06_D_07 SEQ ID NO:983, CaF1_WIE_06_E_02 SEQ ID NO:988, CaF1_WIE_06_F_10 SEQ ID NO:1004, CaF1_WIE_06_G_09 SEQ ID NO:1011, CaF1_WIE_06_H_07 SEQ ID NO:1020, CaF1_WIE_06_H_10 SEQ ID NO:1023, CaF1_WIE_07_A_02 SEQ ID NO:1026, CaF1_WIE_07_B_02 SEQ ID NO:1035, CaF1_WIE_07_C_07 SEQ ID NO:1050, CaF1_JIE_07_C_11 SEQ ID NO:1053, CaF1_WIE_07_D_01 SEQ ID NO:1054, CaF1_WIE_07_D_03 SEQ ID NO:1055, CaF1_WIE_07_D_04 SEQ ID NO:1056, CaF1_WIE_07_D_08 SEQ ID NO:1060, CaF1_WIE_07_G_01 SEQ ID NO:1084, CaF1_WIE_07_G_05 SEQ ID NO:1088, CaF1_WIE_08_A_05 SEQ ID NO:1105, CaF1_WIE_08_A_06 SEQ ID NO:1106, CaF1_WIE_08_A_07 SEQ ID NO:1107, CaF1_WIE_08_B_03 SEQ ID NO:1110, CaF1_WIE_08_D_04 SEQ ID NO:1132, CaF1_WIE_08_E_05 SEQ ID NO:1141, CaF1_WIE_08_G_07 SEQ ID NO:1160, CaF1_WIE_09_A_06 SEQ ID NO:1177, CaF1_WIE_09_D_03 SEQ ID NO:1193, CaF1_WIE_09_E_06 SEQ ID NO:1203, CaF1_WIE_09_F_01 SEQ ID NO:1209, CaF1_WIE_09_G_09 SEQ ID NO:1224, CaF1_WIE_09_H_01 SEQ ID NO:1226, CaF1_WIE_09_H_05 SEQ ID NO:1228, CaF1_WIE_09_H_10 SEQ ID NO:1232, CaF1_WIE_10_A_09 SEQ ID NO:1241, CaF1_WIE_10_B_03 SEQ ID NO:1245, CaF1_WIE_10_13105 SEQ ID NO:1247, CaF1_WIE_10_B_06 SEQ ID NO:1248, CaF1_WIE_10_B_11 SEQ ID NO:1251, CaF1_WIE_10_C_06 SEQ ID NO:1256, CaF1_WIE_10_D_08 SEQ ID NO:1267, CaF1_WIE_10_D_11 SEQ ID NO:1270, CaF1_WIE_10_E_08 SEQ ID NO:3278, CaF1_WIE_10_F_02 SEQ ID NO:3281, CaF1_WIE_10_F_10 SEQ ID NO:3288, CaF1_WIE_10_G_11 SEQ ID NO:3297, CaF1_WIE_11_A_01 SEQ ID NO:3308, CaF1_WIE_11_A_10 SEQ ID NO:3315, CaF1_WIE_11_A_11 SEQ ID NO:3316, CaF1_WIE_11_C_01 SEQ ID NO:3326, CaF1_WIE_11_C_08 SEQ ID NO:3332, CaF1_WIE_11_D_01 SEQ ID NO:3335, CaF1_WIE_11_E_04 SEQ ID NO:3346, CaF1_WIE_11_F_05 SEQ ID NO:3353, CaF1_WIE_11_H_04 SEQ ID NO:3363, CaF1_WIE_11_G_05 SEQ ID NO:3364, CaF1_WIE_11_H_03 SEQ ID NO:3370, CaF1_WIE_11_H_06 SEQ ID NO:3372, CaF1_WIE_12_A_02 SEQ ID NO:3378, CaF1_WIE_12_C_06 SEQ ID NO:3399, CaF1_WIE_12_D_02 SEQ ID NO:3404, CaF1_WIE_12_D_03 SEQ ID NO:3405, CaF1_WIE_12_E_04 SEQ ID NO:3414, CaF1_WIE_12_F_01 SEQ ID NO:3421, CaF1_WIE_12_F_10 SEQ ID NO:3429, CaF1_WIE_12_G_05 SEQ ID NO:3435, CaF1_WIE_12_G_07 SEQ ID NO:3437, CaF1_WIE_12_H_07 SEQ ID NO:3447, CaF1_WIE_13_A_01 SEQ ID NO:3452, CaF1_WIE_13_A_02 SEQ ID NO:3453, CaF1_WIE_13_A_09 SEQ ID NO:3458, CaF1_WIE_13_C_02 SEQ ID NO:3470, CaF1_WIE_13_C_07 SEQ ID NO:3474, CaF1_WIE_13_D_01 SEQ ID NO:3479, CaF1_WIE_13_F_04 SEQ ID NO:3500, CaF1_WIE_13_F_05 SEQ ID NO:3501, CaF1_WIE_13_F_07 SEQ ID NO:3503, CaF1_WIE_13_G_01 SEQ ID NO:3506, CaF1_WIE_13_H_09 SEQ ID NO:3521, CaF1_WIE_14_A_11 SEQ ID NO:3526, CaF1_WIE_14_C_06 SEQ ID NO:3532, CaF1_WIE_14_D_02 SEQ ID NO:3537, CaF1_WIE_14_D_10 SEQ ID NO:3541, CaF1_WIE_14_E_03 SEQ ID NO:3543, CaF1_WIE_15_A_02 SEQ ID NO:3563, CaF1_WIE_15_A_04 SEQ ID NO:3564, CaF1_WIE_15_A_06 SEQ ID NO:3566, CaF1_WIE_15_B_05 SEQ ID NO:3572, CaF1_WIE_15_C_01 SEQ ID NO:3574, CaF1_WIE_15_C_02 SEQ ID NO:3575, CaF1_WIE_15_C_06 SEQ ID NO:3577, CaF1_WIE_15_C_08 SEQ ID NO:3578, CaF1_WIE_15_D_04 SEQ ID NO:3579, CaF1_WIE_15_E_01 SEQ ID NO:3582, CaF1_WIE_15_E_09 SEQ ID NO:3586, CaF1_WIE_15_F_07 SEQ ID NO:3589, CaF1_WIE_15_H_02 SEQ ID NO:3594, CaF1_WIE_16_A_08 SEQ ID NO:3601, CaF1_WIE_16_B_03 SEQ ID NO:3604, CaF1_WIE_16_B_09 SEQ ID NO:3609, CaF1_WIE_16_B_11 SEQ ID NO:3611, CaF1_WIE_16_C_03 SEQ ID NO:3612, CaF1_WIE_16_D_03 SEQ ID NO:3617, CaF1_WIE_16_D_11 SEQ ID NO:3619, CaF1_WIE_16_F_11 SEQ ID NO:3629, CaF1_WIE_16_G_04 SEQ ID NO:3632, CaF1_WIE_16_H_01 SEQ ID NO:3637, CaF1_WIE_16_H_04 SEQ ID NO:3638, CaF1_WIE_16_H_10 SEQ ID NO:3642, CaF1_WIE_17_A_09 SEQ ID NO:3652, CaF1_WIE_17_C_06 SEQ ID NO:3669, CaF1_WIE_17_C_07 SEQ ID NO:3670, CaF1_WIE_17_C_08 SEQ ID NO:3671, CaF1_WIE_17_C_11 SEQ ID NO:3674, CaF1_WIE_17_D_01 SEQ ID NO:3675, CaF1_WIE_17_D_09 SEQ ID NO:3681, CaF1_WIE_17_E_03 SEQ ID NO:3686, CaF1_WIE_17_E_05 SEQ ID NO:3688, CaF1_WIE_17_F_01 SEQ ID NO:3695, CaF1_WIE_17_F_03 SEQ ID NO:3697, CaF1_WIE_17_G_09 SEQ ID NO:3712, CaF1_WIE_17_H_02 SEQ ID NO:3716, CaF1_WIE_18_A_11 SEQ ID NO:3732, CaF1_WIE_18_B_01 SEQ ID NO:3733, CaF1_WIE_18_B_05 SEQ ID NO:3736, CaF1_WIE_18_C_03 SEQ ID NO:3743, CaF1_WIE_18_D_07 SEQ ID NO:3755, CaF1_WIE_18_E_11 SEQ ID NO:3769, CaF1_WIE_18_F_09 SEQ ID NO:3777, CaF1_WIE_18_F_11 SEQ ID NO:3779, CaF1_WIE_19_A_05 SEQ ID NO:3800, CaF1_WIE_19_A_10 SEQ ID NO:3804, CaF1_WIE_19_A_11 SEQ ID NO:3805, CaF1_WIE_19_B_02 SEQ ID NO:3807, CaF1_WIE_19_C_10 SEQ ID NO:3821, CaF1_WIE_19_E_05 SEQ ID NO:3831, CaF1_WIE_19_E_06 SEQ ID NO:3832, CaF1_WIE_19_F_07 SEQ ID NO:3842, CaF1_WIE_19_G_01 SEQ ID NO:3847, CaF1_WIE_19_H_10 SEQ ID NO:3860, CaF1_WIE_20_B_08 SEQ ID NO:3869, CaF1_WIE_20_D_05 SEQ ID NO:3879, CaF1_WIE_20_E_04 SEQ ID NO:3886, CaF1_WIE_20_E_07 SEQ ID NO:3889, CaF1_WIE_20_F_02 SEQ ID NO:3893, CaF1_WIE_20_G_02 SEQ ID NO:3900, CaF1_WIE_20_G_05 SEQ ID NO:3902, CaF1_WIE_21_A_04 SEQ ID NO:3918, CaF1_WIE_21_B_04 SEQ ID NO:3925,

CaF1_WIE_21_B_06 SEQ ID NO:3926, CaF1_WIE_21_B_09 SEQ ID NO:3928, CaF1_WIE_21_B_11 SEQ ID NO:3930, CaF1_WIE_21_D_04 SEQ ID NO:3941, CaF1_WIE_21_D_09 SEQ ID NO:3943, CaF1_WIE_21_E_07 SEQ ID NO:3949, CaF1_WIE_21_F_02 SEQ ID NO:3953, CaF1_WIE_21_F_03 SEQ ID NO:3954, CaF1_WIE_21_F_07 SEQ ID NO:3956, CaF1_WIE_21_G_02 SEQ ID NO:3961, CaF1_WIE_21_G_03 SEQ ID NO:3962, CaF1_WIE_21_G_04 SEQ ID NO:3963, CaF1_WIE_21_G_05 SEQ ID NO:3964, CaF1_WIE_21_G_09 SEQ ID NO:3967, CaF1_WIE_21_H_01 SEQ ID NO:3970, CaF1_WIE_21_H_02 SEQ ID NO:3971, CaF1_WIE_22_A_03 SEQ ID NO:3979, CaF1_WIE_22_A_08 SEQ ID NO:3982, CaF1_WIE_22_F_01 SEQ ID NO:4008, CaF1_WIE_22_G_06 SEQ ID NO:4017, CaF1_WIE_22_H_03 SEQ ID NO:4021, CaF1_WIE_22_H_10 SEQ ID NO:4028, CaF1_WIE_23_A_04 SEQ ID NO:4031, CaF1_WIE_23_B_05 SEQ ID NO:4038, CaF1_WIE_23_B_10 SEQ ID NO:4041, CaF1_WIE_23_D_07 SEQ ID NO:4049, CaF1_WIE_23_D_10 SEQ ID NO:4052, CaF1_WIE_23_F_09 SEQ ID NO:4067, CaF1_WIE_23_G_02 SEQ ID NO:4071, CaF1_WIE_23_H_01 SEQ ID NO:4080, CaF1_WIE_23_H_04 SEQ ID NO:4082, CaF1_WIE_23_H_07 SEQ ID NO:4084, CaF1_WIE_24_E_02 SEQ ID NO:4121, CaF1_WIE_24_F_01 SEQ ID NO:4128, CaF1_WIE_24_H_01 SEQ ID NO:4149, CaF1_WIE_24_H_04 SEQ ID NO:4152, CaF1_WIE_24_H_07 SEQ ID NO:4155, CaF1_WIE_24_H_08 SEQ ID NO:4156, CaF1_WIE_25_A_09 SEQ ID NO:4165, CaF1_WIE_25_A_10 SEQ ID NO:4166, CaF1_WIE_25_C_02 SEQ ID NO:4177, CaF1_WIE_25_C_05 SEQ ID NO:4179, CaF1_WIE_25_D_05 SEQ ID NO:4189, CaF1_WIE_25_D_08 SEQ ID NO:4192, CaF1_WIE_25_F_02 SEQ ID NO:4205, CaF1_WIE_25_F_08 SEQ ID NO:4207, CaF1_WIE_25_G_11 SEQ ID NO:4216, CaF1_WIE_26_A_10 SEQ ID NO:4231, CaF1_WIE_26_C_05 SEQ ID NO:4246, CaF1_WIE_26_C_08 SEQ ID NO:4249, CaF1_WIE_26_C_09 SEQ ID NO:4250, CaF1_WIE_26_D_01 SEQ ID NO:4252, CaF1_WIE_26_D_03 SEQ ID NO:4254, CaF1_WIE_26_D_06 SEQ ID NO:4256, CaF1_WIE_26_E_01 SEQ ID NO:4262, CaF1_WIE_26_E_02 SEQ ID NO:4263, CaF1_WIE_26_F_08 SEQ ID NO:4275, CaF1_WIE_26_G_01 SEQ ID NO:4277, CaF1_WIE_26_G_02 SEQ ID NO:4278, CaF1_WIE_26_G_10 SEQ ID NO:4286, CaF1_WIE_27_D_10 SEQ ID NO:4336, CaF1_WIE_27_E_01 SEQ ID NO:4338, CaF1_WIE_27_F_11 SEQ ID NO:4358, CaF1_WIE_27_G_08 SEQ ID NO:4366, CaF1_WIE_28_A_04 SEQ ID NO:4380, CaF1_WIE_28_A_07 SEQ ID NO:4383, CaF1_WIE_28_B_04 SEQ ID NO:4388, CaF1_WIE_28_C_01 SEQ ID NO:4393, CaF1_WIE_28_D_01 SEQ ID NO:4403, CaF1_WIE_28_E_06 SEQ ID NO:4416, CaF1_WIE_28_E_07 SEQ ID NO:4417, CaF1_WIE_28_E_08 SEQ ID NO:4418, CaF1_WIE_28_E_11 SEQ ID NO:4419, CaF1_WIE_28_G_03 SEQ ID NO:4428, CaF1_WIE_28_G_04 SEQ ID NO:4429, CaF1_WIE_28_G_08 SEQ ID NO:4433, CaF1_WIE_28_G_11 SEQ ID NO:4435, CaF1_WIE_28_H_06 SEQ ID NO:4440, CaF1_WIE_28_H_07 SEQ ID NO:4441, CaF1_WIE_29_A_05 SEQ ID NO:4449, CaF1_WIE_29_C_11 SEQ ID NO:4477, CaF1_WIE_29_D_06 SEQ ID NO:4483, CaF1_WIE_29_E_04 SEQ ID NO:4491, CaF1_WIE_29_F_07 SEQ ID NO:4505, CaF1_WIE_29_F_11 SEQ ID NO:4509, CaF1_WIE_29_G_04 SEQ ID NO:4513, CaF1_WIE_29_H_01 SEQ ID NO:4521, CaF1_WIE_29_H_03 SEQ ID NO:4523, CaF1_WIE_29_H_06 SEQ ID NO:4525, CaF1_WIE_29_H_08 SEQ ID NO:4527, CaF1_WIE_30_A_03 SEQ ID NO:4533, CaF1_WIE_30_A_06 SEQ ID NO:4534, CaF1_WIE_30_A_08 SEQ ID NO:4536, CaF1_WIE_30_C_03 SEQ ID NO:4549, CaF1_WIE_30_E_04 SEQ ID NO:4568, CaF1_WIE_30_E_05 SEQ ID NO:4569, CaF1_WIE_30_F_06 SEQ ID NO:4578, CaF1_WIE_30_G_03 SEQ ID NO:4586, CaF1_WIE_30_G_07 SEQ ID NO:4590, CaF1_WIE_30_G_09 SEQ ID NO:4592, CaF1_WIE_30_H_04 SEQ ID NO:4596, CaF1_WIE_31_A_05 SEQ ID NO:4605, CaF1_WIE_31_A_06 SEQ ID NO:4606, CaF1_WIE_31_B_02 SEQ ID NO:4612, CaF1_WIE_31_C_06 SEQ ID NO:4624, CaF1_WIE_31_D_01 SEQ ID NO:4628, CaF1_WIE_31_D_04 SEQ ID NO:4629, CaF1_WIE_31_D_05 SEQ ID NO:4630, CaF1_WIE_31_F_03 SEQ ID NO:4647, CaF1_WIE_31_F_08 SEQ ID NO:4651, CaF1_WIE_31_H_03 SEQ ID NO:4665, CaF1_WIE_31_H_04 SEQ ID NO:4666, CaF1_WIE_32_A_02 SEQ ID NO:4672, CaF1_WIE_32_A_03 SEQ ID NO:4673, CaF1_WIE_32_B_06 SEQ ID NO:4686, CaF1_WIE_32_C_01 SEQ ID NO:4692, CaF1_WIE_32_C_08 SEQ ID NO:4698, CaF1_WIE_32_F_10 SEQ ID NO:4722, CaF1_WIE_32_F_11 SEQ ID NO:4723, CaF1_WIE_32_G_03 SEQ ID NO:4726, CaF1_WIE_32_G_06 SEQ ID NO:4729, CaF1_WIE_32_H_02 SEQ ID NO:4736, CaF1_WIE_32_H_04 SEQ ID NO:4738, CaF1_WIE_33_A_05 SEQ ID NO:4749, CaF1_WIE_33_B_09 SEQ ID NO:4759, CaF1_WIE_33_C_02 SEQ ID NO:4761, CaF1_WIE_33_C_03 SEQ ID NO:4762, CaF1_WIE_33_C_04 SEQ ID NO:4763, CaF1_WIE_33_C_07 SEQ ID NO:4766, CaF1_WIE_33_D_06 SEQ ID NO:4772, CaF1_WIE_33_E_10 SEQ ID NO:4783, CaF1_WIE_33_F_02 SEQ ID NO:4786, CaF1_WIE_33_F_03 SEQ ID NO:4787, CaF1_WIE_33_F_10 SEQ ID NO:4793, CaF1_WIE_33_G_03 SEQ ID NO:4796, CaF1_WIE_33_H_09 SEQ ID NO:4809, CaF1_WIE_34_B_08 SEQ ID NO:4825, CaF1_WIE_34_C_04 SEQ ID NO:4830, CaF1_WIE_34_C_09 SEQ ID NO:4833, CaF1_WIE_34_D_08 SEQ ID NO:4843, CaF1_WIE_34_E_01 SEQ ID NO:4847, CaF1_WIE_34_F_01 SEQ ID NO:4853, CaF1_WIE_34_F_02 SEQ ID NO:4854, CaF1_WIE_34_F_06 SEQ ID NO:4857, CaF1_WIE_34_G_02 SEQ ID NO:4863, CaF1_WIE_34_G_08 SEQ ID NO:4867, CaF1_WIE_34_G_09 SEQ ID NO:4868, CaF1_WIE_34_H_03 SEQ ID NO:4871, CaF1_WIE_35_A_08 SEQ ID NO:4884, CaF1_WIE_35_A_09 SEQ ID NO:4885, CaF1_WIE_35_B_01 SEQ ID NO:4887, CaF1_WIE_35_B_02 SEQ ID NO:4888, CaF1_WIE_35_C_06 SEQ ID NO:4902, CaF1_WIE_35_E_11 SEQ ID NO:4926, CaF1_WIE_35_G_07 SEQ ID NO:4942, CaF1_WIE_35_G_08 SEQ ID NO:4943, CaF1_WIE_35_G_09 SEQ ID NO:4944, CaF1_WIE_36_A_01 SEQ ID NO:4955, CaF1_WIE_36_A_03 SEQ ID NO:4957, CaF1_WIE_36_D_11 SEQ ID NO:4987, CaF1_WIE_36_E_01 SEQ ID NO:4988, CaF1_WIE_36_H_01 SEQ ID NO:5011, CaF1_WIE_36_H_03 SEQ ID NO:5013, CaF1_WIE_37_A_02 SEQ ID NO:5023, CaF1_WIE_37_B_10 SEQ ID NO:5037, CaF1_WIE_37_C_07 SEQ ID NO:5039, CaF1_WIE_37_D_01 SEQ ID NO:5043, CaF1_WIE_37_E_07 SEQ ID NO:5054, CaF1_WIE_37_F_10 SEQ ID NO:5064, CaF1_WIE_37_F_11 SEQ ID NO:5065, CaF1_WIE_38_C_03 SEQ ID NO:5102, CaF1_WIE_38_F_07 SEQ ID NO:5126, CaF1_WIE_38_G_05 SEQ ID NO:5132, CaF1_WIE_38_H_01 SEQ ID NO:5137, CaF1_WIE_39_A_03 SEQ ID NO:5146, CaF1_WIE_39_C_09 SEQ ID NO:5168, CaF1_WIE_40_B_05 SEQ ID NO:5212, CaF1_WIE_40_B_08 SEQ ID NO:5214, CaF1_WIE_40_D_02 SEQ

ID NO:5226, CaF1_WIE_40_D_06 SEQ ID NO:5230, CaF1_WIE_40_D_07 SEQ ID NO:5231, CaF1_WIE_40_D_08 SEQ ID NO:5232, CaF1_WIE_40_D_11 SEQ ID NO:5235, CaF1_WIE_40_E_10 SEQ ID NO:5242, CaF1_WIE_40_H_01 SEQ ID NO:5263, CaF1_WIE_41_C_06 SEQ ID NO:5293, CaF1_WIE_41_D_04 SEQ ID NO:5299, CaF1_WIE_41_D_09 SEQ ID NO:5303, CaF1_WIE_41_F_01 SEQ ID NO:5314, CaF1_WIE_41_F_05 SEQ ID NO:5317, CaF1_WIE_41_H_05 SEQ ID NO:5334, CaF1_WIE_42_A_02 SEQ ID NO:5341, CaF1_WIE_42_A_07 SEQ ID NO:5345, CaF1_WIE_42_C_01 SEQ ID NO:5352, CaF1_WIE_42_C_04 SEQ ID NO:5354, CaF1_WIE_42_C_11 SEQ ID NO:5360, CaF1_WIE_42_E_02 SEQ ID NO:5367, CaF1_WIE_42_E_04 SEQ ID NO:5369, CaF1_WIE_42_G_02 SEQ ID NO:5380, CaF1_WIE_43_B_01 SEQ ID NO:5397, CaF1_WIE_43_B_02 SEQ ID NO:5398, CaF1_WIE_43_B_06 SEQ ID NO:5401, CaF1_WIE_43_C_10 SEQ ID NO:5409, CaF1_WIE_43_D_05 SEQ ID NO:5413, CaF1_WIE_43_D_09 SEQ ID NO:5416, CaF1_WIE_43_E_02 SEQ ID NO:5419, CaF1_WIE_43_E_05 SEQ ID NO:5421, CaF1_WIE_43_E_10 SEQ ID NO:5423, CaF1_WIE_43_H_02 SEQ ID NO:5439, CaF1_WIE_44_C_02 SEQ ID NO:5455, CaF1_WIE_44_D_02 SEQ ID NO:5465, CaF1_WIE_44_D_05 SEQ ID NO:5468, CaF1_WIE_44_F_03 SEQ ID NO:5482, CaF1_WIE_44_G_01 SEQ ID NO:5487, CaF1_WIE_44_G_11 SEQ ID NO:5493, CaF1_WIE_45_A_09 SEQ ID NO:5509, CaF1_WIE_45_B_02 SEQ ID NO:5512, CaF1_WIE_45_C_03 SEQ ID NO:5520, CaF1_WIE_45_C_09 SEQ ID NO:5523, CaF1_WIE_45_E_02 SEQ ID NO:5530, CaF1_WIE_45_E_05 SEQ ID NO:5532, CaF1_WIE_45_E_10 SEQ ID NO:5536, CaF1_WIE_45_G_03 SEQ ID NO:5545, CaF1_WIE_45_G_05 SEQ ID NO:5547, CaF1_WIE_45_G_06 SEQ ID NO:5548, CaF1_WIE_45_H_05 SEQ ID NO:5557, CaF1_WIE_45_H_09 SEQ ID NO:5561, CaF1_WIE_46_C_10 SEQ ID NO:5589, CaF1_WIE_46_D_10 SEQ ID NO:5597, CaF1_WIE_46_D_11 SEQ ID NO:5598, CaF1_WIE_46_F_09 SEQ ID NO:5615, CaF1_WIE_46_F_11 SEQ ID NO:5616, CaF1_WIE_46_H_10 SEQ ID NO:5632, CaF1_WIE_47_A_05 SEQ ID NO:5636, CaF1_WIE_47_A_10 SEQ ID NO:5641, CaF1_WIE_47_A_11 SEQ ID NO:5642, CaF1_WIE_47_B_04 SEQ ID NO:5645, CaF1_WIE_47_B_09 SEQ ID NO:5649, CaF1_WIE_47_F_01 SEQ ID NO:5680, CaF1_WIE_47_F_10 SEQ ID NO:5688, CaF1_WIE_47_G_01 SEQ ID NO:5690, CaF1_WIE_47_G_05 SEQ ID NO:5694, CaF1_WIE_48_A_10 SEQ ID NO:5715, CaF1_WIE_48_B_03 SEQ ID NO:5717, CaF1_WIE_48_C_04 SEQ ID NO:5726, CaF1_WIE_48_D_01 SEQ ID NO:5732, CaF1_WIE_48_D_02 SEQ ID NO:5733, CaF1_WIE_48_D_04 SEQ ID NO:5735, CaF1_WIE_48_E_01 SEQ ID NO:5740, CaF1_WIE_48_E_05 SEQ ID NO:5744, CaF1_WIE_48_F_02 SEQ ID NO:5751, CaF1_WIE_48_G_10 SEQ ID NO:5764, CaF1_WIE_49_A_10 SEQ ID NO:5782, CaF1_WIE_49_B_08 SEQ ID NO:5789, CaF1_WIE_49_C_05 SEQ ID NO:5796, CaF1_WIE_49_D_11 SEQ ID NO:5806, CaF1_WIE_49_E_11 SEQ ID NO:5813, CaF1_WIE_49_F_01 SEQ ID NO:5814, CaF1_WIE_49_F_04 SEQ ID NO:5816, CaF1_WIE_49_F_08 SEQ ID NO:5818, CaF1_WIE_50_B_10 SEQ ID NO:5847, CaF1_WIE_50_C_01 SEQ ID NO:5849, CaF1_WIE_50_C_09 SEQ ID NO:5854, CaF1_WIE_50_D_03 SEQ ID NO:5857, CaF1_WIE_50_D_11 SEQ ID NO:5864, CaF1_WIE_50_E_01 SEQ ID NO:5865, CaF1_WIE_50_E_10 SEQ ID NO:5872, CaF1_WIE_50_F_11 SEQ ID NO:5881, CaF1_WIE_50_G_05 SEQ ID NO:5883, CaF1_WIE_50_H_10 SEQ ID NO:5895, CaF1_WIE_51_A_04 SEQ ID NO:5898, CaF1_WIE_51_A_08 SEQ ID NO:5902, CaF1_WIE_51_B_04 SEQ ID NO:5908, CaF1_WIE_51_B_06 SEQ ID NO:5909, CaF1_WIE_51_B_07 SEQ ID NO:5910, CaF1_WIE_51_B_08 SEQ ID NO:5911, CaF1_WIE_51_B_10 SEQ ID NO:5912, CaF1_WIE_51_F_07 SEQ ID NO:5944, CaF1_WIE_51_G_04 SEQ ID NO:5948, CaF1_WIE_51_H_11 SEQ ID NO:5956, CaF1_WIE_52_A_05 SEQ ID NO:5960, CaF1_WIE_52_B_01 SEQ ID NO:5965, CaF1_WIE_52_C_07 SEQ ID NO:5981, CaF1_WIE_52_C_11 SEQ ID NO:5983, CaF1_WIE_52_D_01 SEQ ID NO:5984, CaF1_WIE_52_D_06 SEQ ID NO:5987, CaF1_WIE_52_E_06 SEQ ID NO:5996, CaF1_WIE_52_F_11 SEQ ID NO:6007, CaF1_WIE_52_G_01 SEQ ID NO:6008, CaF1_WIE_52_G_05 SEQ ID NO:6012, CaF1_WIE_52_H_01 SEQ ID NO:6018, CaF1_WIE_52_H_04 SEQ ID NO:6020, CaF1_WIE_52_H_05 SEQ ID NO:6021, CaF1_WIE_52_H_06 SEQ ID NO:6022, CaF1_WIE_52_H_07 SEQ ID NO:6023, CaF1_WIE_53_A_01 SEQ ID NO:6027, CaF1_WIE_53_A_09 SEQ ID NO:6033, CaF1_WIE_53_C_02 SEQ ID NO:6043, CaF1_WIE_53_C_03 SEQ ID NO:6044, CaF1_WIE_53_C_10 SEQ ID NO:6050, CaF1_WIE_53_F_01 SEQ ID NO:6065, CaF1_WIE_53_H_08 SEQ ID NO:6079, CaF1_WIE_54_A_05 SEQ ID NO:6085, CaF1_WIE_54_C_10 SEQ ID NO:6107, CaF1_WIE_54_D_02 SEQ ID NO:6110, CaF1_WIE_54_E_02 SEQ ID NO:6121, CaF1_WIE_54_E_04 SEQ ID NO:6123, CaF1_WIE_54_E_05 SEQ ID NO:6124, CaF1_WIE_54_G_01 SEQ ID NO:6139, CaF1_WIE_54_G_04 SEQ ID NO:6141, CaF1_WIE_54_H_10 SEQ ID NO:6152, CaF1_WIE_55_B_01 SEQ ID NO:6158, CaF1_WIE_55_C_04 SEQ ID NO:6168, CaF1_WIE_55_F_07 SEQ ID NO:6196, CaF1_WIE_55_G_03 SEQ ID NO:6201, CaF1_WIE_55_G_08 SEQ ID NO:6206, CaF1_WIE_55_G_09 SEQ ID NO:6207, CaF1_WIE_55_H_08 SEQ ID NO:6215, CaF1_WIE_55_H_09 SEQ ID NO:6216, CaF1_WIE_55_H_10 SEQ ID NO:6217, CaF1_WIE_56_B_08 SEQ ID NO:6230, CaF1_WIE_56_D_11 SEQ ID NO:6242, CaF1_WIE_56_E_05 SEQ ID NO:6245, CaF1_WIE_56_F_05 SEQ ID NO:6253, CaF1_WIE_56_F_07 SEQ ID NO:6255, CaF1_WIE_56_F_11 SEQ ID NO:6258, CaF1_WIE_56_G_06 SEQ ID NO:6261, CaF1_WIE_56_H_03 SEQ ID NO:6265, CaF1_WIE_56_H_04 SEQ ID NO:6266 and CaF1_WIE_56_H_06 SEQ ID NO:6268.

Genes Involved in Cellular Transport and Homeostasis

Stress-induced reorganization and spatial distribution of many key metabolites in plants require efficient transport machinery. It is well known that *Arabidopsis* has diverse array of genes for multi-efflux transport and response to stress signals, and rice has more secondary transporter genes for carbohydrate and nutrient transport (Nagata et al., 2008). Various transport associated genes were identified in this study. Of these, clathrin adaptor complexes and putative polyol transporter protein 4 were expressed in the susceptible genotype while multidrug resistance protein, Sec Y protein, ABC transporter family protein, Ctr copper transporter, SKS3 copper ion binding protein showed expression only in the resistant genotype. Although few of these transport associated proteins showed genotype specificity, others like general substrate transporter, intracellular chloride channel, phosphate transporter 5, were representative of both the genotypes. ABC transporters and multidrug resistance genes are known to function in plant defense, while the role of other above mentioned genes in plant defense is yet to be discovered. The chloride channel was reported to be activated by CDPK in guard cell whereas the chloride transporter has been found to be involved in hypo-osmotic turgor regulation. Further, polyol transporter was shown to be expressed during maturation of common plantain companion cells, though its role in plant defense remains to be ambiguous. These results suggest that transport of both organic and inorganic substances may play a crucial role in immune response.

Still another embodiment of the present invention provides ESTs derived from chickpea, wherein the ESTs are related to cellular Transport/inorganic ion transport and metabolism. These ESTs are CaF1_JIE_02_D_08 SEQ ID NO:104, CaF1_JIE_08_F_11 SEQ ID NO:575, CaF1_JIE_09_H_02 SEQ ID NO:1311, CaF1_JIE_11_B_07 SEQ ID NO:1371, CaF1_JIE_11_F_07 SEQ ID NO:1406, CaF1_JIE_13_A_04 SEQ ID NO:1479, CaF1_JIE_13_A_08 SEQ ID NO:1481, CaF1_JIE_13_H_01 SEQ ID NO:1515, CaF1_JIE_14_E_09 SEQ ID NO:1557, CaF1_JIE_15_G_09 SEQ ID NO:1638, CaF1_JIE_16_A_11 SEQ ID NO:1657, CaF1_JIE_17_F_07 SEQ ID NO:1755, CaF1_JIE_19_A_02 SEQ ID NO:1838, CaF1_JIE_24_F_11 SEQ ID NO:2274, CaF1_JIE_26_A_03 SEQ ID NO:2349, CaF1_JIE_26_D_04 SEQ ID NO:2374, CaF1_JIE_26_D_09 SEQ ID NO:2378, CaF1_JIE_26_F_04 SEQ ID NO:2391, CaF1_JIE_26_G_09 SEQ ID NO:2400, CaF1_JIE_27_C_09 SEQ ID NO:2431, CaF1_JIE_27_E_08 SEQ ID NO:2445, CaF1_JIE_28_C_09 SEQ ID NO:2486, CaF1_JIE_29_A_03 SEQ ID NO:2521, CaF1_JIE_31_B_07 SEQ ID NO:2627, CaF1_JIE_35_A_03 SEQ ID NO:2840, CaF1_JIE_36_B_04 SEQ ID NO:2901, CaF1_JIE_36_B_11 SEQ ID NO:2905, CaF1_JIE_36_H_10 SEQ ID NO:2946, CaF1_JIE_37_C_10 SEQ ID NO:2964, CaF1_JIE_38_E_05 SEQ ID NO:3031, CaF1_JIE_41_H_02 SEQ ID NO:3237, CaF1_WIE_02_H_09 SEQ ID NO:760, CaF1_WIE_03_D_08 SEQ ID NO:788, CaF1_WIE_05_E_06 SEQ ID NO:926, CaF1_WIE_06_E_03 SEQ ID NO:989, CaF1_WIE_08_C_09 SEQ ID NO:1127, CaF1_WIE_09_A_05 SEQ ID NO:1176, CaF1_WIE_09_H_11 SEQ ID NO:1233, CaF1_WIE_10_D_03 SEQ ID NO:1263, CaF1_WIE_15_B_01 SEQ ID NO:3569, CaF1_WIE_17_F_07 SEQ ID NO:3700, CaF1_WIE_17_F_10 SEQ ID NO:3703, CaF1_WIE_17_F_11 SEQ ID NO:3704, CaF1_WIE_18_C_02 SEQ ID NO:3742, CaF1_WIE_18_D_05 SEQ ID NO:3753, CaF1_WIE_19_A_07 SEQ ID NO:3801, CaF1_WIE_19_B_07 SEQ ID NO:3811, CaF1_WIE_19_F_05 SEQ ID NO:3840, CaF1_WIE_21_E_01 SEQ ID NO:3946, CaF1_WIE_21_E_08 SEQ ID NO:3950, CaF1_WIE_21_G_11 SEQ ID NO:3969, CaF1_WIE_22_F_07 SEQ ID NO:4012, CaF1_WIE_22_F_08 SEQ ID NO:4013, CaF1_WIE_23_F_07 SEQ ID NO:4065, CaF1_WIE_26_A_03 SEQ ID NO:4226, CaF1_WIE_26_B_05 SEQ ID NO:4236, CaF1_WIE_26_B_06 SEQ ID NO:4237, CaF1_WIE_26_D_04 SEQ ID NO:4255, CaF1_WIE_28_C_07 SEQ ID NO:4399, CaF1_WIE_28_D_07 SEQ ID NO:4408, CaF1_WIE_29_C_04 SEQ ID NO:4470, CaF1_WIE_29_C_07 SEQ ID NO:4473, CaF1_WIE_30_G_01 SEQ ID NO:4584, CaF1_WIE_32_A_04 SEQ ID NO:4674, CaF1_WIE_32_C_02 SEQ ID NO:4693, CaF1_WIE_32_G_09 SEQ ID NO:4732, CaF1_WIE_34_E_11 SEQ ID NO:4852, CaF1_WIE_35_C_01 SEQ ID NO:4897, CaF1_WIE_35_C_07 SEQ ID NO:4903, CaF1_WIE_35_D_03 SEQ ID NO:4909, CaF1_WIE_35_H_08 SEQ ID NO:4952, CaF1_WIE_37_A_11 SEQ ID NO:5029, CaF1_WIE_37_G_02 SEQ ID NO:5067, CaF1_WIE_37_H_02 SEQ ID NO:5075, CaF1_WIE_38_F_02 SEQ ID NO:5122, CaF1_WIE_38_F_08 SEQ ID NO:5127, CaF1_WIE_39_E_03 SEQ ID NO:5177, CaF1_WIE_40_E_04 SEQ ID NO:5237, CaF1_WIE_40_G_06 SEQ ID NO:5258, CaF1_WIE_42_D_03 SEQ ID NO:5363, CaF1_WIE_43_A_11 SEQ ID NO:5396, CaF1_WIE_45_A_04 SEQ ID NO:5504, CaF1_WIE_45_A_08 SEQ ID NO:5508, CaF1_WIE_46_F_05 SEQ ID NO:5611, CaF1_WIE_47_C_04 SEQ ID NO:5654, CaF1_WIE_47_D_07 SEQ ID NO:5665, CaF1_WIE_47_F_09 SEQ ID NO:5687, CaF1_WIE_47_G_10 SEQ ID NO:5699, CaF1_WIE_48_B_10 SEQ ID NO:5722, CaF1_WIE_48_F_05 SEQ ID NO:5754, CaF1_WIE_48_G_09 SEQ ID NO:5763, CaF1_WIE_50_B_01 SEQ ID NO:5838, CaF1_WIE_50_E_05 SEQ ID NO:5869, CaF1_WIE_51_C_05 SEQ ID NO:5918, CaF1_WIE_51_C_07 SEQ ID NO:5920, CaF1_WIE_51_D_04 SEQ ID NO:5927, CaF1_WIE_51_F_04 SEQ ID NO:5943, CaF1_WIE_51_G_10 SEQ ID NO:5950, CaF1_WIE_52_G_10 SEQ ID NO:6016, CaF1_WIE_53_F_04 SEQ ID NO:6068, CaF1_WIE_54_A_02 SEQ ID NO:6082, CaF1_WIE_55_G_02 SEQ ID NO:6200, CaF1_WIE_55_G_06 SEQ ID NO:6204, CaF1_WIE_56_B_11 SEQ ID NO:6232 and CaF1_WIE_56_G_07 SEQ ID NO:6262.

Genes Involved in Hormone Responses

Salicylic acid (SA), jasmonic acid (JA) and ethylene play key roles in developmental regulation and stress responses through cross communicating signal transduction pathways. These hormones accumulate in response to pathogen infection and in turn lead to the activation of distinct sets of defense related genes. We observed presence of ethylene signaling pathway genes, for example, ethylene responsive transcoactivator and putative ethylene response protein in the susceptible genotype while ethylene receptor was present only in the resistant genotype. Coronatine-insensitive 1 and BRU1 precursor which are associated with JA and brassinosteroid pathways respectively, were specific to the resistant genotype. In addition, we found auxin signaling related proteins, of which, auxin-responsive SAUR was found in both the genotypes but auxin-regulated dual specificity cytosolic kinase was present only in the resistant genotype. Aux/IAA protein, auxin-induced protein IAA12 and auxin-induced putative aldo/keto reductase family protein were found specifically in the susceptible genotype. Our future efforts would be the investigation of their possible role in plant immunity.

Still another embodiment of the present invention provides ESTs derived from chickpea, wherein the ESTs are related to Hormone responsive. These ESTs are CaF1_JIE_02_C_08 SEQ ID NO:94, CaF1_JIE_02_C_09 SEQ ID NO:95, CaF1_JIE_02_C_10 SEQ ID NO:96, CaF1_JIE_05_D_08 SEQ ID NO:326, CaF1_JIE_05_F_08 SEQ ID NO:348, CaF1_JIE_08_A_04 SEQ ID NO:518, CaF1_JIE_08_E_07 SEQ ID NO:562, CaF1_JIE_16_A_04 SEQ ID NO:1653, CaF1_JIE_16_B_08 SEQ ID NO:1662, CaF1_JIE_16_D_05 SEQ ID NO:1679, CaF1_JIE_16_H_07 SEQ ID NO:1712, CaF1_JIE_19_E_11 SEQ ID NO:1876, CaF1_JIE_19_F_07 SEQ ID NO:1882, CaF1_JIE_20_C_08 SEQ ID NO:1931, CaF1_JIE_21_E_09 SEQ ID NO:2033, CaF1_JIE_21_F_06 SEQ ID NO:2037, CaF1_JIE_21_F_07 SEQ ID NO:2038, CaF1_JIE_23_H_10 SEQ ID NO:2218, CaF1_JIE_24_E_05 SEQ ID NO:2260, CaF1_JIE_36_D_03 SEQ ID NO:2914, CaF1_JIE_36_H_03 SEQ ID NO:2941, CaF1_JIE_40_C_09 SEQ ID NO:3136, CaF1_JIE_41_C_11 SEQ ID NO:3200, CaF1_JIE_41_D_06 SEQ ID NO:3206, CaF1_WIE_05_A_10 SEQ ID NO:894, CaF1_WIE_06_F_05 SEQ ID NO:1000, CaF1_WIE_11_C_09 SEQ ID NO:3333, CaF1_WIE_11_G_03 SEQ ID NO:3362, CaF1_WIE_12_D_08 SEQ ID NO:3409, CaF1_WIE_16_B_08 SEQ ID NO:3608, CaF1_WIE_16_H_07 SEQ ID NO:3641, CaF1_WIE_20_H_03 SEQ ID NO:3908, CaF1_WIE_20_H_04 SEQ ID NO:3909, CaF1_WIE_23_G_03 SEQ ID NO:4072, CaF1_WIE_30_C_11 SEQ ID NO:4555, CaF1_WIE_44_D_01 SEQ ID NO:5464 and CaF1_WIE_55_E_01 SEQ ID NO:6182.

Genes Involved in Cell Cycle and DNA Metabolism

Cell division and cell cycle progression in plants is often altered in response to various environmental stresses. Many cell division and cell-cycle related proteins, for example, putative kinetochore, cell division protein FtsZ and cdc2MsF identified in this study were predominant in the resistant genotype suggesting pathostress responsive alterations of cell cycle in chickpea. Genes involved in DNA replication and repair like DNA repair protein RadA, putative polyprotein and putative gag-pol polyprotein were identified from susceptible genotype while putative helicase was common in both the genotypes. These findings are interesting because very little is known about the role of such genes in plant immune responses.

Still another embodiment of the present invention provides ESTs derived from chickpea, wherein the ESTs are related to cell cycle control and cell division. These ESTs are CaF1_JIE_04_F_11 SEQ ID NO: 269, CaF1_JIE_05_B_01 SEQ ID NO:299, CaF1_JIE_07_F_11 SEQ ID NO:493, CaF1_JIE_24_H_06 SEQ ID NO:2286, CaF1_JIE_24_H_07 SEQ ID NO:2287, CaF1_JIE_25_B_10 SEQ ID NO:2303, CaF1_JIE_36_E_10 SEQ ID NO:2927, CaF1_WIE_03_E_10 SEQ ID NO:797, CaF1_WIE_06_F_09 SEQ ID NO:1003, CaF1_WIE_07_B_01 SEQ ID NO:1034, CaF1_WIE_11_B_09 SEQ ID NO:3323, CaF1_WIE_17_F_08 SEQ ID NO:3701, CaF1_WIE_17_H_01 SEQ ID NO:3715, CaF1_WIE_19_E_10 SEQ ID NO:3835, CaF1_WIE_20_E_02 SEQ ID NO:3884, CaF1_WIE_25_B_10 SEQ ID NO:4176, CaF1_WIE_26_B_02 SEQ ID NO:4234, CaF1_WIE_28_B_06 SEQ ID NO:4390, CaF1_WIE_35_C_05 SEQ ID NO:4901, CaF1_WIE_40_A_08 SEQ ID NO:5205, CaF1_WIE_40_A_09 SEQ ID NO:5206, CaF1_WIE_42_H_02 SEQ ID NO:5384, CaF1_WIE_44_C_07 SEQ ID NO:5460, CaF1_WIE_45_A_10 SEQ ID NO:5510, CaF1_WIE_46_F_08 SEQ ID NO:5614, CaF1_WIE_48_E_11 SEQ ID NO:5749, CaF1_WIE_54_D_07 SEQ ID NO:6115, CaF1_WIE_54_E_01 SEQ ID NO:6120, CaF1_WIE_55_G_05 SEQ ID NO:6203 and CaF1_WIE_56_H_07 SEQ ID NO:6269.

Still another embodiment of the present invention provides ESTs derived from chickpea, wherein the ESTs are related to DNA replication, recombination and repair. These ESTs are CaF1_JIE_08_E_02 SEQ ID NO:557, CaF1_JIE_15_A_04 SEQ ID NO:1584, CaF1_JIE_15_B_04 SEQ ID NO:1593, CaF1_JIE_16_B_07 SEQ ID NO:1661, CaF1_JIE_27_G_08 SEQ ID NO:2461, CaF1_JIE_28_E_08 SEQ ID NO:2499, CaF1_JIE_39_C_02 SEQ ID NO:3069, CaF1_JIE_39_C_10 SEQ ID NO:3076, CaF1_JIE_39_D_02 SEQ ID NO:3078, CaF1_JIE_42_G_01 SEQ ID NO:3265 and CaF1_WIE_32_E_01 SEQ ID NO:4706.

Genes Involved in Development and Cytoskeletal Organization

The genes involved in development and cytoskeletal organization account for 1.24% of the total CaUnigene set. The candidate genes involved in development were those encoding enzymes associated with fruit ripening and senescence, and several storage proteins like albumin and agglutinin. Most of the genes in this class were identified in both the susceptible and resistant genotypes, however agglutinin was specific to the resistant one. While there have been reports on association of the processes of plant defense and senescence, the involvement of ripening related proteins has never been implicated in immune responses. Seed storage proteins like germin and albumin have been shown to be involved in stress responses, however, role of agglutinin in plant immunity is not known.

Cytoskeleton is thought to contribute to the establishment of effective barriers at the cell periphery against pathogen ingression. Substantiating this phenomenon, several structural proteins were identified that include actin, microtubule bundling polypeptide, and beta tubulin, besides genes associated with cytoskeletal reorganization like actin-depolymerizing factor and putative spindle disassembly related genes. Although actin was present in the genotypes, actin-depolymerizing factor and putative spindle disassembly related genes were specific to resistant genotype.

Still another embodiment of the present invention provides ESTs derived from chickpea, wherein the ESTs are related to Cytoskeleton. These ESTs are CaF1_JIE_09_A_04 SEQ ID NO:601, CaF1_JIE_09_H_01 SEQ ID NO:1310, CaF1_JIE_20_C_03 SEQ ID NO:1926, CaF1_JIE_40_B_07 SEQ ID NO:3125, CaF1_JIE_42_G_10 SEQ ID NO:3271, CaF1_WIE_01_C_03 SEQ ID NO:647, CaF1_WIE_05_H_02 SEQ ID NO:948, CaF1_WIE_16_A_11 SEQ ID NO:3603, CaF1_WIE_18_A_10 SEQ ID NO:3731, CaF1_WIE_25_G_08 SEQ ID NO:4214, CaF1_WIE_26_B_11 SEQ ID NO:4241, CaF1_WIE_26_G_08 SEQ ID NO:4284, CaF1_WIE_37_E_06 SEQ ID NO:5053, CaF1_WIE_40_D_04 SEQ ID NO:5228, CaF1_WIE_41_B_01 SEQ ID NO:5281, CaF1_WIE_41_E_04 SEQ ID NO:5309, CaF1_WIE_42_C_07 SEQ ID NO:5357, CaF1_WIE_43_B_03 SEQ ID NO:5399, CaF1_WIE_43_C_03 SEQ ID NO:5406, CaF1_WIE_46_D_04 SEQ ID NO:5593, CaF1_WIE_48_E_08 SEQ ID NO:5746, CaF1_WIE_48_E_09 SEQ ID NO:5747, CaF1_WIE_48_G_05 SEQ ID NO:5761, CaF1_WIE_48_H_08 SEQ ID NO:5771, CaF1_WIE_52_G_03 SEQ ID NO:6010, CaF1_WIE_53_E_05 SEQ ID NO:6061 and CaF1_WIE_53_E_09 SEQ ID NO:6063

Still another embodiment of the present invention provides ESTs derived from chickpea, wherein the ESTs are related to development/storage/dormancy and senescence. These ESTs are CaF1_JIE_06_E_08 SEQ ID NO:408, CaF1_JIE_19_C_08 SEQ ID NO:1858, CaF1_JIE_19_C_09 SEQ ID NO:1859, CaF1_JIE_22_B SEQ ID NO:2077, CaF1_JIE_22_B_07 SEQ ID NO:2078, CaF1_JIE_22_F_09 SEQ ID NO:2117, CaF1_JIE_23_E_06 SEQ ID NO:2184, CaF1_JIE_25_A_02 SEQ ID NO:2291, CaF1_JIE_25_C_03 SEQ ID NO:2305, CaF1_JIE_27_G_02 SEQ ID NO:2458, CaF1_JIE_35_B_02 SEQ ID NO:2845, CaF1_JIE_40_F_02 SEQ ID NO:3155, CaF1_JIE_42_A_04 SEQ ID NO:3245, CaF1_WIE_01_E_09 SEQ ID NO:671, CaF1_WIE_02_A_05 SEQ ID NO:702, CaF1_WIE_02_C_05 SEQ ID NO:717, CaF1_WIE_03_E_09 SEQ ID NO:796, CaF1_WIE_04_B_11 SEQ ID NO:835, CaF1_WIE_04_D_09 SEQ ID NO:850, CaF1_WIE_04_H_01 SEQ ID NO:879, CaF1_WIE_06_E_08 SEQ ID NO:993, CaF1_WIE_07_B_03 SEQ ID NO:1036, CaF1_WIE_07_H_06 SEQ ID NO:1098, CaF1_WIE_07_H_09 SEQ ID NO:1100, CaF1_WIE_09_B_09 SEQ ID NO:1185, CaF1_WIE_09_B_10 SEQ ID NO:1186, CaF1_WIE_09_E_07 SEQ ID NO:1204, CaF1_WIE_09_E_10 SEQ ID NO:1207, CaF1_WIE_09_F_02 SEQ ID NO:1210, CaF1_WIE_11_B_01 SEQ ID NO:3317, CaF1_WIE_11_E_01 SEQ ID NO:3344, CaF1_WIE_12_B_02 SEQ ID NO:3385, CaF1_WIE_12_B_04 SEQ ID NO:3387, CaF1_WIE_12_F_11 SEQ ID NO:3430, CaF1_WIE_12_G_01 SEQ ID NO:3431, CaF1_WIE_12_G_11 SEQ ID NO:3441, CaF1_WIE_13_C_03 SEQ ID NO:3471, CaF1_WIE_13_C_09 SEQ ID NO:3476, CaF1_WIE_13_E_07 SEQ ID NO:3492, CaF1_WIE_13_E_09 SEQ ID NO:3494, CaF1_WIE_13_G_04 SEQ ID NO:3508, CaF1_WIE_14_G_11 SEQ ID NO:3557, CaF1_WIE_16_G_01 SEQ ID NO:3630, CaF1_WIE_17_B_04 SEQ ID NO:3658, CaF1_WIE_17_G_02 SEQ ID NO:3706, CaF1_WIE_17_G_03 SEQ ID NO:3707, CaF1_WIE_17_G_07 SEQ ID NO:3710, CaF1_WIE_17_G_11 SEQ ID NO:3714, CaF1_WIE_17_H_03 SEQ ID NO:3717, CaF1_WIE_18_A_05 SEQ ID NO:3726, CaF1_WIE_18_E_01 SEQ ID NO:3760, CaF1_WIE_18_E_06 SEQ ID NO:3764, CaF1_WIE_18_H_04 SEQ ID NO:3792, CaF1_WIE_18_H_10 SEQ ID NO:3795, CaF1_WIE_19_H_05 SEQ ID NO:3856, CaF1_WIE_19_H_06 SEQ ID NO:3857, CaF1_WIE_20_A_08 SEQ ID NO:3866, CaF1_WIE_20_C_04 SEQ ID NO:3873, CaF1_WIE_20_C_05 SEQ ID NO:3874, CaF1_WIE_20_D_03 SEQ ID NO:3877, CaF1_WIE_20_D_04 SEQ ID NO:3878, CaF1_WIE_20_E_05 SEQ ID NO:3887, CaF1_WIE_20_F_03 SEQ ID NO:3894, CaF1_WIE_21_B_03 SEQ ID NO:3924, CaF1_WIE_21_C_11 SEQ ID NO:3938, CaF1_WIE_23_A_09 SEQ ID NO:4034, CaF1_WIE_23_C_11 SEQ ID NO:4047, CaF1_WIE_23_F_04 SEQ ID NO:4063, CaF1_WIE_23_F_08 SEQ ID NO:4066, CaF1_WIE_24_A_08 SEQ ID NO:4093, CaF1_WIE_24_B_02 SEQ ID NO:4097, CaF1_WIE_24_C_03 SEQ ID NO:4106, CaF1_WIE_24_F_10 SEQ ID NO:4137, CaF1_WIE_25_A_11 SEQ ID NO:4167, CaF1_WIE_25_B_01 SEQ ID NO:4168, CaF1_WIE_25_C_03 SEQ ID NO:4178, CaF1_WIE_26_C_03 SEQ ID NO:4244, CaF1_WIE_27_A_02 SEQ ID NO:4300, CaF1_WIE_27_G_02 SEQ ID NO:4360, CaF1_WIE_28_B_05 SEQ ID NO:4389, CaF1_WIE_28_H_10 SEQ ID NO:4444, CaF1_WIE_29_A_01 SEQ ID NO:4445, CaF1_WIE_29_A_08 SEQ ID NO:4452, CaF1_WIE_29_G_03 SEQ ID NO:4512, CaF1_WIE_30_F_08 SEQ ID NO:4580, CaF1_WIE_31_B_10 SEQ ID NO:4618, CaF1_WIE_31_H_05 SEQ ID NO:4667, CaF1_WIE_32_B_08 SEQ ID NO:4688, CaF1_WIE_32_H_07 SEQ ID NO:4741, CaF1_WIE_33_C_05 SEQ ID NO:4764, CaF1_WIE_33_D_05 SEQ ID NO:4771, CaF1_WIE_33_E_11 SEQ ID NO:4784, CaF1_WIE_33_F_01 SEQ ID NO:4785, CaF1_WIE_34_A_09 SEQ ID NO:4817, CaF1_WIE_34_H_01 SEQ ID NO:4869, CaF1_WIE_35_B_09 SEQ ID NO:4895, CaF1_WIE_35_D_06 SEQ ID NO:4912, CaF1_WIE_35_E_01 SEQ ID NO:4917, CaF1_WIE_35_E_05 SEQ ID NO:4920, CaF1_WIE_35_G_03 SEQ ID NO:4938, CaF1_WIE_35_H_05 SEQ ID NO:4950, CaF1_WIE_36_D_09 SEQ ID NO:4985, CaF1_WIE_36_G_11 SEQ ID NO:5010, CaF1_WIE_37_B_04 SEQ ID NO:5032, CaF1_WIE_37_C_11 SEQ ID NO:5042, CaF1_WIE_37_D_03 SEQ ID NO:5045, CaF1_WIE_37_D_04 SEQ ID NO:5046, CaF1_WIE_38_B_04 SEQ ID NO:5095, CaF1_WIE_38_G_08 SEQ ID NO:5133, CaF1_WIE_39_C_03 SEQ ID NO:5162, CaF1_WIE_39_C_04 SEQ ID NO:5163, CaF1_WIE_39_G_11 SEQ ID NO:5190, CaF1_WIE_40_A_10 SEQ ID NO:5207, CaF1_WIE_40_C_04 SEQ ID NO:5220, CaF1_WIE_40_F_06 SEQ ID NO:5248, CaF1_WIE_41_C_09 SEQ ID NO:5296, CaF1_WIE_41_G_10 SEQ ID NO:5328, CaF1_WIE_41_G_11 SEQ ID NO:5329, CaF1_WIE_42_A_03 SEQ ID NO:5342, CaF1_WIE_42_B_03 SEQ ID NO:5348, CaF1_WIE_43_A_04 SEQ ID NO:5391, CaF1_WIE_43_D_06 SEQ ID NO:5414, CaF1_WIE_43_D_08 SEQ ID NO:5415, CaF1_WIE_44_A_07 SEQ ID NO:5446, CaF1_WIE_44_A_08 SEQ ID NO:5447, CaF1_WIE_44_D_04 SEQ ID NO:5467, CaF1_WIE_44_F_09 SEQ ID NO:5485, CaF1_WIE_45_D_03 SEQ ID NO:5525, CaF1_WIE_45_H_11 SEQ ID NO:5563, CaF1_WIE_46_G_04 SEQ ID NO:5618, CaF1_WIE_46_H_06 SEQ ID NO:5629, CaF1_WIE_47_H_08 SEQ ID NO:5707, CaF1_WIE_50_C_11 SEQ ID NO:5855, CaF1_WIE_50_F_10 SEQ ID NO:5880, CaF1_WIE_51_B_11 SEQ ID NO:5913, CaF1_WIE_51_C_03 SEQ ID NO:5916, CaF1_WIE_51_E_06 SEQ ID NO:5936, CaF1_WIE_51_E_08 SEQ ID NO:5938, CaF1_WIE_52_C_01 SEQ ID NO:5976, CaF1_WIE_52_C_02 SEQ ID NO:5977, CaF1_WIE_52_E_02 SEQ ID NO:5993, CaF1_WIE_53_B_07 SEQ ID NO:6039, CaF1_WIE_53_C_07 SEQ ID NO:6047, CaF1_WIE_53_E_03 SEQ ID NO:6060, CaF1_WIE_54_A_06 SEQ ID NO:6086, CaF1_WIE_54_D_06 SEQ ID NO:6114, CaF1_WIE_55_A_08 SEQ ID NO:6157, CaF1_WIE_55_C_09 SEQ ID NO:6173, CaF1_WIE_55_F_09 SEQ ID NO:6197 and CaF1_WIE_56_E_09 SEQ ID NO:6249.

Genes Involved in Cellular Redox and Energy Metabolism

The oxidative burst is one of the earliest cellular responses following successful pathogen recognition. Several enzymes involved in oxidative burst were identified in both susceptible and resistant genotypes that include peroxidase, superoxide dismutase, glutathione-S-transferase and quinone oxidoreductase. Apoplastic generation of superoxide or its dismutation product, hydrogen peroxide, has been shown in response to a variety of pathogens. These enzymes restrict the ROS-dependent damage and may lead to the activation of plant immune response.

Energy production has an impact on the overall metabolic state and the energy supply is the key factor for the maintenance of cell intactness under various stress conditions. We observed the presence of genes encoding different proteins involved in ATP biosynthesis like alternative NAD(P)H dehydrogenase and putative ADP, ATP carrier-like protein in susceptible genotype. However, alternative oxidase 2b and NADH dehydrogenase were identified in the resistant genotype only. Nevertheless, vacuolar H+-ATPase subunit A and ATP synthase beta subunit were common to both genotypes. While the involvement of these proteins in abiotic stress, energy conservation and maintenance of redox potential is well established, their exact role in plant immune response is yet to be elucidated.

Still another embodiment of the present invention provides ESTs derived from chickpea, wherein the ESTs are related to cellular redox state. These ESTs are CaF1_JIE_01_A_09 SEQ ID NO:7, CaF1_JIE_03_B_03 SEQ ID NO:151, CaF1_JIE_03_D_04 SEQ ID NO:167, CaF1_JIE_03_E_09 SEQ ID NO:180, CaF1_JIE_03_G_05 SEQ ID NO:196, CaF1_JIE_04_A_05 SEQ ID NO:213, CaF1_JIE_04_D_05 SEQ ID NO:244, CaF1_JIE_05_C_05 SEQ ID NO:313, CaF1_JIE_07_G_05 SEQ ID NO:498, CaF1_JIE_07_G_10 SEQ ID NO:503, CaF1_JIE_07_H_05 SEQ ID NO:509, CaF1_JIE_10_C_03 SEQ ID NO:1334, CaF1_JIE_10_G_03 SEQ ID NO:1346, CaF1_JIE_10_H_08 SEQ ID NO:1358, CaF1_JIE_11_B_10 SEQ ID NO:1374, CaF1_JIE_11_F_03 SEQ ID NO:1402, CaF1_JIE_15_A_05 SEQ ID NO:1585, CaF1_JIE_15_D_04 SEQ ID NO:1611, CaF1_JIE_15_E_10 SEQ ID NO:1624, CaF1_JIE_15_F_09 SEQ ID NO:1630, CaF1_JIE_16_B_11 SEQ ID NO:1665, CaF1_JIE_16_C_09 SEQ ID NO:1673, CaF1_JIE_16_E_10 SEQ ID NO:1690, CaF1_JIE_17_B_06 SEQ ID NO:1724, CaF1_JIE_17_D_09 SEQ ID NO:1742, CaF1_JIE_20_A_09 SEQ ID NO:1911, CaF1_JIE_20_G_05 SEQ ID NO:1969, CaF1_JIE_23_C_09 SEQ ID NO:2169, CaF1_JIE_23_H_07 SEQ ID NO:2216, CaF1_JIE_23_H_08 SEQ ID NO:2217, CaF1_JIE_24_A_09 SEQ ID NO:2228, CaF1_JIE_24_D_02 SEQ ID NO:2249, CaF1_JIE_24_F_04 SEQ ID NO:2269, CaF1_JIE_24_F_05 SEQ ID NO:2270, CaF1_JIE_25_A_06 SEQ ID NO:2294, CaF1_JIE_26_A_02 SEQ ID NO:2348, CaF1_JIE_26_B_10 SEQ ID NO:2361, CaF1_JIE_26_C_02 SEQ ID NO:2364, CaF1_JIE_26_F_06 SEQ ID NO:2392, CaF1_JIE_26_F_09 SEQ ID NO:2394, CaF1_JIE_27_H_07 SEQ ID NO:2465, CaF1_JIE_27_H_10 SEQ ID NO:2468, CaF1_JIE_28_B_04 SEQ ID NO:2476, CaF1_JIE_28_E_11 SEQ ID NO:2502, CaF1_JIE_28_H_06 SEQ ID NO:2515, CaF1_JIE_28_H_07 SEQ ID NO:2516, CaF1_JIE_28_H_10 SEQ ID NO:2519, CaF1_JIE_29_B_03 SEQ ID NO:2527, CaF1_JIE_29_C_09 SEQ ID NO:2537, CaF1_JIE_29_C_10 SEQ ID NO:2538, CaF1_JIE_31_G_02 SEQ ID NO:2659, CaF1_JIE_34_E_09 SEQ ID NO:2815, CaF1_JIE_34_E_10 SEQ ID NO:2816, CaF1_JIE_36_G_02 SEQ ID NO:2937, CaF1_JIE_36_H_06 SEQ ID NO:2943, CaF1_JIE_36_H_09 SEQ ID NO:2945, CaF1_JIE_37_C_07 SEQ ID NO:2962, CaF1_JIE_37_F_04 SEQ ID NO:2977, CaF1_JIE_37_G_07 SEQ ID NO:2985, CaF1_JIE_38_A_08 SEQ ID NO:3002, CaF1_JIE_38_B_04 SEQ ID NO:3008, CaF1_JIE_39_A_10 SEQ ID NO:3061, CaF1_JIE_40_B_05 SEQ ID NO:3124, CaF1_JIE_40_E_05 SEQ ID NO:3150, CaF1_JIE_41_A_05 SEQ ID NO:3183, CaF1_JIE_41_E_03 SEQ ID NO:3212, CaF1_WIE_01_D_05 SEQ ID NO:658, CaF1_WIE_01_D_11 SEQ ID NO:664, CaF1_WIE_01_F_05 SEQ ID NO:676, CaF1_WIE_02_A_08 SEQ ID NO:704, CaF1_WIE_02_A_09 SEQ ID NO:705, CaF1_WIE_02_F_07 SEQ ID NO:744, CaF1_WIE_02_08 SEQ ID NO:759, CaF1_WIE_03_D_09 SEQ ID NO:789, CaF1_WIE_03_F_01 SEQ ID NO:799, CaF1_WIE_04_C_09 SEQ ID NO:843, CaF1_WIE_04_E_06 SEQ ID NO:857, CaF1_WIE_04_G_05 SEQ ID NO:874, CaF1_WIE_05_B_09 SEQ ID NO:902, CaF1_WIE_05_E_09 SEQ ID NO:929, CaF1_WIE_06_D_10 SEQ ID NO:985, CaF1_WIE_06_E_10 SEQ ID NO:995, CaF1_WIE_06_H_02 SEQ ID NO:1015, CaF1_WIE_07_D_07 SEQ ID NO:1059, CaF1_WIE_08_B_02 SEQ ID NO:1109, CaF1_WIE_08_E_03 SEQ ID NO:1140, CaF1_WIE_09_E_04 SEQ ID NO:1201, CaF1_WIE_10_H_02 SEQ ID NO:3298, CaF1_WIE_11_C_02 SEQ ID NO:3327, CaF1_WIE_12_A_07 SEQ ID NO:3381, CaF1_WIE_12_F_06 SEQ ID NO:3425, CaF1_WIE_13_A_10 SEQ ID NO:3459, CaF1_WIE_13_C_01 SEQ ID NO:3469, CaF1_WIE_13_H_05 SEQ ID NO:3518, CaF1_WIE_15_A_08 SEQ ID NO:3567, CaF1_WIE_15_B_03 SEQ ID NO:3571, CaF1_WIE_15_D_05 SEQ ID NO:3580, CaF1_WIE_17_A_11 SEQ ID NO:3654, CaF1_WIE_17_B_01 SEQ ID NO:3655, CaF1_WIE_17_E_02 SEQ ID NO:3685, CaF1_WIE_17_G_04 SEQ ID NO:3708, CaF1_WIE_17_H_05 SEQ ID NO:3718, CaF1_WIE_18_B_08 SEQ ID NO:3738, CaF1_WIE_18_B_09 SEQ ID NO:3739, CaF1_WIE_18_D_06 SEQ ID NO:3754, CaF1_WIE_18_G_07 SEQ ID NO:3785, CaF1_WIE_19_E_01 SEQ ID NO:3829, CaF1_WIE_19_E_08 SEQ ID NO:3834, CaF1_WIE_21_H_10 SEQ ID NO:3976, CaF1_WIE_22_C_04 SEQ ID NO:3994, CaF1_WIE_22_H_08 SEQ ID NO:4026, CaF1_WIE_23_G_04 SEQ ID NO:4073, CaF1_WIE_24_D_04 SEQ ID NO:4115, CaF1_WIE_24_D_07 SEQ ID NO:4118, CaF1_WIE_24_E_05 SEQ ID NO:4123, CaF1_WIE_26_A_06 SEQ ID NO:4228, CaF1_WIE_26_H_11 SEQ ID NO:4298, CaF1_WIE_27_C_07 SEQ ID NO:4325, CaF1_WIE_27_C_08 SEQ ID NO:4326, CaF1_WIE_27_D_08 SEQ ID NO:4334, CaF1_WIE_28_A_10 SEQ ID NO:4386, CaF1_WIE_28_F_11 SEQ ID NO:4425, CaF1_WIE_29_A_07 SEQ ID NO:4451, CaF1_WIE_29_C_01 SEQ ID NO:4467, CaF1_WIE_30_A_02 SEQ ID NO:4532, CaF1_WIE_30_B_01 SEQ ID NO:4539, CaF1_WIE_30_B_09 SEQ ID NO:4545, CaF1_WIE_30_F_11 SEQ ID NO:4583, CaF1_WIE_31_B_04 SEQ ID NO:4613, CaF1_WIE_31_B_05 SEQ ID NO:4614, CaF1_WIE_31_G_08 SEQ ID NO:4660, CaF1_WIE_32_F_09 SEQ ID NO:4721, CaF1_WIE_32_H_05 SEQ ID NO:4739, CaF1_WIE_32_H_10 SEQ ID NO:4744, CaF1_WIE_33_A_01 SEQ ID NO:4746, CaF1_WIE_33_E_02 SEQ ID NO:4777, CaF1_WIE_33_H_06 SEQ ID NO:4808, CaF1_WIE_34_A_10 SEQ ID NO:4818, CaF1_WIE_34_B_04 SEQ ID NO:4821, CaF1_WIE_34_C_11 SEQ ID NO:4835, CaF1_WIE_34_H_05 SEQ ID NO:4873, CaF1_WIE_35_E_10 SEQ ID NO:4925, CaF1_WIE_36_H_10 SEQ ID NO:5020, CaF1_WIE_37_C_04 SEQ ID NO:5038, CaF1_WIE_37_C_09 SEQ ID NO:5040, CaF1_WIE_37_G_07 SEQ ID NO:5069, CaF1_WIE_38_A_02 SEQ ID NO:5084, CaF1_WIE_38_A_03 SEQ ID NO:5085, CaF1_WIE_38_A_04 SEQ ID NO:5086, CaF1_WIE_38_B_01 SEQ ID NO:5093, CaF1_WIE_38_B_02 SEQ ID NO:5094, CaF1_WIE_38_C_01 SEQ ID NO:5100, CaF1_WIE_38_C_02 SEQ ID NO:5101, CaF1_WIE_38_C_04 SEQ ID NO:5103, CaF1_WIE_38_D_01 SEQ ID NO:5110, CaF1_WIE_38_D_06 SEQ ID NO:5111, CaF1_WIE_38_E_01 SEQ ID NO:5116, CaF1_WIE_38_E_09 SEQ ID NO:5121, CaF1_WIE_38_F_03 SEQ ID NO:5123, CaF1_WIE_38_F_06 SEQ ID NO:5125, CaF1_WIE_38_G_09 SEQ ID NO:5134, CaF1_WIE_39_A_06 SEQ ID NO:5148, CaF1_WIE_39_A_07 SEQ ID NO:5149, CaF1_WIE_39_B_05 SEQ ID NO:5155, CaF1_WIE_39_B_06 SEQ ID NO:5156, CaF1_WIE_39_B_07 SEQ ID NO:5157, CaF1_WIE_39_C_06 SEQ ID NO:5165, CaF1_WIE_39_C_07 SEQ ID NO:5166, CaF1_WIE_39_D_04 SEQ ID NO:5171, CaF1_WIE_39_D_07 SEQ ID NO:5173, CaF1_WIE_39_E_06 SEQ ID NO:5178, CaF1_WIE_39_F_07 SEQ ID NO:5180, CaF1_WIE_41_A_10 SEQ ID NO:5279, CaF1_WIE_41_F_03 SEQ ID NO:5315, CaF1_WIE_41_G_07 SEQ ID NO:5326, CaF1_WIE_43_E_11 SEQ ID NO:5424, CaF1_WIE_43_F_04 SEQ ID NO:5428, CaF1_WIE_45_F_09 SEQ ID NO:5544, CaF1_WIE_46_D_01 SEQ ID NO:5590, CaF1_WIE_47_B_08 SEQ ID NO:5648, CaF1_WIE_47_F_11 SEQ ID NO:5689, CaF1_WIE_47_G_09 SEQ ID NO:5698, CaF1_WIE_48_B_01 SEQ ID NO:5716, CaF1_WIE_48_B_09 SEQ ID NO:5721, CaF1_WIE_48_C_02 SEQ ID NO:5725, CaF1_WIE_49_C_10 SEQ ID NO:5799, CaF1_WIE_49_E_10 SEQ ID NO:5812, CaF1_WIE_49_G_07 SEQ ID NO:5823, CaF1_WIE_50_B_08 SEQ ID NO:5845, CaF1_WIE_50_H_05 SEQ ID NO:5892, CaF1_WIE_52_A_10 SEQ ID NO:5963, CaF1_WIE_53_B_03 SEQ ID NO:6036, CaF1_WIE_54_C_05 SEQ ID NO:6103, CaF1_WIE_54_C_06 SEQ ID NO:6104, CaF1_WIE_54_E_07 SEQ ID NO:6126, CaF1_WIE_54_E_08 SEQ ID NO:6127, CaF1_WIE_54_F_01 SEQ ID NO:6130, CaF1_WIE_56_A_03 SEQ ID NO:6220, SEQ ID NO:6243 and CaF1_WIE_56_H_09 SEQ ID NO:6270.

Still another embodiment of the present invention provides ESTs derived from chickpea, wherein the ESTs are related to Energy production and conversion. These ESTs are CaF1_JIE_02_F_02 SEQ ID NO:116, CaF1_JIE_02_G_08 SEQ ID NO:130, CaF1_JIE_04_B_07 SEQ ID NO:226, CaF1_JIE_07_E_03 SEQ ID NO:477, CaF1_JIE_08_C_09 SEQ ID NO:543, CaF1_JIE_09_B_04 SEQ ID NO:611, CaF1_JIE_09_D_01 SEQ ID NO:627, CaF1_JIE_12_H_05 SEQ ID NO:1473, CaF1_JIE_13_A_05 SEQ ID NO:1480, CaF1_JIE_13_B_05 SEQ ID NO:1484, CaF1_JIE_16_G_11 SEQ ID NO:1707, CaF1_JIE_18_G_08 SEQ ID NO:1826, CaF1_JIE_18_H_04 SEQ ID NO:1832, CaF1_JIE_20_B_03 SEQ ID NO:1915, CaF1_JIE_24_D_06 SEQ ID NO:2253, CaF1_JIE_24_F_03 SEQ ID NO:2268, CaF1_JIE_26_C_09 SEQ ID NO:2369, CaF1_JIE_32_D_10 SEQ ID NO:2697, CaF1_JIE_32_H_06 SEQ ID NO:2719, CaF1_JIE_33_E_02 SEQ ID NO:2755, CaF1_JIE_33_G_04 SEQ ID NO:2768, CaF1_JIE_33_H_10 SEQ ID NO:2779, CaF1_JIE_34_A_04 SEQ ID NO:2783, CaF1_JIE_35_B_05 SEQ ID NO:2848, CaF1_JIE_36_F_03 SEQ ID NO:2930, CaF1_JIE_38_F_02 SEQ ID NO:3036, CaF1_JIE_39_D_08 SEQ ID NO:3081, CaF1_JIE_41_E_11 SEQ ID NO:3219, CaF1_WIE_01_A_04 SEQ ID NO:632, CaF1_WIE_02_C_07 SEQ ID NO:719, CaF1_WIE_02_E_01 SEQ ID NO:728, CaF1_WIE_02_E_07 SEQ ID NO:734, CaF1_WIE_03_B_07 SEQ ID NO:771, CaF1_WIE_03_D_02 SEQ ID NO:784, CaF1_WIE_05_C_06 SEQ ID NO:908, CaF1_WIE_06_G_06 SEQ ID NO:1009, CaF1_WIE_08_B_09 SEQ ID NO:1116, CaF1_WIE_08_D_02 SEQ ID NO:1130, CaF1_WIE_09_G_11 SEQ ID NO:1225, CaF1_WIE_10_A_05 SEQ ID NO:1238, CaF1_WIE_20_A_09 SEQ ID NO:3867, CaF1_WIE_20_F_09 SEQ ID NO:3898, CaF1_WIE_20_G_03 SEQ ID NO:3901, CaF1_WIE_22_C_11 SEQ ID NO:3998, CaF1_WIE_22_F_05 SEQ ID NO:4010, CaF11_WIE_23_C_04 SEQ ID NO:4043, CaF1_WIE_26_A_04 SEQ ID NO:4227, CaF1_WIE_27_A_10 SEQ ID NO:4308, CaF1_WIE_27_C_03 SEQ ID NO:4322, CaF1_WIE_27_H_05 SEQ ID NO:4373, CaF1_WIE_28_A_08 SEQ ID NO:4384, CaF1_WIE_28_D_06 SEQ ID NO:4407, CaF1_WIE_29_E_07 SEQ ID NO:4494, CaF1_WIE_30_C_10 SEQ ID NO:4554, CaF1_WIE_31_G_07 SEQ ID NO:4659, CaF1_WIE_35_F_01 SEQ ID NO:4927, CaF1_WIE_36_A_04 SEQ ID NO:4958, CaF1_WIE_36_A_10 SEQ ID NO:4963, CaF1_WIE_36_F_04 SEQ ID NO:4997, CaF1_WIE_36_G_07 SEQ ID NO:5007, CaF1_WIE_39_A_08 SEQ ID NO:5150, CaF1_WIE_43_D_03 SEQ ID NO:5412, CaF1_WIE_46_A_03 SEQ ID NO:5565, CaF1_WIE_46_E_11 SEQ ID NO:5607, CaF1_WIE_47_B_02 SEQ ID NO:5643, CaF1_WIE_47_E_03 SEQ ID NO:5672, CaF1_WIE_49_E_02 SEQ ID NO:5808, CaF1_WIE_52_B_02 SEQ ID NO:5966, CaF1_WIE_53_E_02 SEQ ID NO:6059 and CaF1_WIE_54_B_05 SEQ ID NO:6093

Genes Involved in Secondary Metabolism

Most secondary metabolites of phenyl propanoid pathway, including lignins, isoflavonoid-phytoalexins and other phenolic compounds are instrumental in plant's ability to enforce successful defenses against invading pathogens. In this study, several genes were identified that are associated with biosynthesis of secondary metabolites. The important enzymes in this category include phenyl ammonia lyase (PAL), chalcone synthase, chalcone isomerase, and chalcone-flavonone isomerase-1 which were found in both compatible and incompatible interactions. These enzymes are known to modulate plant defense response against invading pathogens and insects. Some of the secondary metabolism related genes, for example, squalene epoxidase was found to be specific to susceptible genotype whereas pterocarpan reductase and oxysterol-binding family protein were specific to the resistant one. Other members of this class are caffeic acid O-methyltransferase II, isoflavone 3'-hydroxylase, squalene monooxygenase 2, trans-cinnamate 4-monooxygenase and dihydroflavonol reductase. Earlier studies have shown that transgenic rice plants overexpressing dihydroflavonol reductase can provide tolerance to biotic and abiotic stresses. Caffeic acid O-methyltransferase catalyzes a key step in lignin biosynthesis, thereby giving protection against pathogen attack Still another embodiment of the present invention provides ESTs derived from chickpea, wherein the ESTs are related to secondary metabolism. These ESTs are CaF1_JIE_02_G_09 SEQ ID NO:131, CaF1_JIE_02_H_11 SEQ ID NO:142, CaF1_JIE_03_F_02 SEQ ID NO:184, CaF1_JIE_04_A_02 SEQ ID NO:211, CaF1_JIE_04_D_09 SEQ ID NO:247, CaF1_JIE_07_D_08 SEQ ID NO:472, CaF1_JIE_07_H_08 SEQ ID NO:512, CaF1_JIE_08_A_05 SEQ ID NO:519, CaF1_JIE_08_C_04 SEQ ID NO:538, CaF1_JIE_08_E_03 SEQ ID NO:558, CaF1_JIE_08_H_03 SEQ ID NO:589, CaF1_JIE_09_A_06 SEQ ID NO:603, CaF1_JIE_09_B_01 SEQ ID NO:608, CaF1_JIE_14_D_02 SEQ ID NO:1545, CaF1_JIE_16_E_04 SEQ ID NO:1685, CaF1_JIE_17_A_09 SEQ ID NO:1722, CaF1_JIE_18_H_07 SEQ ID NO:1833, CaF1_JIE_21_C_08 SEQ ID NO:2013, CaF1_JIE_21_E_02 SEQ ID NO:2027, CaF1_JIE_22_D_03 SEQ ID NO:2092, CaF1_JIE_22_G_07 SEQ ID NO:2126, CaF1_JIE_22_H_05 SEQ ID NO:2134, CaF1_JIE_24_C_03 SEQ ID NO:2242, CaF1_JIE_24_E_06 SEQ ID NO:2261, CaF1_JIE_27_13_02 SEQ ID NO:2419, CaF1_JIE_27_C_08 SEQ ID NO:2430, CaF1_JIE_28_C_08 SEQ ID NO:2485, CaF1_JIE_28_D_04 SEQ ID NO:2490, CaF1_JIE_30_C_11 SEQ ID NO:2585, CaF1_JIE_32_B_08 SEQ ID NO:2683, CaF1_JIE_32_G_04 SEQ ID NO:2711, CaF1_JIE_34_A_01 SEQ ID NO:2781, CaF1_JIE_34_C_09 SEQ ID NO:2800, CaF1_JIE_35_A_02 SEQ ID NO:2839, CaF1_JIE_35_D_11 SEQ ID NO:2869, CaF1_JIE_37_E_02 SEQ ID NO:2971, CaF1_JIE_37_E_07 SEQ ID NO:2974, CaF1_JIE_37_F_08 SEQ ID NO:2979, CaF1_JIE_37_G_08 SEQ ID NO:2986, CaF1_JIE_37_H_04 SEQ ID NO:2991, CaF1_JIE_37_H_09 SEQ ID NO:2996, CaF1_JIE_38_C_11 SEQ ID NO:3019, CaF1_JIE_39_B_02 SEQ ID NO:3062, CaF1_JIE_39_B_06 SEQ ID NO:3065, CaF1_JIE_39_C_05 SEQ ID NO:3072, CaF1_JIE_39_E_02 SEQ ID NO:3084, CaF1_JIE_42_B_01 SEQ ID NO:3249, CaF1_JIE_42_G_06 SEQ ID NO:3268, CaF1_JIE_42_G_07 SEQ ID NO:3269, CaF1_JIE_42_G_09 SEQ ID NO:3270, CaF1_WIE_01_D_10 SEQ ID NO:663, CaF1_WIE_01_G_11 SEQ ID NO:690, CaF1_WIE_01_H_05 SEQ ID NO:694, CaF1_WIE_01_H_11 SEQ ID NO:699, CaF1_WIE_02_G_06 SEQ ID NO:749, CaF1_WIE_03_B_01 SEQ ID NO:770, CaF1_WIE_05_A_02 SEQ ID NO:888, CaF1_WIE_05_C_08 SEQ ID NO:910, CaF1_WIE_05_E_08 SEQ ID NO:928, CaF1_WIE_06_C_11 SEQ ID NO:979, CaF1_WIE_06_D_03 SEQ ID NO:981, CaF1_WIE_06_E_01 SEQ ID NO:987, CaF1_WIE_07_G_08 SEQ ID NO:1090, CaF1_WIE_08_C_02 SEQ ID NO:1120, CaF1_WIE_08_C_04 SEQ ID NO:1122, CaF1_WIE_08_D_01 SEQ ID NO:1129, CaF1_WIE_08_G_09 SEQ ID NO:1162, CaF1_WIE_09_B_02 SEQ ID NO:1183, CaF1_WIE_10_B_09 SEQ ID NO:1250, CaF1_WIE_10_E_03 SEQ ID NO:3273, CaF1_WIE_12_A_01 SEQ ID NO:3377, CaF1_WIE_13_F_01 SEQ ID NO:3497, CaF1_WIE_13_G_06 SEQ ID NO:3510, CaF1_WIE_14_F_06 SEQ ID NO:3548, CaF1_WIE_15_E_06 SEQ ID NO:3584, CaF1_WIE_15_E_07 SEQ ID NO:3585, CaF1_WIE_17_C_04 SEQ ID NO:3667, CaF1_WIE_17_C_05 SEQ ID NO:3668, CaF1_WIE_19_D_02 SEQ ID NO:3824, CaF1_WIE_23_E_04 SEQ ID NO:4056, CaF1_WIE_24_A_03 SEQ ID NO:4088, CaF1_WIE_24_C_05 SEQ ID NO:4108, CaF1_WIE_24_C_10 SEQ ID NO:4111, CaF1_WIE_24_G_11 SEQ ID NO:4148, CaF1_WIE_27_B_04 SEQ ID NO:4312, CaF1_WIE_27_C_04 SEQ ID NO:4323, CaF1_WIE_27_D_09 SEQ ID NO:4335, CaF1_WIE_28_D_04 SEQ ID NO:4405, CaF1_WIE_28_F_03 SEQ ID NO:4421, CaF1_WIE_28_G_06 SEQ ID NO:4431, CaF1_WIE_29_A_06 SEQ ID NO:4450, CaF1_WIE_29_B_10 SEQ ID NO:4465, CaF1_WIE_30_B_11 SEQ ID NO:4547, CaF1_WIE_30_E_01 SEQ ID NO:4566, CaF1_WIE_31_E_04 SEQ ID NO:4639, CaF1_WIE_31_F_07 SEQ ID NO:4650, CaF1_WIE_32_A_06 SEQ ID NO:4676, CaF1_WIE_33_A_10 SEQ ID NO:4752, CaF1_WIE_34_F_07 SEQ ID NO:4858, CaF1_WIE_35_E_09 SEQ ID NO:4924, CaF1_WIE_37_A_07 SEQ ID NO:5025, CaF1_WIE_37_E_03 SEQ ID NO:5050, CaF1_WIE_40_A_11 SEQ ID NO:5208, CaF1_WIE_40_F_05 SEQ ID NO:5247, CaF1_WIE_42_H_03 SEQ ID NO:5385, CaF1_WIE_43_D_11 SEQ ID NO:5418, CaF1_WIE_47_A_09 SEQ ID NO:5640, CaF1_WIE_48_B_07 SEQ ID NO:5720, CaF1_WIE_50_A_10 SEQ ID NO:5837, CaF1_WIE_51_D_05 SEQ ID NO:5928, CaF1_WIE_51_E_01 SEQ ID NO:5933, CaF1_WIE_51_G_01 SEQ ID NO:5947, CaF1_WIE_52_D_05 SEQ ID NO:5986, CaF1_WIE_52_E_09 SEQ ID NO:5998, CaF1_WIE_53_B_09 SEQ ID NO:6041, CaF1_WIE_53_C_04 SEQ ID NO:6045, CaF1_WIE_53_C_08 SEQ ID NO:6048 and CaF1_WIE_54_H_05 SEQ ID NO:6149.

Defense and Stress Responsive Genes

Pathogen attack is often accompanied by the accumulation of elevated levels of transcripts of disease related proteins, the PR genes. The ESTs encoding proteins implicated in stress and defense responses account for 3.18% of the total unigene set. Most dominant candidates among the defense responsive genes were disease resistance response protein DRRG49C and PR10. Other genes identified include those encoding chitinase, non-specific lipid transfer proteins, thaumatin and pathogenesis-related protein. The involvement of these proteins in plant defense responses is well known. One of the important observations was that DRRG49C, thaumatin and pathogenesis-related protein were expressed only during incompatible interaction which may lead to increased tolerance to pathogen attack. Also, we found the presence of ESTs encoding proteins like dirigent and harpin-induced 1 in the resistant genotype, implying their role in pathostress response. Dirigent protein has recently been shown to be involved in lignification and hence imparting disease resistance. Many other stress induced proteins, for example, extension, universal stress proteins, aquaporin, annexin, cold acclimation responsive protein BudCAR4 and metallothionien were also identified as more abundant in the resistant genotype implicating their involvement in pathostress response besides their key role in abiotic and other stresses.

Still another embodiment of the present invention provides ESTs derived from chickpea, wherein the ESTs are related to defense mechanism. These ESTs are CaF1_JIE_04_E_08 SEQ ID NO:255, CaF1_JIE_04_H_01 SEQ ID NO:280, CaF1_JIE_07_G_06 SEQ ID NO:499, CaF1_JIE_08_B_06 SEQ ID NO:530, CaF1_JIE_08_E_06 SEQ ID NO:561, CaF1_JIE_10_B_06 SEQ ID NO:1328, CaF1_JIE_11_A_03 SEQ ID NO:1362, CaF1_JIE_11_F_04 SEQ ID NO:1403, CaF1_JIE_13_F_10 SEQ ID NO:1507, CaF1_JIE_13_G_07 SEQ ID NO:1511, CaF1_JIE_13_G_08 SEQ ID NO:1512, CaF1_JIE_14_B_03 SEQ ID NO:1529, CaF1_JIE_14_F_01 SEQ ID NO:1559, CaF1_JIE_15_D_02 SEQ ID NO:1609, CaF1_JIE_20_A_02 SEQ ID NO:1905, CaF1_JIE_21_A_06 SEQ ID NO:1991, CaF1_JIE_21_D_04 SEQ ID NO:2020, CaF1_JIE_22_A_08 SEQ ID NO:2068, CaF1_JIE_22_B_09 SEQ ID NO:2080, CaF1_JIE_22_C_05 SEQ ID NO:2084, CaF1_JIE_24_E_09 SEQ ID NO:2264, CaF1_JIE_25_A_11 SEQ ID NO:2296, CaF1_JIE_25_13_07 SEQ ID NO:2302, CaF1_JIE_25_D_06 SEQ ID NO:2313, CaF1_JIE_25_D_07 SEQ ID NO:2314, CaF1_JIE_27_A_06 SEQ ID NO:2415, CaF1_JIE_27_B_11 SEQ ID NO:2424, CaF1_JIE_27_C_01 SEQ ID NO:2425, CaF1_JIE_35_C_10 SEQ ID NO:2859, CaF1_JIE_38_B_11 SEQ ID NO:3015, CaF1_JIE_42_A_11 SEQ ID NO:3248, CaF1_JIE_42_G_02 SEQ ID NO:3266, CaF1_WIE_01_A_02 SEQ ID NO:631, CaF1_WIE_C_08 SEQ ID NO:652, CaF1_WIE_01_F_11 SEQ ID NO:680, CaF1_WIE_02_B_07 SEQ ID NO:711, CaF1_WIE_02_F_09 SEQ ID NO:746, CaF1_WIE_04_B_01 SEQ ID NO:826, CaF1_WIE_04_B_10 SEQ ID NO:834, CaF1_WIE_04_D_02 SEQ ID NO:844, CaF1_WIE_04_D_08 SEQ ID NO:849, CaF1_WIE_04_H_02 SEQ ID NO:880, CaF1_WIE_05_D_03 SEQ ID NO:914, CaF1_WIE_05_D_09 SEQ ID NO:919, CaF1_WIE_05_E_07 SEQ ID NO:927, CaF1_WIE_05_F_03 SEQ ID NO:933, CaF1_WIE_05_G_08 SEQ ID NO:945, CaF1_WIE_05_G_09 SEQ ID NO:946, CaF1_WIE_05_H_11 SEQ ID NO:956, CaF1_WIE_06_C_03 SEQ ID NO:974, CaF1_WIE_06_C_09 SEQ ID NO:978, CaF1_WIE_06_D_08 SEQ ID NO:984, CaF1_WIE_06_F_02 SEQ ID NO:998, CaF1_WIE_08_D_09 SEQ ID NO:1137, CaF1_WIE_08_G_06 SEQ ID NO:1159, CaF1_WIE_09_D_09 SEQ ID NO:1196, CaF1_WIE_09_F_05 SEQ ID NO:1213, CaF1_WIE_10_A_10 SEQ ID NO:1242, CaF1_WIE_10_B_04 SEQ ID NO:1246, CaF1_WIE_10_E_07 SEQ ID NO:3277, CaF1_WIE_10_F_09 SEQ ID NO:3287, CaF1_WIE_10_G_07 SEQ ID NO:3294, CaF1_WIE_11_B_04 SEQ ID NO:3319, CaF1_WIE_11_D_02 SEQ ID NO:3336, CaF1_WIE_11_D_03 SEQ ID NO:3337, CaF1_WIE_11_G_08 SEQ ID NO:3365, CaF1_WIE_13_E_03 SEQ ID NO:3489, CaF1_WIE_14_D_07 SEQ ID NO:3538, CaF1_WIE_14_D_08 SEQ ID NO:3539, CaF1_WIE_14_H_01 SEQ ID NO:3558, CaF1_WIE_15_E_05 SEQ ID NO:3583, CaF1_WIE_17_E_10 SEQ ID NO:3693, CaF1_WIE_17_G_01 SEQ ID NO:3705, CaF1_WIE_18_A_03 SEQ ID NO:3724, CaF1_WIE_18_C_11 SEQ ID NO:3750, CaF1_WIE_18_E_04 SEQ ID NO:3762, CaF1_WIE_18_G_11 SEQ ID NO:3788, CaF1_WIE_19_A_09 SEQ ID NO:3803, CaF1_WIE_19_C_05 SEQ ID NO:3817, CaF1_WIE_19_C_06 SEQ ID NO:3818, CaF1_WIE_19_C_07 SEQ ID NO:3819, CaF1_WIE_19_F_06 SEQ ID NO:3841, CaF1_WIE_21_G_10 SEQ ID NO:3968, CaF1_WIE_22_B_02 SEQ ID NO:3985, CaF1_WIE_22_B_06 SEQ ID NO:3986, CaF1_WIE_22_C_01 SEQ ID NO:3991, CaF1_WIE_22_C_05 SEQ ID NO:3995, CaF1_WIE_22_E_10 SEQ ID NO:4007, CaF1_WIE_23_C_05 SEQ ID NO:4044, CaF1_WIE_23_E_02 SEQ ID NO:4054, CaF1_WIE_23_E_10 SEQ ID NO:4060, CaF1_WIE_24_11_03 SEQ ID NO:4098, CaF1_WIE_24_B_11 SEQ ID NO:4104, CaF1_WIE_24_C_01 SEQ ID NO:4105, CaF1_WIE_24_E_03 SEQ ID NO:4122, CaF1_WIE_25_B_09 SEQ ID NO:4175, CaF1_WIE_26_D_07 SEQ ID NO:4257, CaF1_WIE_26_D_08 SEQ ID NO:4258, CaF1_WIE_27_A_08 SEQ ID NO:4306, CaF1_WIE_27_A_09 SEQ ID NO:4307, CaF1_WIE_27_B_02 SEQ ID NO:4310, CaF1_WIE_27_D_11 SEQ ID NO:4337, CaF1_WIE_27_F_03 SEQ ID NO:4350, CaF1_WIE_27_H_08 SEQ ID NO:4376, CaF1_WIE_28_D_08 SEQ ID NO:4409, CaF1_WIE_28_E_05 SEQ ID NO:4415, CaF1_WIE_28_G_02 SEQ ID NO:4427, CaF1_WIE_29_B_01 SEQ ID NO:4456, CaF1_WIE_29_C_06 SEQ ID NO:4472, CaF1_WIE_29_D_02 SEQ ID NO:4479, CaF1_WIE_29_E_11 SEQ ID NO:4498, CaF1_WIE_30_A_09 SEQ ID NO:4537, CaF1_WIE_30_B_06 SEQ ID NO:4542, CaF1_WIE_30_C_01 SEQ ID NO:4548, CaF1_WIE_30_D_01 SEQ ID NO:4556, CaF1_WIE_30_F_01 SEQ ID NO:4575, CaF1_WIE_30_H_10 SEQ ID NO:4600, CaF1_WIE_31_A_10 SEQ ID NO:4609, CaF1_WIE_31_B_08 SEQ ID NO:4616, CaF1_WIE_31_D_09 SEQ ID NO:4633, CaF1_WIE_32_A_05 SEQ ID NO:4675, CaF1_WIE_32_C_11 SEQ ID NO:4700, CaF1_WIE_32_D_09 SEQ ID NO:4705, CaF1_WIE_32_F_06 SEQ ID NO:4718, CaF1_WIE_32_G_11 SEQ ID NO:4734, CaF1_WIE_33_F_04 SEQ ID NO:4788, CaF1_WIE_33_F_11 SEQ ID NO:4794, CaF1_WIE_33_G_05 SEQ ID NO:4798, CaF1_WIE_34_H_10 SEQ ID NO:4875, CaF1_WIE_36_A_11 SEQ ID NO:4964, CaF1_WIE_36_B_08 SEQ ID NO:4968, CaF1_WIE_36_C_10 SEQ ID NO:4977, CaF1_WIE_36_D_04 SEQ ID NO:4981, CaF1_WIE_37_E_02 SEQ ID NO:5049, CaF1_WIE_38_A_06 SEQ ID NO:5088, CaF1_WIE_38_A_09 SEQ ID NO:5091, CaF1_WIE_38_F_05 SEQ ID NO:5124, CaF1_WIE_39_A_05 SEQ ID NO:5147, CaF1_WIE_40_B_06 SEQ ID NO:5213, CaF1_WIE_40_E_11 SEQ ID NO:5243, CaF1_WIE_41_E_01 SEQ ID NO:5306, CaF1_WIE_42_F_06 SEQ ID NO:5375, CaF1_WIE_42_F_07 SEQ ID NO:5376, CaF1_WIE_43_A_10 SEQ ID NO:5395, CaF1_WIE_43_B_08 SEQ ID NO:5403, CaF1_WIE_43_B_11 SEQ ID NO:5405, CaF1_WIE_43_F_01 SEQ ID NO:5425, CaF1_WIE_43_G_11 SEQ ID NO:5438, CaF1_WIE_44_B_11 SEQ ID NO:5453, CaF1_WIE_45_B_04 SEQ ID NO:5514, CaF1_WIE_45_C_04 SEQ ID NO:5521, CaF1_WIE_45_D_07 SEQ ID NO:5527, CaF1_WIE_46_B_11 SEQ ID NO:5580, CaF1_WIE_46_E_06 SEQ ID NO:5602, CaF1_WIE_47_A_04 SEQ ID NO:5635, CaF1_WIE_47_C_07 SEQ ID NO:5655, CaF1_WIE_48_F_10 SEQ ID NO:5757, CaF1_WIE_48_F_11 SEQ ID NO:5758, CaF1_WIE_48_H_03 SEQ ID NO:5768, CaF1_WIE_48_H_09 SEQ ID NO:5772, CaF1_WIE_49_A_04 SEQ ID NO:5777, CaF1_WIE_49_A_05 SEQ ID NO:5778, CaF1_WIE_49_C_01 SEQ ID NO:5793, CaF1_WIE_49_H_09 SEQ ID NO:5832, CaF1_WIE_50_B_02 SEQ ID NO:5839, CaF1_WIE_50_B_06 SEQ ID NO:5843, CaF1_WIE_51_C_01 SEQ ID NO:5914, CaF1_WIE_51_C_08 SEQ ID NO:5921, CaF1_WIE_51_E_05 SEQ ID NO:5935, CaF1_WIE_52_B_08 SEQ ID NO:5972, CaF1_WIE_52_D_09 SEQ ID NO:5989, CaF1_WIE_53_B_05 SEQ ID NO:6038, CaF1_WIE_53_B_08 SEQ ID NO:6040, CaF1_WIE_53_D_02 SEQ ID NO:6051, CaF1_WIE_53_D_09 SEQ ID NO:6056, CaF1_WIE_54_F_09 SEQ ID NO:6136, CaF1_WIE_55_G_04 SEQ ID NO:6202, CaF1_WIE_56_A_08 SEQ ID NO:6224, CaF1_WIE_56_G_10 SEQ ID NO:6263

Still another embodiment of the present invention provides ESTs derived from chickpea, wherein the ESTs are related to stress. These are CaF1_JIE_01_D_10 SEQ ID NO:40, CaF1_JIE_02_C_06 SEQ ID NO:93, CaF1_JIE_02_F_01 SEQ ID NO:115, CaF1_JIE_02_F_06 SEQ ID NO:120, CaF1_JIE_02_G_06 SEQ ID NO:128, CaF1_JIE_07_A_08 SEQ ID NO:441, CaF1_JIE_07_C_10 SEQ ID NO:463, CaF1_JIE_07_H_06 SEQ ID NO:510, CaF1_JIE_08_A_01 SEQ ID NO:516, CaF1_JIE_08_G_05 SEQ ID NO:580, CaF1_JIE_08_H_11 SEQ ID NO:597, CaF1_JIE_14_F_05 SEQ ID NO:1563, CaF1_JIE_15_B_01 SEQ ID NO:1591, CaF1_JIE_18_D_08 SEQ ID NO:1798, CaF1_JIE_25_B_02 SEQ ID NO:2298, CaF1_JIE_25_G_06 SEQ ID NO:2336, CaF1_JIE_27_B_08 SEQ ID NO:2422, CaF1_JIE_29_G_09 SEQ ID NO:2559, CaF1_JIE_29_G_10 SEQ ID NO:2560, CaF1_JIE_31_A_03 SEQ ID NO:2617, CaF1_JIE_31_F_10 SEQ ID NO:2656, CaF1_JIE_31_G_07 SEQ ID NO:2663, CaF1_JIE_31_H_10 SEQ ID NO:2675, CaF1_JIE_32_C_02 SEQ ID NO:2686, CaF1_JIE_32_C_11 SEQ ID NO:2690, CaF1_JIE_32_F_05 SEQ ID NO:2706, CaF1_JIE_36_F_10 SEQ ID NO:2934, CaF1_JIE_36_G_10 SEQ ID NO:2938, CaF1_JIE_39_B_10 SEQ ID NO:3066, CaF1_JIE_39_D_10 SEQ ID NO:3082, CaF1_JIE_39_F_11 SEQ ID NO:3096, CaF1_JIE_41_B_05 SEQ ID NO:3189, CaF1_JIE_41_D_05 SEQ ID NO:3205, CaF1_JIE_41_F_06 SEQ ID NO:3223, CaF1_WIE_01_E_01 SEQ ID NO:665, CaF1_WIE_01_E_03 SEQ ID NO:666, CaF1_WIE_02_A_11 SEQ ID NO:706, CaF1_WIE_02_D_10 SEQ ID NO:727, CaF1_WIE_02_F_08 SEQ ID NO:745, CaF1_WIE_02_H_03 SEQ ID NO:756, CaF1_WIE_02_H_05 SEQ ID NO:757, CaF1_WIE_03_A_01 SEQ ID NO:763, CaF1_WIE_03_C_11 SEQ ID NO:782, CaF1_WIE_04_A_05 SEQ ID NO:821, CaF1_WIE_04_A_11 SEQ ID NO:825, CaF1_WIE_04_E_04 SEQ ID NO:855, CaF1_WIE_04_E_08 SEQ ID NO:859, CaF1_WIE_05_D_08 SEQ ID NO:918, CaF1_WIE_06_A_08 SEQ ID NO:963, CaF1_WIE_06_E_09 SEQ ID NO:994, CaF1_WIE_06_F_04 SEQ ID NO:999, CaF1_WIE_07_A_09 SEQ ID NO:1032, CaF1_WIE_07_C_10 SEQ ID NO:1052, CaF1_WIE_07_H_11 SEQ ID NO:1102, CaF1_WIE_08_B_08 SEQ ID NO:1115, CaF1_WIE_09_A_09 SEQ ID NO:1180, CaF1_WIE_09_C_06 SEQ ID NO:1188, CaF1_WIE_09_E_05 SEQ ID NO:1202, CaF1_WIE_10_C_09 SEQ ID NO:1259, CaF1_WIE_11_B_06 SEQ ID NO:3321, CaF1_WIE_11_H_07 SEQ ID NO:3373, CaF1_WIE_12_B_05 SEQ ID NO:3388, CaF1_WIE_14_C_08 SEQ ID NO:3533, CaF1_WIE_15_D_06 SEQ ID NO:3581, CaF1_WIE_16_E_09 SEQ ID NO:3624, CaF1_WIE_16_F_10 SEQ ID NO:3628, CaF1_WIE_17_B_06 SEQ ID NO:3660, CaF1_WIE_17_C_10 SEQ ID NO:3673, CaF1_WIE_19_A_03 SEQ ID NO:3798, CaF1_WIE_19_D_04 SEQ ID NO:3826, CaF1_WIE_19_F_08 SEQ ID NO:3843, CaF1_WIE_19_G_10 SEQ ID NO:3851, CaF1_WIE_20_D_11 SEQ ID NO:3883, CaF1_WIE_20_E_11 SEQ ID NO:3892, CaF1_WIE_20_G_07 SEQ ID NO:3904, CaF1_WIE_20_G_09 SEQ ID NO:3905, CaF1_WIE_21_C_04 SEQ ID NO:3934, CaF1_WIE_22_A_01 SEQ ID NO:3978, CaF1_WIE_22_B_07 SEQ ID NO:3987, CaF1_WIE_22_C_08 SEQ ID NO:3997, CaF1_WIE_22_H_06 SEQ ID NO:4024, CaF1_WIE_23_A_02 SEQ ID NO:4029, CaF1_WIE_25_B_02 SEQ ID NO:4169, CaF1_WIE_25_H_09 SEQ ID NO:4221, CaF1_WIE_26_E_09 SEQ ID NO:4270, CaF1_WIE_27_A_07 SEQ ID NO:4305, CaF1_WIE_27_B_07 SEQ ID NO:4315, CaF1_WIE_27_H_06 SEQ ID NO:4374, CaF1_WIE_28_B_09 SEQ ID NO:4392, CaF1_WIE_28_E_01 SEQ ID NO:4412, CaF1_WIE_28_H_09 SEQ ID NO:4443, CaF1_WIE_

29_H_05 SEQ ID NO:4524, CaF1_WIE_30_D_04 SEQ ID NO:4559, CaF1_WIE_31_F_02 SEQ ID NO:4646, CaF1_WIE_31_G_06 SEQ ID NO:4658, CaF1_WIE_33_B_05 SEQ ID NO:4756, CaF1_WIE_34_E_09 SEQ ID NO:4850, CaF1_WIE_35_B_08 SEQ ID NO:4894, CaF1_WIE_35_B_11 SEQ ID NO:4896, CaF1_WIE_35_F_02 SEQ ID NO:4928, CaF1_WIE_36_H_06 SEQ ID NO:5016, CaF1_WIE_37_D_07 SEQ ID NO:5047, CaF1_WIE_37_G_08 SEQ ID NO:5070, CaF1_WIE_37_H_09 SEQ ID NO:5081, CaF1_WIE_40_A_03 SEQ ID NO:5200, CaF1_WIE_40_A_06 SEQ ID NO:5203, CaF1_WIE_40_B_09 SEQ ID NO:5215, CaF1_WIE_40_E_09 SEQ ID NO:5241, CaF1_WIE_40_H_06 SEQ ID NO:5267, CaF1_WIE_41_H_03 SEQ ID NO:5332, CaF1_WIE_42_D_01 SEQ ID NO:5361, CaF1_WIE_42_D_02 SEQ ID NO:5362, CaF1_WIE_42_G_01 SEQ ID NO:5379, CaF1_WIE_45_F_02 SEQ ID NO:5538, CaF1_WIE_46_B_05 SEQ ID NO:5575, CaF1_WIE_46_B_10 SEQ ID NO:5579, CaF1_WIE_46_C_06 SEQ ID NO:5585, CaF1_WIE_47_C_08 SEQ ID NO:5656, CaF1_WIE_47_D_03 SEQ ID NO:5662, CaF1_WIE_47_H_04 SEQ ID NO:5704, CaF1_WIE_48_B_05 SEQ ID NO:5719, CaF1_WIE_48_F_09 SEQ ID NO:5756, CaF1_WIE_50_B_09 SEQ ID NO:5846, CaF1_WIE_50_D_09 SEQ ID NO:5863, CaF1_WIE_51_D_06 SEQ ID NO:5929, CaF1_WIE_51_D_10 SEQ ID NO:5931, CaF1_WIE_52_B_07 SEQ ID NO:5971, CaF1_WIE_52_D_11 SEQ ID NO:5991, CaF1_WIE_52_H_08 SEQ ID NO:6024, CaF1_WIE_54_A_08 SEQ ID NO:6087, CaF1_WIE_54_C_01 SEQ ID NO:6099, CaF1_WIE_54_H_08 SEQ ID NO:6151, CaF1_WIE_54_H_11 SEQ ID NO:6153, CaF1_WIE_55_B_05 SEQ ID NO:6161, CaF1_WIE_55_B_06 SEQ ID NO:6162 and CaF1_WIE_56_D_03 SEQ ID NO:6239.

In another embodiment the present invention provides ESTs derived from chickpea, wherein the ESTs are related to Photosynthesis These ESTs are CaF1_JIE_01_C_10 SEQ ID NO:30, CaF1_JIE_02_B_10 SEQ ID NO:86, CaF1_JIE_02_D_10 SEQ ID NO:106, CaF1_JIE_06_B_08_SEQ ID NO:385, CaF1_JIE_07_D_10 SEQ ID NO:474, CaF1_JIE_09_C_05 SEQ ID NO:622, CaF1_JIE_09_F_03 SEQ ID NO:1294, CaF1_JIE_10_H_02 SEQ ID NO:1353, CaF1_JIE_14_A_09 SEQ ID NO:1526, CaF1_JIE_14_H_04 SEQ ID NO:1576, CaF1_JIE_15_H_10 SEQ ID NO:1648, CaF1_JIE_18_F_07 SEQ ID NO:1816, CaF1_JIE_20_D_11 SEQ ID NO:1944, CaF1_JIE_20_E_06 SEQ ID NO:1950, CaF1_JIE_22_A_01 SEQ ID NO:2061, CaF1_JIE_22_B_01 SEQ ID NO:2072, CaF1_JIE_22_G_05 SEQ ID NO:2124, CaF1_JIE_23_C_02 SEQ ID NO:2163, CaF1_JIE_23_C_04 SEQ ID NO:2165, CaF1_JIE_23_C_05 SEQ ID NO:2166, CaF1_JIE_26_C_03 SEQ ID NO:2365, CaF1_JIE_29_E_03 SEQ ID NO:2547, CaF1_JIE_33_D_02 SEQ ID NO:2750, CaF1_JIE_34_G_06 SEQ ID NO:2824, CaF1_JIE_34_G_07 SEQ ID NO:2825, CaF1_JIE_34_G_08 SEQ ID NO:2826, CaF1_JIE_34_H_09 SEQ ID NO:2835, CaF1_JIE_34_H_10 SEQ ID NO:2836, CaF1_JIE_35_B_11 SEQ ID NO:2853, CaF1_JIE_36_B_01 SEQ ID NO:2898, CaF1_JIE_36_E_11 SEQ ID NO:2928, CaF1_JIE_37_D_09 SEQ ID NO:2970, CaF1_JIE_37_G_10 SEQ ID NO:2988, CaF1_JIE_39_A_03 SEQ ID NO:3057, CaF1_JIE_40_G_09 SEQ ID NO:3168, CaF1_WIE_01_H_03 SEQ ID NO:692, CaF1_WIE_05_B_07 SEQ ID NO:900, CaF1_WIE_05_F_02 SEQ ID NO:932, CaF1_WIE_22_H_02 SEQ ID NO:4020, CaF1_WIE_25_B_08 SEQ ID NO:4174, CaF1_WIE_26_B_08 SEQ ID NO:4238, CaF1_WIE_32_E_08 SEQ ID NO:4713, CaF1_WIE_33_G_08 SEQ ID NO:4801, CaF1_WIE_37_A_01 SEQ ID NO:5022, CaF1_WIE_41_E_02 SEQ ID NO:5307, CaF1_WIE_44_B_03 SEQ ID NO:5448, CaF1_WIE_44_C_03 SEQ ID NO:5456, CaF1_WIE_47_B_03 SEQ ID NO:5644, CaF1_WIE_47_G_07 SEQ ID NO:5696, CaF1_WIE_47_H_05 SEQ ID NO:5705, CaF1_WIE_49_A_09 SEQ ID NO:5781, CaF1_WIE_49_E_07 SEQ ID NO:5810, CaF1_WIE_51_D_11 SEQ ID NO:5932, CaF1_WIE_51_F_02 SEQ ID NO:5942, CaF1_WIE_52_A_02 SEQ ID NO:5957, CaF1_WIE_52_H_11 SEQ ID NO:6026, CaF1_WIE_53_A_08 SEQ ID NO:6032 and CaF1_WIE_54_B_02 SEQ ID NO:6090.

Comparison with Other Legume Genome and EST Databases

To investigate how many of the chickpea ESTs from this study are highly orthologous to other legume ESTs, we performed a comparative analysis of our CaEST dataset to publicly available dataset comprising ESTs from *Arachis hypogea, Cajanus cajan, Pisum sativum, Robinia pseudoacacia, Lotus japonicus, Medicago trunculata, Glycine max* and *Phaseolus vulgaris*. Except *Phaseolus* and *Robinia*, these databases were inclusive of root ESTs. The highest number of common orthologous ESTs was found to be present in *Pisum sativum*, although, *Cajanus cajan* and *Arachis hypogea* also showed higher similarity with CaUnigenes. The percentage of chickpea ESTs that matched to *Pisum sativum* was 88.8% and 79.43% at DNA sequence identity of ≥80% and 90%, respectively. A total of 87.6% and 83% Cajanus cajan ESTs and 85.89% and 55.54% of *Arachis* ESTS were common with CaUnigenes. Chickpea and *Pisum* show close phylogenetic affliations, both being representatives of galegoid, a group of cool season legumes and is reflected in their sequence similarities. However, high sequence similarity with *Arachis* and *Cajanus* came as a surprise since these legumes are phylogenetically distant relatives of *Cicer* and belong to tropical season legumes (phaseoloid). The comparative analysis of chickpea ESTs with that of *Glycine max* showed homology of 80.32% and 31.54%. Interestingly, *Medicago* and *Lotus* showed more divergent trend with only 58.02% and 30.50% and 43.31% and 14.25% ESTs respectively, having counterpart in CaUnigene set. A recent phylogenetic study based on penalized likelihood analysis indicated that *Medicago, Lotus* and *Cicer* are closer and fall in the same galegoid clade, however, the divergence/difference in the pattern of ESTs may be attributed to the fact that gene expression is shaped by cellular environment besides ecological niche of the corresponding organism. Chickpea ESTs showed lesser homology with *Robinia pseudoacacia* and was about 12% and 3.92% at DNA sequence identity of 80% and 90%, respectively. This can be due to the fact that *Robinia* is a perennial tree while chickpea is an annual herb. Detailed comparative analysis of ESTs is shown in Table 3. Thus the current study documents substantial conservation as well as genome divergence amongst legume crops and in future can facilitate cross species analysis of gene function.

Identification of Chickpea Specific Transcripts and Enrichment of CaEST

In an attempt to identify the genotype-specific transcript signatures in chickpea, we performed a blast analysis of CaUnigene. Of the total 2013 CaUnigenes, about 18.22% sequences that belong to NSH group represented potential chickpea specific sequences. To verify whether these sequences were indeed chickpea specific, TBLASTX was used for comparing them to the EST_others database. Nearly 64% of the NSH class of CaEST dataset did not show any significant match thereby confirming that these ESTs represent unique chickpea sequences. Thus this dataset represents 234 novel chickpea specific ESTs, which were never reported earlier. Further, we compared our CaUnigenes with the earlier reported ESTs of chickpea. TBLASTX with e-value cutoff of $10^{-10}$ showed that 532 unigenes from the CaUnigene set of 2013 had a significant match, while the remaining 1483 did not have any counterpart. Thus, 73.67% of our CaUnigenes represent new chickpea genes yet unidentified. Full length sequencing of these unigenes and their expression analyses may provide further insight into the species-specific functions of these genes.

Figure 1:
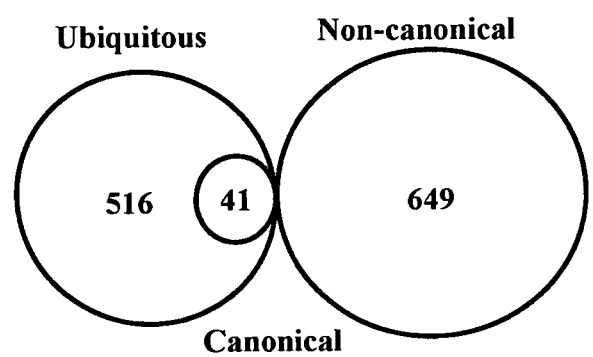
FIG. 1 shows comparative analysis of chickpea stress responsive genes with earlier known stress related genes. Venn represents the overlap between ubiquitous, canonical and non canonical genes and the numbers signify unique and common stress responsive genes.

Comparative Stress Responsive Transcriptome Reveals Canonical and Non-Canonical Genes Although a number of studies have catalogued stress-responsive genes against different environmental conditions into various functional classes but comparative genomics of stress-responsive transcriptome is still lacking. To investigate the comparative biology of stress-responsive transcriptome at organismal level with the currently available data, we compared the CaUnigenes with previously reported stress-responsive genes from other organisms. We classified genes known to be involved in multi-stress responses as ubiquitous, while those found to be specific to *Fusarium* infection were categorized as canonical. All other genes, which have never been implicated in any stress, were designated as noncanonical (FIG. 1). We found that around 516 genes are ubiquitous, suggesting broad similarities in stress responses across most of the organisms and confirming cross communicating pathways playing role in different kinds of stresses. However, only 41 genes were found to be canonical all of which showed an overlap with ubiquitous class. A significantly large number of genes (649) were found to be noncanonical. This difference in the pattern of immune-responsive root transcriptome may be attributed to the fact that the gene expression in an organism is shaped by the cellular environment and the epigenetic factors. Metabolism was one of the most abundant functional class in all the three groups, suggesting that any stress response results in the alteration of the metabolic pathways of an organism. A few of the metabolic enzymes found to be expressed in response to multiple stresses represented in the ubiquitous category included S-adenosylmethionine decarboxylase, glyceraldehyde 3-phosphate dehydrogenase, methionine sulfoxide reductase, and copper amine oxidase. Cell signaling related genes also formed an important class that included leucine-rich repeat receptor-like kinase and multiple bridging factor among others. As expected, many canonical genes belonged to functional class of cellular redox, defense and signaling included Cationic peroxidase 2, chitinase and 14-3-3 protein. Our data on immune responsive transcriptome and comparative analysis thereof provide evidence for molecular diversity vs commanality in gene expression profile at organismal level. The comparative analysis revealed few canonical genes, several ubiquitous genes across different stresses while most of the genes were found to be non-cannonical. An interesting observation was that apart from metabolism, most of the noncanonical genes belonged to the functional classes of translation, posttranslational modifications, transcription, and signaling suggesting the occurrence of new, yet undiscovered immune response pathways. This study thus provides a comprehensive catalogue of non-canonical immune responsive genes or might suggest their species specificity with new insight into their identity and function.

Identification of Gene Families

To assign CaUnigenes from this study to putative gene families, we used single linkage clustering. The individual contigs and singletons were combined into a single dataset which was then compared to itself using TBLASTX with an e-value cutoff of 1E-15. Sequences with overlapping BLAST reports were assigned to a putative gene family. Altogether, we identified 209 gene families ranging in size from 2 to 29 members. This analysis gives insights into following three areas: firstly, it identifies the genes that are likely to cross hybridize during the microarray hybridizations. Secondly, it helps in assigning possible function to genes that had no significant homology to known proteins or belonged to class of UF but clustered with proteins of known function. For example, gene family 23 had two members of which one showed homology to CAP protein while the other showed homology to hypothetical protein. Similarly, one of the members of gene family 32 showed homology to cinnamoyl-CoA reductase, while the other two belonged to NSH class. Also, one member of gene family 124 showed homology with phosphoesterase but the other did not have any significant match. Therefore, on the basis of the family to which such genes either of NSH or UF belong, possible function can be assigned to them and further verified by comparing sequence alignment of these sequences with representative members of the known gene family. Thirdly, the identification of gene families provides a base for uncovering and understanding the biological rationale of functional novelty and partitioning following gene duplications. Towards this, it was interesting to note that in several cases the distribution of different members of the same gene family varied between the genotypes. For example, histone deacetylase HDT1 (contig212) was found to be specific to susceptible genotype while the other member of the same gene family represented by contig713 was present only in the resistant genotype. This was also the case with methionine sulfoxide reductase A, where contig152 and contig555 were specific to susceptible and resistant genotypes respectively. Putative esterase family protein (CaF1_JIE_28_D_10, CaF1_WIE_32_H_04) and putative desaturase (contig454, CaF1_JIE_22_A_09) also showed the same trend. This opens up a new area for finding out whether presence of different gene family members leads to genotype specific response to a particular kind of stress.

Analysis of Genotype-Specific SNPs of Chickpea

SNPs between genotypes/haplotypes once discovered are extensively used for many applications for instance generation of very dense genetic maps, to construct the specific genotypes required for quantitative genetic studies, to enhance understanding of genome organization and function and address fundamental questions relating to evolution. SNPs can also be used for genome-wide linkage disequilibrium and association studies that assign genes to specific functions or traits. Furthermore, transcript-associated SNPs can be used to develop allele-specific assays for the examination of cis regulatory variation within a species. In the present study, SNPs were identified between JG-62, a susceptible and WR-315, a resistant genotype of chickpea to vascular wilt. A total of 279 contigs (28.67% of the total) contained at least one sequence from both the genotypes and were mined for potential SNPs. We identified 262 SNPs which were further classified into high and low quality SNPs depending upon the number of sequences from each genotype showing the same base change. High-quality SNPs were confirmed by two or more sequences from each genotype showing the same base change, while low-quality SNPs were confirmed by one sequence from one genotype and at least two from the other. Thus, we identified 136 high-quality and 126 low-quality SNPs. In the present analysis only base pair mutations were taken into consideration and among these transitions (73.3%) were more common than transversions (26.7%). Within the transitions, occurrence of both adenine to guanine and cytosine to thymidine base changes were found to be almost equal. The maximum numbers of SNPs were present in contigs that comprised of highly abundant ESTs, for example, contig 722 represents the most abundant contig and maximum numbers of SNPs were present in this contig. Similarly, contig 680 and 575 also had high percentage of SNPs and were also very abundant as far as total number of ESTs in these contigs is concerned.

Figure 2:
FIG. 2 shows heat map and functional categories of up-regulated genes during Ca-*Fusarium* (A) compatible and (B) incompatible interactions. Tree view represents the kinetic expression patterns of genes displaying significant regulation response to *Fusarium* infection at different post-pathogen inoculation time points.
Figure 3:
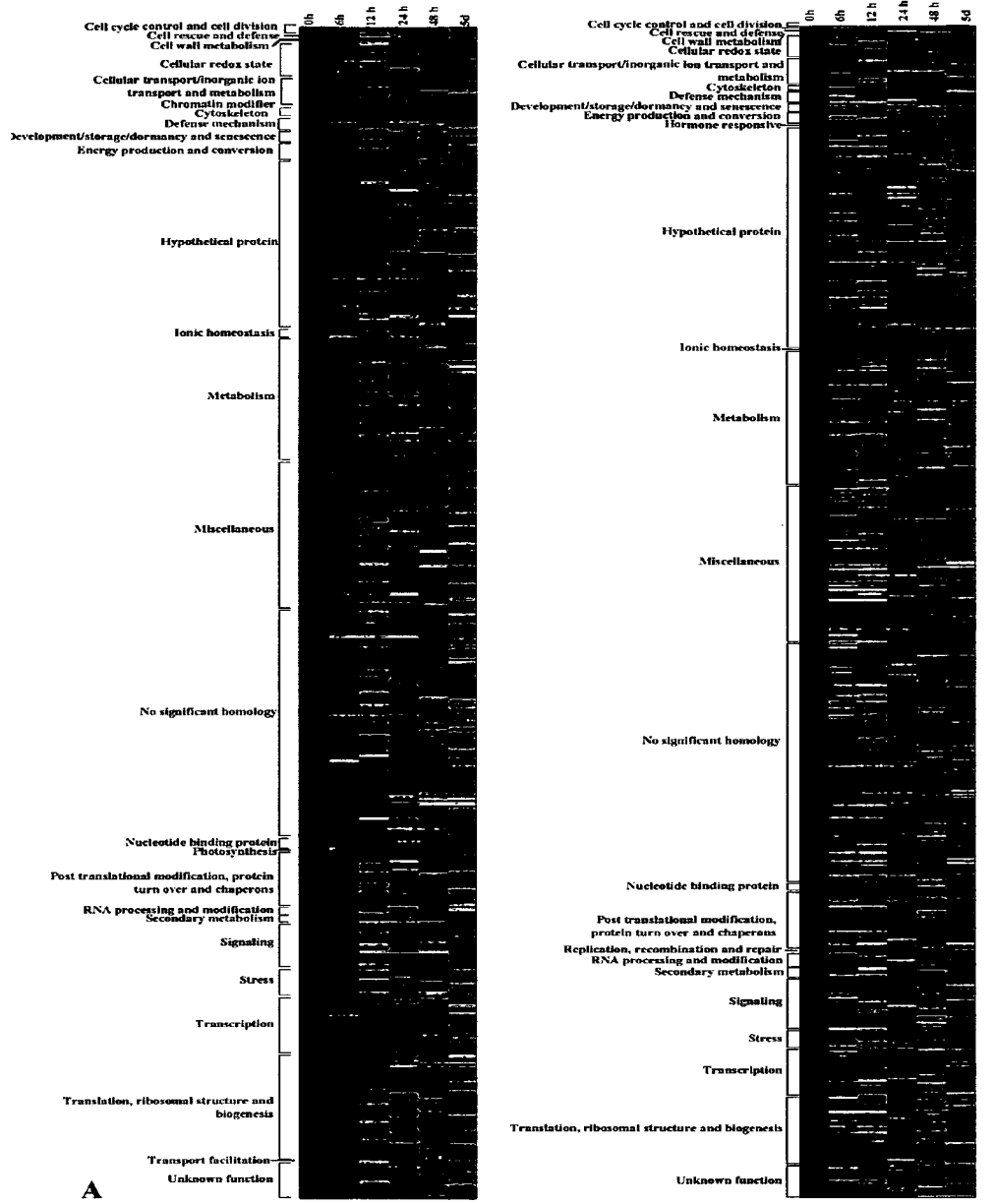
FIG. 3 shows heat map and functional categories of down-regulated genes during Ca-*Fusarium* (A) compatible and (B) incompatible interactions. Tree view represents the kinetic expression patterns of genes displaying significant regulation response to *Fusarium* infection at different post-pathogen inoculation time points.

Immune Responsive Gene Networks in Root Transcriptome of Chickpea by Microarray Analysis To study the transcriptional remodeling in immune response during vascular wilt, we have developed cDNA microarray using CaEST clones of the subtracted cDNA libraries from susceptible and resistant genotypes. Root tissue sample from WR-315 (resistant genotype) and JG62 (susceptible) harvested at five time points post *Fusarium* infection was used to evaluate the expression profile during early phase of incompatible interaction. We used indirect labeling of cDNAs following TSA protocol that incorporates flourscein and biotin labeled dUTP into the nascent cDNA from the target RNA instead of Cy3 and Cy5 modified nucleotides since it is known to negate any dye bias during the microarray experiment. The transcript level for each cDNA was calculated as the average intensity of four data points from duplicate spots of two replicate slides. We used a fold cut off of 2.5 and Students t-test with P≤0.05 ranking with false discovery rate (FDR) multiple testing corrections to identify differentially expressed genes. A total of 1276 differentially expressed unigenes were found to be associated with the early signaling pathway, of which 459 were induced and 565 repressed during compatible interaction while 375 were induced and 464 repressed during incompatible interaction. Further, to identify co-expression kinetics amongst the differentially expressed genes, we clustered the transcriptome data set that grouped the genes in four clusters based on their positive and negative fold change during compatible and incompatible interractions. Cluster 1 represents upregulated genes (FIG. 2A-B) while Cluster 2 comprised of genes repressed (FIG. 3A-B) at various time points post *Fusarium* infection in both compatible and incompatible interactions, respectively. In total 22 functional classes are represented in these two clusters but differed in the type of the representative genes and their relative abundance.

Amongst the total differential genes 413 fell exclusively under compatible while 221 were present solely under the incompatible interaction and 642 were differential to both (FIG. 4A). In case of the induced gene profiles 168 belonged exclusively to the compatible interaction and 84 to the incompatible interaction while 291 were upregulated and represented in both (FIG. 4B). The downregulated or repressed expression patterns had 295 mapped exclusively under compatible interaction and 194 exclusively under incompatible interaction whereas 270 genes showed downregulation in both (FIG. 4C). Moreover, the transcriptional response to immune sensitivity of genes involved in major biological processes and molecular functions showed different dynamics within repressed vs. induced gene clusters. The repressed gene clusters are enriched for genes affecting translation, ribosome structure and biogenesis and protein fate, while the induced cluster is dominated by genes encoding hypothetical proteins, metabolism and miscellaneous groups. Genes involved in metabolism GO category are over-represented in all the clusters but the magnitude of over-representation is higher for cluster 1 than cluster 2. UF, NSH and Miscellaneous categories notably formed a major group of overrepresented genes.

Genes involved in translation, ribosome structure and biogenesis form the largest functional category in cluster 1 for both compatible and incompatible interactions that includes genes for ribosomal proteins, translation initiation and elongation factors. Several genes encoding proteins involved in post translational modifications and protein turnover, for example, protein disufide isomerase-like protein and ubiquitin were also grouped. Many of these genes have previously been implicated in specific stresses in different organisms (Gray 2002). In the repressed set of genes other major functional classes included metabolism, hypothetical proteins, cellular redox state and transcription. These include genes encoding cytochrome P450, thioredoxin, superoxide dismutase and glutathione-5-transferase that are known to play critical role in plant stress. Many carbohydrate metabolism genes like GAPDH, triosephosphate isomerase and malate dehydrogenase precursor were downregulated. Earlier reports showed altered expression of GAPDH during plant stress, however the specific function of this enzyme during stress is not known. Moreover GAPDH has also been known to act as an essential component of transcriptional activator complex regulating histone expression. We also observed defense related genes like chitinase 1 and PR10, and secondary metabolism genes like chalcone synthase and isoflavone 3'-hydroxylase to be repressed during *Fusarium* infection. These genes are known to be associated with pathogen stress.

In contrary, genes encoding hypothetical proteins, metabolism and miscellaneous groups form the dominant functional class in repressed clusters. The induced set of metabolic genes include some carbohydrate metabolism genes like FBF, aldolase and pfkB-type carbohydrate kinase family protein of carbohydrate metabolism and oleate desaturase involved in lipid metabolism. The role of these enzymes in plant immunity has not yet been defined and hence will be of great interest in future. Post-translational modification and protein turnover related genes like cystatin, Sec61 beta and ubiquitin extension protein were also induced consistent with the notion that damaged or partially denatured proteins need to be degraded to prevent the accumulation of protein aggregates. Many such genes are involved in regulating protein metabolism in response to stress. Other cell stress induced genes include classical phenylpropanoid pathway genes like chalcone reductase and chalcone—flavonone isomerase 1. Role played by these genes during cell defense is a well known phenomenon. Many signaling related genes like serine/threonine protein kinase showed induction during the incompatible interaction while repression in the compatible one. Leucine-rich repeat trans-membrane protein kinase to name a few was induced in both cases attesting their role in plant defense.

We found that around 315 differentially expressed genes are ubiquitous, suggesting broad similarities in stress responses across most of the organisms and confirming cross communicating pathways playing role in different kinds of stresses. However, only 25 differentially expressed genes were found to be canonical all of which showed an overlap with ubiquitous class. A significantly large number of differentially expressed genes (382) were found to be noncanonical (FIG. 5). Interestingly, more than thirty five percent of the repressed and induced gene clusters represented NSH and hypothetical proteins in the compatible interaction while in case of the incompatible interaction around thirty eight percent of the induced cluster belonged to the above mentioned classes while the repressed cluster paved the way for about thirty percent of the hypothetical and NSH proteins. These proteins do not have known cellular roles and thus can now be annotated as being involved in immune response pathway.

Expression Analysis of Selected ESTs by RNA Blot Analysis

To confirm the differential expression of immune-responsive genes, four highly abundant genes in our CaEST dataset showing induced gene expression were selected for RNA blot analysis. The results showed that all four ESTs had a strong induction in root tissue at 24 h post infection and the level of gene expression corroborated to that of microarray analyses. The genes encoding alcohol dehydrogenase and pfkB-type kinase, showed a very high expression suggesting that the carbohydrate metabolic pathways are altered in response to vascular wilt. A disease resistance response gene for defense signaling also showed upregulation indicating its role in immune response. The expression level of a fungal gene FOXY, found to be highly abundant both in susceptible and resistant genotypes was consistent with that of microarray data. This gene encodes a transposable element and its induction during plant-pathogen interaction is of interest for the study of such elements and their involvement in immunity vs. disease.

Our study is directed towards creating a gene resource (CaEST database) of chickpea for the systematic analysis of genotype-dependent organ-specific stimuli-responsive gene signatures that would provide an initial platform for gene discovery and functional genomics of this third most important but understudied food legume. This approach may be used in future to dissect diverse and overlapping biochemical pathways encompassed by the identified transcripts at individual level. This will also be important in long-term efforts to develop faithful, quantitative models for plant processes. The efficiency of subtracted genotype specific immune responsive EST sequencing is especially reflected in the number of new genes identified in this study, which is still moderate in size. A total of 2013 unigenes are reported that characterize the immune responsive transcripts of this important legume, of which approximately twelve percent represent new chickpea genes hitherto undiscovered. Our discovery of a large number of SNPs in expressed sequences should allow the genetic mapping of many genes underlying agricultural characteristics in chickpea. Although WR315 and JG62 may be presumably quite similar to one another at the nucleotide sequence level, we find they are equally different to each other in their transcript profile. In addition, the use of this approach in our present study led to the identification of 807 genes of unknown function now assigned to the immune response pathway with an organ specific localization, opens up a new area of investigation wherein the combining of our CaUnigene dataset with other databases could be used to draw relationships at system level. The results identified a set of 649 non-cannonical stress responsive genes which has never been associated with immune response. Further, homology search of the derived amino acid sequence data from the present study provides a firm indication of a number of components of the root to which function is still to be ascribed. The ESTs identified in this study represent the major attempt so far to define chickpea transcriptome. The microarray analysis of immune-responsive transcriptome uncovers new regulators of host-pathogen interaction. Assigning a functional role to each of these new immune regulators will be challenging and quite valuable in order to know the physiological significance of plant immunity. Nevertheless, the sequence information of chickpea is unavailable and the number of functionally annotated ESTs is low at this time, as this number increases, the transcriptome data will be proven even more useful. The recent identification of immune responsive genes from other organisms would eventually lead to develop a comparative species-specific immune responsive transcriptome in which this report becomes one of the first attempts. This is an initial attempt in the direction that will be expanded upon during future transcriptomic studies of plant processes. Our future efforts will focus onto enriching CaUnigene database and increasing the number of analyzed genes thereof, with an aim to draw a complete functional map of organ specific stimuli responsive transcriptome at individual level. Further, we will focus onto identifying the dynamics associated with the organ specific transcriptome towards cells metabolic and regulatory pathways at different physiological conditions shaping the phenome diversity.

Molecular Cloning of IRF817 Polynucleotide (SEQ ID NO: 6273) Encoding a bHLH Protein (SEQ ID NO: 6274)

In our study, we developed a differential transcriptome of chickpea under pathostress. Several transcripts were identified and cloned. We chose one of these transcripts, designated as IRF817 (Immune responsive factor 817), that was represented as a singleton, for this study. Full-length cloning of IRF817 using 3' and 5' RACE based on CaEST (CaF1_WIE_34_F_11 SEQ ID NO:4861) yielded 0.750 kb cDNA clone. Sequence analysis revealed that the actual transcript size of IRF817 is 750 bp with a coding region of 687 bp, 24 bp of 5'- and 39 bp of 3'-UTRs, respectively. The cDNA encodes for a protein consisting of 228 amino acids with approximate molecular weight of 25.193 kDa having isoelectric point of 6.63. It codes for a protein with a basic helix loop helix (bHLH) DNA binding domain (amino acid 70 to 119) and a caspase domain (amino acids 94 to 169). In silico analysis with ExPASy ProtParam tool revealed the presence of approximately 14% basic, 14% acidic and 76% neutral amino acids. The homology search against GenBank database showed that CaGene1 had maximum homology with an unnamed protein of *Vitis vinifera* and bHLH transcription factor of *Nicotiana*. It also showed homology to an unknown protein of *Medicago* and IAA-Leu resistant DNA binding protein of *Arabidopsis*. This gene stands out to be a novel candidate to study immune response as it does not get any close functionally characterized homologue in a BLAST-P search. This bHLH transcription factor sequence was also observed to be having a caspase domain which makes it unique. Further its expression can be utilized to generate a new variety of crop which can self stimulate itself to raise the bar against a combination of environmental stress responses.

IRF817 is a Low Copy Gene in Chickpea

To find out the genomic organization of IRF817, genomic PCR was performed using gene specific primers and chickpea genomic DNA as template that showed amplification of a 687 bp amplicon exactly matching the size of the cDNA (FIG. 6A) indicating that IRF817 is an intron-less gene in chickpea. Earlier reports on presence and distribution of introns in bHLH family proteins has shown that 80% of the members of this family in *Arabidopsis* and rice contain introns and the intron position is conserved even though the number varies (Toledo-Ortiz et al., 2003; Li et al., 2006). However, in this study the absence of intron suggests that this gene family might differ in genomic organization in legumes. Further, we performed the genomic southern in order to find out the copy number of IRF817. Genomic DNA extracted from chickpea was digested with different restriction enzymes. The blot was hybridized with 32P-labeled ORF of IRF817 fragment. EcoRV and NcoI, having single site in the probe region, produced three bands, whereas HindIII and NotI having no restriction sites produced double and single band respectively (FIG. 6B). This result indicates that the gene encoding IRF817 is present in more than one but as low copies in chickpea.

IRF 817, a Genotype-Independent Early Transcription Regulator

Further, we investigated the expression of IRF817 in both compatible and incompatible interactions by northern blot analyses using total RNA extracted from JG-62 and WR-315, respectively. The results showed that IRF817 gene had some basal expression in both the genotypes indicating its requirement in normal developmental processes. However, it was found to be highly regulated under patho-stress upon *Fusarium* infection. Expression of IRF817 reached maximal level within 6 h of post-infection remained up to 48 h and diminished by 5 day. However, the expression did not show any major difference between the susceptible and resistant genotypes (FIG. 7A-B). Altogether these data suggest IRF817 has a crucial and universal role to play in early phase of immunity.

IRF718, a Multiple Hormone Inducible Gene and Express Organ-Specifically

To examine the organ specificity of IRF817 transcript, we initially compared transcript abundance in different organs (roots, stems, and leaflets) by Northern analysis (FIG. 8). The results showed that the gene was expressed in all the three tissue types, however, the expression was maximum in root followed by stem and leaf. Thus, IRF817 plays regulatory role against vascular wilt in multiple organs. Root being the first organ to come in contact with the pathogen showed highest expression, again suggesting the early regulation of immune pathway by IRF817 in order to check the pathogen at the very early onset of the disease.

Next, we investigated whether IRF817 expression is affected by any hormones or other molecule, such as NO by quantitative real time PCR (FIG. 9). IRF817 was induced in response to SA by 1 h, quickly reaching its maxima at 6 hours after treatment. The transcript level remained to be at the same level of increase up to 6 h but increased a little at 12 h in case of JA treatment. IRF817 expression also increased during progressive time points after ACC treatment with maximum level at 12 hours. Brassinosteroid and NO also induced its expression. In case of NO, there was an initial down-regulation of IRF817 followed by upregulation at 3 and 6 hours and down-regulation at 12 hours, indicating a rhythmic pattern of expression. Further, the gene was found to be down-regulated in response to ABA except a slight increase at 12 h. These results suggest that IRF817 expresses in response to almost all the hormones which are known to play role in plant stress response and developmental pathways, thereby further confirming its role in plant immunity and development.

Regulation of IRF817 by Sub-Cellular Localization

It is thought that a distinct functional role of a protein may be conferred by its subcellular localization. In silico analysis identified a clear N-terminal localized nuclear targeting sequence in IRF817. To further confirm, a co-localization experiment was carried out wherein, the IRF817-GFP was found to be accumulated predominantly in the nucleus while GFP alone was accumulated throughout the cell (FIG. 10). The nuclear localization of IRF817 was in confirmation with earlier studies showing that the bHLH proteins are present in nucleus where they bind to DNA and perform their regulatory functions.

Over-Expression of IRF817 Polynucleotide (SEQ ID NO: 6273) Encoding a bHLH Protein (SEQ ID NO: 6274) Exhibits Immunity in Plants To investigate the functional role of IRF817 in plant, we constitutively expressed a functional IRF817 polynucleotide (SEQ ID NO: 6273) encoding a bHLH protein (SEQ ID NO: 6274 in a susceptible variety (JG-62) of chickpea. Since chickpea is highly recalcitrant to in vitro regeneration and genetic transformation, we established a transformation using *Agrobacterium rhizogenes* to determine the in planta gene function. The IRF817 over-expressed transgenic chickpea seedlings were grown alongside the susceptible non-transgenic control chickpea seedlings under identical conditions. Surprisingly, the transgenic seedlings overexpressing the IRF817 polynucleotide (SEQ ID NO: 6273) displayed an increased tolerance up to 99% to fungal pathogen *Fusarium* in terms of wilting of seedlings as compared to susceptible non-transgenic control seedlings. Unexpectedly, it was observed that the transgenic chickpea seedlings show improved immunity to the fungal pathogen over the non transgenic resistant chickpea seedlings. We then microscopically observed the development, penetration and colonization of the fungal pathogen in transgenic and the control chickpea root. Confocal microscopy revealed a gradual increase of fungal colonization and proliferation leading to extensive hyphal network on and inside the control roots (FIG. 11A), while invasive inter- and intracellular growth of the pathogen was significantly reduced in transgenic roots (FIG. 11C) in comparison to the control, indicating IRF817 mediated fungal resistance in plants. The fungus was found to enter through the collar region into the root vascular bundles by killing of the cells in the root epidermis. It is known that dead tissue is characterized by the absence of intact plant nuclei. To confirm that fungal colonization associates with dead cells, we double-stained root segments from the fungal challenged plants with DAPI for intact plant nuclei and wheat germ agglutinin-Texas Red (WGA-Texas Red) for fungal chitin. We found a close spatial association of strong fungal colonization (FIG. 11A) and DAPI-negative cells (FIG. 11B) in the control roots, further suggesting that massive development of the fungus in the root leads to the death of the host cells in the control. In contrary, the IRF817 transgenic roots showed DAPI positive cells (FIG. 11D) associated with very few hyphae (FIG. 11C), showing thereby immunity to the fungal pathogen. Corroborating with cell viability study, TUNEL assay revealed that although at the early onset of disease, apoptotic cells were found both in control and IRF817 root surface but as disease progressed IRF817 transgenic roots did not show any apoptotic cells while control roots showed continuous increase in TUNEL positive nuclei. Altogether our data suggest IRF817 expression leads to increased immunity against patho-stress in plants.

Bacteria and Yeast Expressed IRF817 was Functionally Active

To further investigate whether IRF817 specifically interact with DNA and has the transactivation capability; we cloned it into *E. coli* and yeast vectors, designated as GST-IRF817 and Gal4-IRF817 (FIG. 12-13). Over-expressed fusion proteins of IRF817 were found to be functionally active.

Another embodiment of the present invention provides polynucleotide having nucleotide sequence as set forth in SEQ ID NO: 6273 encoding protein having amino acid sequence as set forth in SEQ ID NO: 6274, wherein the polynucleotide is responsible for conferring immunity in plant against fungal pathogen.

One embodiment of the present invention provides the polynucleotides that include DNA molecules specifically EST DNA molecules or a fragment thereof. The fragments may comprise smaller oligonucleotides having from about 15 to about 250 nucleotide residues, and more preferably, about 15 to about 30 nucleotide residues.

Another embodiment of the present invention provides the polynucleotides that include DNA molecules specifically EST DNA molecules or a fragment thereof that are marker molecules.

Yet another embodiment of the present invention provides polynucleotides that include nucleic acid molecules that encode a protein or fragment thereof.

Yet another embodiment of the resent invention provides polynucleotides that are Expressed sequence tag (EST) molecules.

Still another embodiment of the present invention provides Expressed sequence tag derived from chickpea.

Still yet another embodiment of the present invention provides ESTs derived from chickpea. The ESTs disclosed in the present invention are classified into various functional classes such as cell cycle control and cell division; cellular redox state; cellular transport/inorganic ion transport and metabolism; cytoskeleton; defense mechanism; development/storage/dormancy and senescence; energy production and conversion; hormone responsive; translation, ribosomal structure and biogenesis; transcription; stress; signaling; secondary metabolism; RNA processing and modification; DNA replication, recombination and repair; post translational modification; protein turn over and chaperons; photosynthesis; nucleotide binding proteins and metabolism.

One embodiment of the present invention provides polynucleotide of Expressed sequence tag having nucleotide sequence selected from a group consisting of SEQ ID NO: 1 to SEQ ID NO: 6272.

Another embodiment of the present invention provides an isolated nucleotide sequence as set forth in SEQ ID NO: 6273 encoding the protein having amino acid sequence as set forth in SEQ ID NO: 6274.

Another embodiment of the present invention provides a recombinant vector comprising the nucleotide sequence as set forth in SEQ ID NO: 6273 encoding the protein having amino acid sequence as set forth in SEQ ID NO: 6274, wherein the nucleotide sequence is operably linked to a promoter.

Yet another embodiment of the present invention provides a recombinant host cell comprising the nucleotide sequence as set forth in SEQ ID NO: 6273 encoding the protein having amino acid sequence as set forth in SEQ ID NO: 6274, wherein the host cell is *E. coli, Agrobacterium* or yeast.

Still another embodiment of the present invention provides a method of improving immunity against fungal pathogen in plants, said method comprises transforming a plant cell with a polynucleotide having the nucleotide sequence as set forth in SEQ ID NO: 6273 encoding protein having amino acid sequence as set forth in SEQ ID NO: 6274, selecting the transformed plant cell and regenerating the transformed plant cell into transgenic plant showing improved immunity to the fungal pathogen.

Further embodiment of the present invention provides a Still another embodiment of the present invention provides a method of improving immunity against *Fusarium* in plants, said method comprises transforming a plant cell with a polynucleotide having the nucleotide sequence as set forth in SEQ ID NO: 6273 encoding protein having amino acid sequence as set forth in SEQ ID NO: 6274, selecting the transformed plant cell and regenerating the transformed plant cell into transgenic plant showing improved immunity to *Fusarium*.

Yet another embodiment of the present invention provides the method of improving immunity against fungal pathogen in plants, said method comprises transforming a plant cell with a polynucleotide having the nucleotide sequence as set forth in SEQ ID NO: 6273 encoding protein having amino acid sequence as set forth in SEQ ID NO: 6274, selecting the transformed plant cell and regenerating the transformed plant cell into transgenic plant showing improved immunity to the fungal pathogen, wherein the plant is monocot or dicot.

Yet another embodiment of the present invention provides the method of improving immunity against fungal pathogen in plants, said method comprises transforming a plant cell with a polynucleotide having the nucleotide sequence as set forth in SEQ ID NO: 6273 encoding protein having amino acid sequence as set forth in SEQ ID NO: 6274, selecting the transformed plant cell and regenerating the transformed plant cell into transgenic plant showing improved immunity to the fungal pathogen, wherein the plant is selected from a group consisting of tobacco, potato, sweet potato, cassava, sugarbeet, *Arabidopsis, brassica* species, tomato, Brinjal, *capsicum*, chili, banana, mango, *vitis*, papaya, sunflower, cotton, groundnut, pea, soybean, chickpea, pigeon pea, *medicago*, lotus, rice, maize, wheat, rye, barley, oats, sorghum, nuts, avocado, turmeric; saffron, ginger, garlic, onion, and nutmeg.

In one embodiment of the present invention there is provided a transgenic plant having improved immunity against a fungal pathogen, wherein the transgenic plant over-expresses a polynucleotide having the nucleotide sequence as set forth in SEQ ID NO: 6273.

In another embodiment of the present invention there is provided a transgenic seed obtained from the transgenic plant over-expressing a polynucleotide having the nucleotide sequence as set forth in SEQ ID NO: 6273, wherein the seed over-expresses a polynucleotide having the nucleotide sequence as set forth in SEQ ID NO: 6273.

In another embodiment of the present invention there is provided a transgenic progeny obtained from the transgenic seed over-expressing a polynucleotide having the nucleotide sequence as set forth in SEQ ID NO: 6273, wherein the progeny over-expresses a polynucleotide having the nucleotide sequence as set forth in SEQ ID NO: 6273.

EXAMPLES

It should be understood that the following examples described herein are for illustrative purposes only and that various modifications or changes in light will be suggested to persons skilled in the art and are to be included within the spirit and purview of this application and the scope of the appended claims.

Example 1

Plant Material and in-Planta Infection

The chickpea (*Cicer arietinum. L*) seeds maintained in the laboratory were sterilized with 70% ethanol and 0.1% $HgCl_2$ followed by repetitive washing in autoclaved water. The seedlings were grown in sterile conditions in glass tubes containing MS basal medium solidified with 0.6% agar in an environmentally controlled growth room and maintained at 25±2° C., 50±5% relative humidity under 16 h photoperiod (270 μmol m-2 s-1 light intensity). *Fusarium oxysporum* ciceri race 1 was grown in potato dextrose broth (PDB) at 28° C. The 3-week old seedlings were inoculated with *Fusarium* spore suspension at a concentration of $1\times10^6$/ml while the control plants were treated with water. The control samples refer to the RNA prepared from the unstressed seedlings harvested from different time period during the course of the experiment. Root and collar (root and shoot junction) tissue was sampled as experimental material, harvested at 6, 12, 24, 48 h and 5 days after inoculation and stored at −80° C. after quick-freezing in liquid nitrogen.

Example 2

Construction of cDNA Libraries

Two suppression subtracted cDNA libraries were constructed, one from a susceptible (JG-62) and the other from a resistant (WR-315) genotype using PCR select cDNA subtraction kit (Clontech, Calif.). Total RNA was isolated by GITC method from uninfected seedlings (used as driver) and *Fusarium* infected seedlings (used as tester) collected at different time points as mentioned above and subsequently combined. The poly (A)$^+$ RNA from the pooled total RNA was purified by using Dyna beads oligo (dT) (Dynal biotech, USA). The cDNAs were cloned into pGEMT vector (Promega, Wis.) and transformed into *E. coli* cells (DH56). The individual clones were picked up and grown in deep well plates in 2× YT media containing ampicillin (75 µg/ml) at 3TC for 16-18 hours under shaking at 250 rpm. All individual clones were stored in 96 well U bottom plates by mixing 220 µl of grown culture and 30 µl of 80% glycerol for long term storage.

Example 3

Sequencing, Processing and Assembly of ESTs into Contigs

Plasmid DNAs from both the subtracted cDNA libraries were isolated and purified by Perfectprep Plasmid 96 Vac Direct bind kit according to the manufacturer's instructions (Eppendorf, Germany). The quality of the plasmid DNAs was analyzed by 0.8% agarose gel electrophoresis and the good quality plasmids having appropriate DNA concentration and free from any mix up were selected for sequencing. The individual plasmids were sequenced using the BigDye terminator cycle sequencing kit (Perkin Elmer, Applied Biosystems) with M13 forward and reverse primers for 5' and 3' single pass sequencing respectively, in ABI PRISM 3700 Sequencer (Applied Biosystems, CA). Sequence base calls were made using Phred with a quality cutoff of 15. Vector filtering was performed using the cross match program (P. Green, http://bozeman.mbt.Washington.edu/phrap.docs/phrap.html) followed by trimming of low quality sequences. The sequences were individually inspected for chimeras, short reads, *E. coli* and mitochondrial sequences which were subsequently removed. The processed ESTs with 100 bases or longer were assembled into contigs by CAP3 programme using standard parameters. The final assembly of contigs and singletons constituted the chickpea gene index.

Blast Analysis, Annotation and Comparison

The EST contig and singleton sequences were annotated for homology using BLASTX and BLASTN algorithms against non redundant protein and nucleotide databases respectively. For BLASTX, an e-value cut-off of $10^{-15}$ was used and the sequences with e-value below this cutoff were then subjected to BLASTN analysis with e-value cutoff of $10^{-20}$. In addition, BLASTN was used to compare the chickpea sequences from this study to a database of legume sequences. This database included sequences of *Lotus japonicus* (gene index release 3.0); *Medicago truncatula* (gene index release 8.0); *Glycine max* (gene index release 12.0) and *Phaseolus vulgaris* (gene index release 1.0) from The Institute for genomic Research (TIGR; Quackenbush et al, 2001) and *Arachis hypogea, Cajanus cajan, Pisum sativum* and *Robinia pseudoacacia* available from NCBI taxonomy browser (http://www.ncbi.nlm.nih.gov/Taxonomy/taxonomyhome.html). The following criteria were used in stand-alone BLASTN comparison: (1) exact match bp=11; (2) e-value≤$10^{-5}$ and (3) DNA identity≥80% and 90%. Further, TBLASTX (with e-value cutoff of 1015) was used for comparing chickpea sequences to GenBank's EST_others database for the identification of chickpea specific sequences. Sequences were additionally functionally characterized in the context with the Gene Ontology (GO), Metacyc and COG. Cross species comparison of stress responsive transcriptome was carried out by searching each gene of unigene set against all classes of the stress responsive gene entries in the GO database (http://www.geneontology.org). Genes which had a match in more than one group of stress responsive genes were categorized as ubiquitous and those which were earlier known to be involved in *Fusarium* stress as found from the fungal responsive group in the GO database were categorised as canonical. Remaining of the genes which did not show any match in any of the stress responsive gene groups in the GO database were classified as non canonical.

Identification of Gene Families Using Single-Linkage Clustering

In order to identify gene families, the chickpea contigs and singletons were combined into a single dataset. TBLASTX with e-value cutoff of $10^{-15}$ was used to compare the dataset against itself. Sequences with at least one sequence in common in their BLAST reports were combined into a putative gene family.

Identification of SNPs

For the identification of SNPs, the ace file output of CAP3 programme was used as input to the PolyBayes SNP detection program along with the base values assigned by Phred for each of the contigged sequences. Perl scripts were used to parse the PolyBayes output file. The cutoff value for the probability of SNP was put at 0.99. Only base change mutations were considered in order to avoid any discrepancy in the results due to any error in the alignment. The SNPs were further divided into high-quality if minimum of two sequences from each genotype showed the same base change and low-quality if minimum of two sequences from one genotype and one from the other showed the same base change.

Example 4

Construction of cDNA Microarray

The cDNA microarray setup consisted of 6072 probes corresponding to 1749 unigenes. The cDNA clones from both susceptible and resistant libraries were amplified by performing colony PCR (1×PCR buffer, 1.5 mM $MgCl_2$, 5 units Taq DNA polymerase (Applied biosystems, USA), 0.5 mM dNTPs (Fermentas, Canada), 0.2 µM M13 primer (Sigma), 20 ng of template DNA) in 96 well format. The PCR amplified products were purified using Perfectprep PCR clean up kit as per manufacturer's instructions (Eppendorf, Germany). The quality of the PCR products was checked on 1.0% agarose gels. Five microliters of the PCR products were reorganized on the 384-well printing plates with 5 µl of 100% DMSO and printed in duplicates on the poly-L-lysine coated slides (Sigma) using a high throughput arrayer (Arrayer ESI, SDDC2) followed by UV cross linking. The spiking and other controls such as DMSO, SSC, water and previously cloned chickpea genes like 18S rRNA and actin were also printed at different locations in the chickpea microarray which were used as negative and positive controls.

Sample Preparation, Labeling and Microarray Hybridization

In order to find out the differential gene expression during host-pathogen compatible and incompatible interactions, root tissue sample were collected from *Fusarium* infected JG62 and WR 315 seedlings, respectively after different post-infection time points. Water treated JG62 and WR 315 plants were taken as control. Two biological replicates were done. Total RNA was isolated using Trizol reagent (Invitrogen, CA). 6 µg of the total RNA was used for cDNA synthesis using indirect TSA labeling and detection kit Micromax (PerkinElmer, Boston, Mass.). The RNA isolated from uninfected and infected tissue was labeled with flourscein and biotin, respectively. The labeled cDNA was purified using microcon YM 100 columns (Millipore, Bedford, Mass.). The purified flourscein and biotin labeled cDNAs were mixed and hybridized to the microarray slides in hybridization chambers (Corning, USA) at 65° C. water bath for 16 hours. The slides were washed for 10 minutes in 0.5×SSC and 0.01% SDS, 10 minutes in 0.06×SSC and 0.01% SDS and for 5 minutes in 0.06×SSC. The slides were subsequently processed for replacement of flourscein with Cy3 and biotin with Cy5 as per manufacturer's instructions. The experiment was carried out in duplicate.

Scanning and Data Analysis

Micraoarrays were scanned using Scan array 5000 scanner (PerkinElmer, Mass.) to produce two separate tiff images. Spot finding and quantification of the spots were done by using Scan array express software (PerkinElmer, Mass.). Spots appearing bad due to poor morphology, high local background and bubbles were flagged off and were excluded from further analysis. Spots with both channel intensities less than 500 were also filtered out. Spots were quantified using an adaptive method. Avadis software (PerkinElmer, Mass.) was used for further data transformation which consisted of background correction and normalization. For background correction, local background intensity of each spot was subtracted from its foreground intensity value. Due to non linearity of the data, intensity dependent Lowess normalization was applied. Cy5/Cy3 signal ratio was also calculated. Although, indirect TSA labeling was performed to generate the fluorescent labeled probe that obviates the need for control dye swap experiments, initially dye swap experiment was performed for checking the reciprocity of the gene signals that showed high correlation between the original and dye swap slides. Cross slide one class t-test with Benjamini and Horchberg FDR multiple correction was performed on the four replicate data points for each clone. P value of 0.05 and fold induction of 2.5 was used as a limit for statistically significant differences in the expression. The resulting differentially expressed gene list was uploaded for hierarchical clustering using MEV software (TIGR). Using the differential expression profile and the sequence metadata of the corresponding CaESTs immune responsive gene regulatory network models were developed.

Example 5

RNA Gel Blots and Real Time PCR

Validation of the microarray results was done by northern analysis of few transcripts. For this, total RNA was extracted from root tissue of water treated and *Fusarium* challenged plants collected after treatment using trizol reagent (Invitrogen). 20 µg of RNA was denatured in 50% formamide, 17% formaldehyde, and 10% MOPS buffer (200 mM MOPS, pH7.0, 50 mM sodium acetate and 1 mM EDTA) at 65° C. for 5 min and was separated on 1.2% agarose gel containing 22 M formaldehyde in MOPS buffer, transferred to GenScreen plus membrane (Hybond-N, Amersham Biosciences) by downward capillary blotting in 20×SSC. The DNA probes were prepared by random primer labeling and purified by passing through Sephadex G-50 column as described in Sambrook et al., 2001. After 2 hrs of prehybridization in 0.3 M Nacl, 5% formamide, 10% dextran sulfate and 1% SDS, at 42° C., the radiolabeled probe was added and hybridization was carried out at the same temperature for 16-18 h. After stringent washing, the blot was exposed to X ray film (Kodak, Rochester, N.Y.). Further, the microarray result was validated by performing quantitative real time PCR. Total RNA samples from all time points of each genotype were quantified using a spectrophotometer (Nanodrop Technologies). 5 µg of total RNA was used for preparation of cDNA using Reverse transcriptase kit (Applied Biosystems). The cDNA was diluted 10 times and qRT-PCR was performed for each clone of interest in triplicates using Sybr Green Mastermix (Applied biosystems) and ABI 7500 sequence detection system according to the manufacturer's protocol (Applied Biosystems). The relative quantification method (ΔΔ-CT) was used to evaluate quantitative variation between the replicates examined. The amplification of 18S RNA was used as an endogenous control to normalize the datasets.

Example 6

Cloning of Full Length IRF817

Full length cDNA clone of IRF817 having nucleotide sequence as set forth in SEQ ID NO: 6273 was obtained by performing 3' and 5' RACE using gene specific primers and RACE kits (Invitrogen). The gene specific primers were designed from the sequence of EST clone (CaF1_WIE_34_F11). 3'RACE was performed using gene specific primer (IRF817-3'F, 5'-AAGAAGAGGGGTAGATCGGATTCAT-3' SEQ ID NO: 6283) and UAP primer provided with the 3'RACE kit. 5'RACE was performed by using two gene specific primers (IRF817-5'R1, 5'-ATTAGGCTCAATCTTG-GAGCCTGGA-3' SEQ ID NO: 6284) and IRF817-5'R2, 5'-GTTGGTGTTGAAATTGATGGCTCTCTGGGG-3 SEQ ID NO: 6285') and AP from the kit. The amplified products were run on 1% agarose gel, purified with gel extraction kit (Qiagen) and the purified products were then cloned into pGEM-T Easy (Promega) vector. The 3' and 5' RACE products cloned in pGEM-T were named as p3'IRF817 and p5'IRF817 respectively. The clones were sequenced using standard procedure of sequencing. For the amplification of the full length cDNA, gene specific primers were designed from the nucleotide sequences as obtained from the alignment of the p3'IRF817, p5'IRF817 and CaF1_WIE_34_F11 clones. The full length cDNA was amplified by PCR using cDNA as template and the gene specific primer pair IRF817-F1 (5'-ATGGTTTCCCCGGAAAACACCAATTG-GCTTTT-3' SEQ ID NO: 6286) and IRF817-R1 (5'-TTAG-GCAACTGGTGGGCGGA-3' SEQ ID NO: 6287). The PCR product was run on 1% agarose gel, gel purified using gel extraction kit (Qiagen) and subsequently cloned into the pGEM-T Easy vector to yield pIRF817. The complete cDNA sequence was determined by automated DNA sequencer (ABI Prism 3700).

Example 7

Amplification of IRF817 from Genomic DNA and Genomic Southern

Genomic DNA was extracted using DNeasy Plant Mini Kit (Qiagen). The genomic clone of IRF817 was made by using genomic DNA as template and gene specific primer pair IRF817-F1 (5'-ATGGTTTCCCCGGAAAACACCAATTG-GCTTIT-3' SEQ ID NO: 6286) and IRF817-R1 (5'-TTAG-GCAACTGGTGGGCGGA-3' SEQ ID NO: 6287) by amplifying the genomic ORF. Genomic southern was performed in order to find out the copy number of IRF817 in chickpea. Aliquots of 10 µg of genomic DNA were digested with different restriction enzymes HindIII, Nod, NcoI and EcoRV.

The digested samples were resolved on 0.8% agarose gel, denatured and blotted onto Genescreenplus membrane (Amersham Biosciences). Immobilised nucleic acids were hybridized with $^{32}$P-labelled amplicon of IRF817 obtained using IRF817-F1 (SEQ ID NO: 6286) and IRF817-R1 (SEQ ID NO: 6287) primer pair.

Example 8

Northern Blotting

Northern-blot analysis was performed to determine the expression pattern of IRF817 in response to vascular wilt and its organ-specific expression. For this, 20 μg of RNA samples were separated on a 1.5% formaldehyde-agarose gel and then blotted onto Genescreenplus membrane (Amersham). IRF817 was amplified from its EST clone using M13 forward (5'-GTTTTCCCAGTCACGACGTTG-3' SEQ ID NO: 6288) and reverse primers (5'-TGAGCGGATAACAATTTCACA-CAG-3' SEQ ID NO: 6289). The amplicon was run on 1% gel, gel purified and the purified product was used for preparing $^{32}$P-dCTP labelled probe by random labelling using random labelling kit (NEB).

Example 9

Various Treatments and Quantitative Real Time PCR Analyses of IRF718

Different hormones were applied on two weeks old chickpea seedlings. The treatment of SA, JA, ACC, BR, 2,4-D, ABA and NO were given by spraying 1 mM, 100 μM, 500 μM, 50 μM, 50 μM, 100 μM and 1 mM respectively. For control the seedlings were sprayed with the respective buffers. The tissues were harvested at different time-points upto 12 h after the treatment. The harvested tissues were instantly frozen in liquid nitrogen and stored at −80° C. For quantitative RT-PCR, total RNA was extracted using TRIzol reagent and used for cDNA synthesis by High-Capacity cDNA Reverse Transcription kit (Applied Biosystems). The cDNA was diluted 10 times and qRT-PCR was performed in triplicates in ABI 7500 sequence detection system using SYBR Green Master Mix (Applied Biosystems) and gene specific primers IRF718RT-F and IRF817RT-R. The relative quantification method (ΔΔ-CT) was used to evaluate quantitative variation between the replicates examined. The amplification of 18S RNA was used as an endogenous control to normalize the dataset.

Example 10

Bacterial Over-Expression of IRF817

For the bacterial over-expression IRF817 was PCR amplified from T-vector clone using primers: FP (5'-GGATC-CATGGTTTCCCCGGAAAACACC-3' SEQ ID NO: 6275) and RP (5'-GCGGCCGCTTAGGCAACTGGTGGGCGGA-3' SEQ ID NO: 6276). The PCR products were digested and cloned at the BamHI and NoI sites of pGEX-4T2 (Amersham Biosciences) in order to produce the recombinant GST-IRF817 (FIG. 12). Recombinants were screened and transformed into E. coli BL21 strain for over-expression of fusion protein using 0.6 mM-1 mM isopropylthio-β-galactoside.

Example 11

Yeast Over-Expression of IRF817

For the yeast over-expression IRF817 was amplified using primers: FP (5'-CCGGAATTCATGGTTTCCCCGGAAAA-CAC-3' SEQ ID NO: 6277) and RP (5'-CGCGGATCCT-TAGGCAACTGGTGGGCGGA-3' SEQ ID NO: 6278). The PCR product was digested and cloned at EcoRI and BamHI site of pGBKT7 vector (Clontech) to express IRF817 protein fused to GAL4 DNA-BD ((FIG. 13). The construct was transformed into yeast strain AH109 (Clontech) for over-expression in yeast cells.

Example 12

Subcellular Localization of IRF817

The subcellular localization of IRF817-GFP fusion protein was studied by performing transient expression assay using onion epidermal cells. The coding region of IRF817 was amplified by PCR using gene specific FP (5'-GAAGATC-TATGGTTTCCCCGGAAAACACCAATTGGCT-3' SEQ ID NO: 6279) and RP (5'-GGACTAGTGGCAACTG-GTGGGCGGACTTCAT-3' SEQ ID NO: 6280), respectively having BglII and SpeI overhang. The PCR products were digested and cloned in frame with GFP at Bgl II and SpeI sites of pCAMBIA1302 (CAMBIA) vector to yield IRF817-GFP (FIG. 14). The empty GFP plasmid was used as a control. Plasmids were introduced in onion peel by particle bombardment (PDS-1000/He; Bio-Rad, Calif., USA) using 1 μm gold particles and further analyzed by confocal laser scanning microscope (Leica Microsystems, Germany), for subcellular localization. The cells were imaged using the 488-nm line of an argon laser.

Example 13

Plant Transformation

In order to generate transgenic lines for plant over-expression of IRF817, ORF of IRF817 was PCR amplified using gene specific primers: FP (5'CGCGGATCCATGGTTTC-CCCGGAAAACAC-3' SEQ ID NO: 6281); RP (5'-CCCGAGCTCTTAGGCAACTGGTGGGCGGA-3' SEQ ID NO: 6282). The PCR product was digested and cloned into the BamHI and SacI sites of the binary vector pBI121 (Clontech) under the control of CaMV 35S promoter. The resultant construct (FIG. 15) was further mobilized into *Agrobacterium tumefaciens* strain EHA105.

Example 14

Generation and Analyses of Transgenic Chickpea Roots

For in planta constitutive over-expression and tagging expression, IRF817-GFP and the empty vector (GFP) were introduced into *Agrobacterium rhizogenes* strain K599 by electroporation and used to inoculate 5-7 old *C. arientinum* (cv. JG-62) seedlings at the cut end of radical near the point of attachment to the cotyledon. The transformed plantlets having hairy roots were maintained on MS agar media containing 15 mg/l hygromycin under fluorescent light with a 16-h photoperiod. The plantlets with 7-10 days old transformed roots and the wild type roots were infected with $10^6$ spores/ml of *Fusarium oxysporum* ciceri race I. For mock reactions transgenic roots and wild type roots were treated with water. The resultant plants were screened by GFP expression using a Leica SP2 LCM confocal microscope.

For monitoring the fungal invasion, root segments were fixed with 4% parafolmaldehyde made in 1 μM PBS. Fixed root segments were transferred to an enzyme solution containing 10 mg/ml driselase and 1 mg/ml BSA (Sigma, St. Louis, Mo.) dissolved in 25_mM phosphate buffer at room temperature for 15 mM. After rinsing in PBS, roots were further treated with 0.5% Triton X-100 in PB for 10 min. Hyphae in root segments were stained with the chitin-specific dye WGA-Texsas Red (Molecular Probes, Germany) in PBS (10 µg/ml) followed by destaining in PBS (pH 7.4) prior to imaging.

A TUNEL assay was performed using an in situ cell death detection kit (Fluorescein; Roche Applied Science, Germany) according to the instruction manual. In addition to root fixation, root segments were dehydrated and dewaxed by passage for 15 min through series of increasing concentrations of ethanol in water (from 10% to 100% in 10% increments) and back from 100% to 0% in 10% increments). Subsequently, segments were incubated in 50 µl of TUNEL reaction mixture. Grade 1_DNase I-treated roots were used as positive controls. Solutions were vacuum-infiltrated thrice and incubated for 60 min at 37° C. in humidified atmosphere in the dark. Destaining of the segments was done with PBS (pH 7.4).

Plant nuclei were stained with 5 µg/ml DAPI for 30 min following TUNEL assay and WGA staining. During incubation in DAPI, segments were vacuum infiltrated once for 1 min at 25 mmHg (1 mm Hg=133 Pa) and then rinsed with PBS.

Confocal fluorescence imaging was done with a multichannel Leica SP2 (Bensheim, Germany) confocal microscope with a 488-nm laser excitation and 505-540 nm emission for GFP and fluorescin; 543-nm excitation and 560-630 nm emission for WGA-Texas red; and 595-nm excitation and 615-nm emission for DAPI.

TABLE 1

Chickpea library and EST characterization

| | Genotype | | |
|---|---|---|---|
| | Total | WR | JG |
| Sequence reads | 6955 | 4047 | 2908 |
| Failed base calling QC | 8 | 6 | 2 |
| Low quality sequence | 214 | 121 | 93 |
| Short insert sequence | 422 | 246 | 176 |
| No insert | 30 | 30 | 0 |
| E. coli | 0 | 0 | 0 |
| Mitochondrial | 9 | 1 | 8 |
| Total high quality | 6272 | 3643 | 2629 |

TABLE 2

Sequencing and contigging statistics of chickpea ESTs, Sequencing success was determined by removing low quality, short insert, no insert and mitochondrial ESTs from the total number of ESTs sequenced

| Genotype | Total No. of ESTs sequenced | Sequencing success percentage[a] | Good-quality ESTs used for contigging[b] | ESTs in contigs | EST singletons |
|---|---|---|---|---|---|
| JG-62 | 2908 | 90.4 | 2629 | 2316 | 313 |
| WR-315 | 4047 | 90.0 | 3643 | 2916 | 727 |
| Total ESTs | 6955 | 90.2 | 6272 | 5232 | 1040 |

TABLE 3

Comparative matching of the chickpea to the ESTs of other legume databases, the chickpea ESTs isolated in this study were compared to other legume databases like Arachis hypogea, Cajanus cajan, Pisum sativua, Robinia psedoacacia, Lotus japonicus, Medicago trunculata, Glycine max and Phaseolus vulgaris collected from NCBI and TIGR gene indices. The criteria for stand alone BLASTn were (1) exact match = 11; (2) E-value cutoff 1E5; and (3) identity >80% and 90% at DNA sequence level.

| Gene indices | Identity > 80% | Identity > 90% |
|---|---|---|
| Arachis hypogea | 1686 (83.75) | 1118 (55.54) |
| Cajanus cajan | 1764 (87.6) | 1729 (85.89) |
| Pisum sativum | 1788 (88.8) | 1599 (79.43) |
| Robinia pseudoacacia | 245 (12.17) | 79 (3.92) |
| Lotus japonicus | 872 (43.31) | 287 (14.25) |
| Medicago trunculata | 1168 (58.02) | 614 (30.50) |
| Glycine max | 1617 (80.32) | 635 (31.54) |
| phaseolus vulgaris | 928 (46.10) | 234 (11.62) |

REFERENCES

Ewing R M, Kahla A B, Poirot O, Lopez F, Audic S, Clayerie J M: Large-scale statistical analyses of rice ESTs reveal correlated patterns of gene expression. Genome Res 1999, 9: 950-959.

Gray W M: Plant defense: A New Weapon In The Arsenal. Currt Biol, 2002:12:352-354.

Jantasuriyarat C, Gowda M, Haller K, Hatfield J, Lu G, Stahlberg E, Zhou B, Li H, Kim H, Yu Y, Dean R A, Wing R A, Soderlund C, Wang G L: Large-scale identification of expressed sequence tags involved in rice and rice blast fungus interaction. Plant Physiol 2005, 138: 105-115.

Jones S: An overview of the basic helix-loop-helix proteins. Genome Biol 2004, 5: 226.

Katagiri F: A global view of defense gene expression regulation—a highly interconnected signaling network. Curr Opin Plant Biol 2004, 7: 506-511.

Koornneef A, Pieterse C M J: Cross Talk in Defense Signaling. Plant Physiol 2008, 146: 839-844.

LeBlanc J C, Gonsalves E R, Mohn W W: Global response to desiccation stress in the soil actinomycete Rhodococcus jostii RHA1. Appl Environ Microbiol 2008, 74: 2627-2636.

Li X, Duan X, Jiang H, Sun Y, Tang Y, Yuan Z, Guo J, Liang W, Chen L, Yin J, Ma H, Wang Zhang D: Genome-Wide Analysis of Basic/Helix-Loop-Helix Transcription Factor Family in Rice and Arabidopsisl. Plant Physiology 2006, 141: 1167-1184.

Melamed D, Pnueli L, Arava Y: Yeast translational response to high salinity: global analysis reveals regulation at multiple levels. RNA 2008, 14: 1337-1351.

Murre C, McCaw P S, Baltimore D: A new DNA binding and dimerization motif in immunoglobulin enhancer binding, daughterless, MyoD, and myc proteins. Cell 1989, 56: 777-783.

Nagata T, Iizumi S, Satoh K, Kikuchi S: Comparative molecular biological analysis of membrane transport genes in organisms. Plant Mol Biol 2008, 66: 565-585.

Nucci M, Anaissie E: Fusarium infections in immunocompromised patients. Clin Microbiol Rev 2007, 20:695-704.

Ramírez M, Graham M A, Blanco-López L, Silvente S, Medrano-Soto A, Blair M W, Hernández G, Vance C P, Lara M: Sequencing and analysis of common bean ESTs. Building a foundation for functional genomics. Plant Physiol 2005, 137: 1211-1227.

Sander A, Beyer U, Amberg R: Systemic Fusarium oxysporum infection in an immunocompetent patient with an adult respiratory distress syndrome (ARDS) and extracorporal membrane oxygenation (ECMO). *Mycoses* 1998, 41:109-11

Satoh K, Doi K, Nagata T, Kishimoto N, Suzuki K, Otomo Y, Kawai J, Nakamura M, Hirozane-Kishikawa T, Kanagawa S, et al: Gene organization in rice revealed by full-length cDNA mapping and gene expression analysis through microarray. *PLoS ONE* 2007, 2: e1235.

Takabatake T, Ishihara H, Ohmachi Y, Tanaka I, Nakamura M M, Fujikawa K, Hirouchi T, Kakinuma S, Shimada Y, Oghiso Y, Tanaka K: Microarray-based global mapping of integration sites for the retrotransposon, intracisternal A-particle, in the mouse genome. *Nucleic Acids Res* 2008, 36: e59.

Toledo-Ortiz G, Huq E, Quail P H: The *Arabidopsis* basic/helix-loop helix transcription factor family. Plant Cell 2003, 15: 1749-1770.

Udall J A, Swanson J M, Haller K, Rapp R A, Sparks M E, Hatfield J, Yu Y, Wu Y, Dowd C, Arpat A B, et al: A global assembly of cotton ESTs. *Genome Res* 2006, 16: 441-450.

Wellmer F, Alves-Ferreira M, Dubois A, Riechmann J L, Meyerowitz E M: Genome-wide analysis of gene expression during early *Arabidopsis* flower development. *PLoS Genetics* 2006, 2: 1012-1024.

White J A, Todd J, Newman T, Focks N, Girke T, de Ilarduya M, Jaworski J G, Ohlrogge J B, Benning C: A new set of *Arabidopsis* expressed sequence tags from developing seeds. The metabolic pathway from carbohydrates to seed oil. *Plant Physiol* 2000, 124: 1582-1594.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09163255B2). An electronic copy of the "Sequence Listing" will also be available from the USPTO upon request and payment of the fee set forth in 37 CFR 1.19(b)(3).

We claim:

1. An isolated cDNA sequence as set forth in SEQ ID NO: 6273 encoding a protein having the amino acid sequence as set forth in SEQ ID NO: 6274.

2. A recombinant vector comprising the cDNA sequence as set forth in SEQ ID NO: 6273 encoding a protein having the amino acid sequence as set forth in SEQ ID NO: 6274, wherein the cDNA sequence is operably linked to a heterologous promoter.

3. A recombinant host cell comprising the cDNA sequence as set forth in SEQ ID NO: 6273 encoding a protein having the amino acid sequence as set forth in SEQ ID NO: 6274, wherein the host cell is *E. coli, Agrobacterium*, or yeast.

4. A method of improving immunity against a fungal pathogen in plants, comprising: (a) transforming a plant cell with the cDNA sequence as set forth in SEQ ID NO: 6273 encoding a protein having the amino acid sequence as set forth in SEQ ID NO: 6274, (b) selecting the transformed plant cell, and (c) regenerating the transformed plant cell into a transgenic plant that demonstrates improved immunity to the fungal pathogen, as compared to a plant that does not express the amino acid sequence of SEQ ID NO: 6274.

5. The method of claim 4, wherein the fungal pathogen is selected from the genus of *Fusarium*.

6. The method of claim 4, wherein the plant is a monocot or a dicot.

7. The method of claim 4, wherein the plant is selected from the group consisting of tobacco, potato, sweet potato, cassava, sugar-beet, *arabidopsis, brassica* species, tomato, brinjal, *capsicum*, chili, banana, mango, *vitis, papaya*, sunflower, cotton, groundnut, pea, soybean, chickpea, pigeon pea, *medicago*, lotus, rice, maize, wheat, rye, barley, oats, sorghum, nuts, avocado, turmeric, saffron, ginger, garlic, onion, and nutmeg.

8. A transgenic plant or parts thereof having immunity against a fungal pathogen, wherein the transgenic plant overexpresses a polypeptide encoded by the sequence as set forth in SEQ ID NO: 6273.

9. A transgenic seed obtained from the transgenic plant of claim 8, wherein the seed overexpresses a polypeptide encoded by the cDNA sequence as set forth in SEQ ID NO: 6273.

10. A transgenic progeny obtained from the transgenic seed of claim 9, wherein the progeny overexpresses a polypeptide encoded by the cDNA sequence as set forth in SEQ ID NO: 6273.

* * * * *